United States Patent [19]

Minoshima et al.

[11] Patent Number: 5,731,452
[45] Date of Patent: Mar. 24, 1998

[54] 7-THIAPROSTAGLANDINS AND METHOD OF PRODUCTION THEREOF

[75] Inventors: Toru Minoshima; Kenichiro Kataoka; Hiroko Tanaka; Koji Ishii; Noriaki Endo, all of Hino, Japan

[73] Assignee: Teijin Limited, Osaka, Japan

[21] Appl. No.: 532,743

[22] PCT Filed: Jan. 18, 1995

[86] PCT No.: PCT/JP95/00042

§ 371 Date: Sep. 18, 1995

§ 102(e) Date: Sep. 18, 1995

[87] PCT Pub. No.: WO95/19340

PCT Pub. Date: Jul. 20, 1995

[30] Foreign Application Priority Data

Jan. 18, 1994 [JP] Japan ................. 6-003566
Aug. 1, 1994 [JP] Japan ................. 6-180091

[51] Int. Cl.⁶ ............................................. C07F 7/08
[52] U.S. Cl. .................. 556/427; 560/17; 560/118; 560/121; 562/431; 562/498; 562/503
[58] Field of Search ................. 556/427; 560/17, 560/118, 121; 562/431, 498, 503

[56] References Cited

U.S. PATENT DOCUMENTS 5,159,102 10/1992 Tanaka et al. ................. 556/427 X

*Primary Examiner*—Paul F. Shaver
*Attorney, Agent, or Firm*—Sughrue, Mion, Zinn, Macpeak & Seas, PLLC

[57] ABSTRACT

7-thiaprostaglandins having the formula (I) which inhibit cell migration induced by monocyte chemoattractant protein MCP-1/MCAF and other chemokines and can serve as drugs for the treatment of atherosclerosis, diabetic angiopathy, and other disorders, their enantiomers, mixtures of the same, and methods of production thereof.

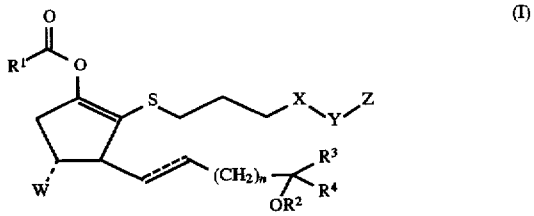

11 Claims, No Drawings

7-THIAPROSTAGLANDINS AND METHOD OF PRODUCTION THEREOF

TECHNICAL FIELD

The present invention relates to novel 7-thiaprostaglandins having the ability to inhibit cell migration and useful as a pharmaceutical, a method of production of the same, intermediates useful for their synthesis and applications.

BACKGROUND ART

Prostaglandins have diverse physiological activities such as inhibition of platelet aggregation, vasodilation, hypotension, suppression of the secretion of gastric acids, smooth muscle constriction, cytoprotection, and diuresis and are useful for the treatment or prevention of cardiac infarction, angia, artereosclerosis, hypertension, duodenal ulcers, oxytocia, and abortion. Among these, prostaglandin E, analogues have a potent inhibitory activity of platelet aggregation and a potent vasodilator activity and are already being used clinically.

It has been disclosed that 7-thiaprostaglandin $E_1$ derivatives exhibit various activities such as inhibitation of platelet aggregation, hypotension, vasodilation, and a resultant action against thrombus, angia, cardiac infarction, arteriosclerosis, and metastatis of malignant tumors and exhibit an antitumor action [Japanese Unexamined Patent Publication (Kokai) No. 53-68753, Japanese Unexamined Patent Publication (Kokai) No. 58-110562, Japanese Unexamined Patent Publication (Kokai) No. 59-29661, Japanese Unexamined Patent Publication (Kokai) No. 60-185761, Japanese Unexamined Patent Publication (Kokai) No. 61-204163]. Further, these 7-thiaprostaglandin $E_1$ derivatives are known to be useful for neuropathy in diabetes [Japanese Unexamined Patent Publication (Kokai) No. 64-52721].

On the other hand, enol butyrate of prostaglandin $E_1$ are known as prostaglandin $E_1$ analogues (Japanese Unexamined Patent Publication (Kokai) No. 5-213862). It is only shown, however, that they are stable even when prepared under high temperatures and that they can give a physiological activity equal to that of prostaglandin $E_1$. No suggestion at all is made about the physiological activity of the compounds of the present invention given below.

By the way, in the past, as a method of production of prostaglandin $E_1$ analogues, it was known that it was possible to synthesize prostaglandin $E_1$ analogues by a two-component coupling type reaction of a cyclopentenone derivative having a side chain corresponding to an α-chain and organolithioaluminates of the ω-chain portion [M. J. Weiss et al., J. Org. Chem. 44, 1439 (1978)]. Further, the method given below was known as an example of the synthesis by a two-component coupling type reaction using the organolithiocuprates of the ω-chain portion as a nucleophilic reagent [K. G. Untch et al., J. Am. Chem. Soc. 94, 7826, (1972), R. Pappo, P. W. Collins, Tetrahedron Lett. 4217, (1954), Kurozumi et al., Chem. Pharm. Bull. 35, 1102, (1982), C. K. Sih, J. Am. Chem. Soc. 97, 865, (1975), Sato et al., Japanese Unexamined Patent Publication (Kokai) No. 1-228933].

Similarly, as a method of synthesis of 7-thiaprostaglandin $E_1$ analogues, a two-component coupling reaction of cyclopentenone derivatives having an α-chain of the 7-thia-type and organolithiocuprates of the ω-chain portion is known [Tanaka et al., Chem. Pharm. Bull. 33, 2359 (1985)].

Further, as a method of production of enol butyrate of prostaglandins, Japanese Unexamined Patent Publication (Kokai) No. 5-213862 described a method of production of the following formula (XII):

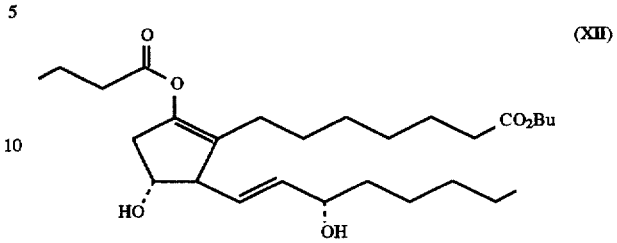

According to this method, they are produced by, for example, protecting the hydroxyl group of the 1-iodo-3-hydroxy-1-octene, carrying out a reaction with alkyllithium to make 1-lithioalkene, then carrying out a reaction with a trialkylphosphine-copper (I) iodide complex to make organolithiocuprate, then carrying out 1,4-conjugate addition of the organolithiocuprate to the 4-hydroxy-2-(6-carbobutoxyhexyl)-2-cyclopentene-1-on with the protected hydroxyl group, then quenching by adding anhydrous butyric acid or a butyric acid halide to the reaction mixture.

On the other hand, it is known to synthesize the prostaglandin $E_1$ derivative, misoprostol by the method of producing cuprate in situ from the vinylstannane type ω-chain portion using higher order cyanocuprates, then carrying out a 1,4-conjugate addition to a cyclopentenone derivative having a side chain corresponding to the α-chain [James R. Behling et al., J. Am. Chem. Soc. 110, 2641 (1988)]. This reference shows that it is possible to make just one of the two stannyl groups of the trans-1,2-bis(tributylstannyl)ethylene a cuprate and perform 1,4-conjugate addition on the unsubstituted cyclohexanone.

Further, the method of substituting the stannyl group of the vinylstannane with iodine while maintaining the configuration so as to derive an iodoolefin is described for example in F. Sato et al., Tetrahedron Lett. 28, 2033, (1987), G. A. Tolstikov et al., Synthesis. (6), 496, (1986), etc.

Further, the method of using chromium (II) chloride ($CrCl_2$) to cause addition of an alkenyl halide to a carbonyl compound by the Grignard method has been developed by Nozaki et al. [Kazuhiko Takai et al., Tetrahedron Lett. 24, 5281, (1983)]. This method has been discussed in further detail by Kishi et al., which showed that the desired substance can be obtained with a good reproducibility and high yield by addition of a catalytic amount of nickel chloride (II) or palladium acetate (II) [Haolun Jin et al., J. Am. Chem. Soc. 108, 5644 (1986)].

Further, the synthesis intermediate of the method of production of the present invention including the coupling reaction using chromium (II) chloride ($CrCl_2$), that is, the above compound of the formula (XI), is novel. There is no example of use for the synthesis of prostaglandins.

DISCLOSURE OF THE INVENTION

Accordingly, the object of the present invention is to provide novel 7-thiaprostaglandin derivatives which inhibit cell migration induced by chemokines, for example, monocyte chemoattractant protein, MCP-1/MCAF, and is useful as an agent for the treatment of arteriosclerosis, diabetic angiopathy, and the like.

Here, chemokines (also known as intercrines) are the generic name for polypeptidic inflammatory/immunoregulatory factors produced by activated macrophages and leukocytes, etc. of lymphoid tissues and inflammatory sites. They are approximately 10 kd basic and heparin-binding protein with four cysteines, which form disulfide bonds. The main activity is a cell migration inducing activity. Interleukin-8, MIP-1α/β (abbreviation for macrophage inflammatory protein-1α/β), MCP-1 (abbreviation for monocyte chemoattractant protein-1), etc. fall under this category. They are one family of cytokines in which involvement in various chronic and acute inflammatory disorders is suggested [for example, see Michiel, D. (1993) Biotechnology, 11, 739, Oppenheim, J. J. et al. (1991), Annual Review of Immunology, 9, 617 to 648, Neote, K. et al. (1993) Cell, 72, 415 to 425, Schall, T. J. (1991) Cytokine, 3, 165 to 183, etc.]

Among these, monocyte chemoattractant protein, MCP-1 (also known as MCAF (abbreviation for macrophage chemotactic and activating factor) is a chemokine having a monocyte migration inducing activity which is produced by various stimuli from T-lymphocytes, macrophages, smooth muscle cells, fibroblasts, endothetial cells, etc. It has been known that MCP-1 induces the accumulation of blood monocytes/macrophages into the sites of inflammation, and activates the accumulated monocytes/macrophages in diseases in which monocytes/macrophages are deeply involved in the progression of the diseases, such as restenosis or reocclusion after trauma to the intima of arteries in angioplasty etc., stenosis or occlusion due to progression of atherosclerosis at the coronary artery, carotid artery, etc., coronary transplantation-associated arteriosclerosis, rejection of organ transplants, rheumatoid arthritus, glomular nephritus, diabetic microangiopathy, and other diseases. Therefore, it is strongly suggested that MCP-1 is deeply involved in the occurrence and progression of these lesions [for example, see Leonard, E. J. and Yoshimura, T. (1990) Immunology Today, 11, 97 to 101, Nelken, N. A. et al, The Journal of Clinical Investigation (1991), 88, 1121 to 1127, Koch, A. E. et al., The Journal of Clinical Investigation (1992), 90, 772 to 779, Hanazawa, S. et al. (1993) The Journal of Biological Chemistry, 268, 9526 to 9532, Graves, D. T. et al., American Journal of Pathology (1992), 140, 9 to 14, Edgington, S. M., Bio/Technology (1993), 11, 676 to 681, Adams, D. H. et al., Immunological Reviews (1993), no. 134, 5 to 19, etc.] Drugs inhibiting the cell migration induced by MCP-1/MCAF can be expected to be useful as agents for the treatment and/or agents for the prevention of restenosis or reocclusion occurring after trauma to the intima of the arteries in angioplasty etc., stenosis or occlusion due to progression of atherosclerosis at the coronary artery, carotid artery, etc., coronary transplantation-associated artereosclerosis, diabetic angiopathy, glomular nephritus, rheumatoid arthritus, osteoarthritus, organ transplant rejection, etc.

With regard to the method of producing the novel 7-thiaprostaglandins, it is necessary to synthesize a large number of compounds efficiently. Ideally there are several methods suited to the partial structures that we want to change. Therefore, there has been needs for development of a method enabling easy conversion of the enol ester portion of the 9-position and a method facilitating the conversion of the ω-chain portion.

The present inventors engaged in intensive studies on the possibilities of novel 7-thiaprostaglandin derivatives inhibiting the cell migration induced by chemokines and as a result discovered that the 7-thiaprostaglandin derivatives of the present invention are powerful inhibitors of cell migration induced by chemokines, for example, monocyte chemoattractant protein MCP-1/MCAF, further discovered that these compounds suppress the neointimal proliferation after balloon injury of the artery, and thereby reached the present invention. Further, they discovered that 7-thiaprostaglandins of the present invention have activity for inhibiting platelet aggregation.

That is, in accordance with the present invention, there are provided 7-thiaprostaglandins comprising the compounds having the formula (I):

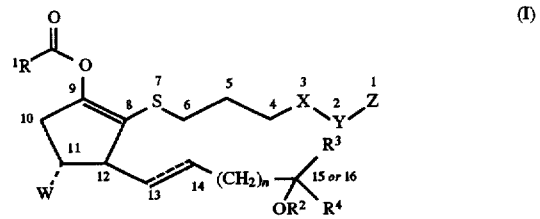

(The small-sized numbers in italic are base upon the numbering of prostanoic acid)

wherein, $R^1$ is a $C_1$ to $C_{10}$ straight or branched alkyl group, $C_2$ to $C_{10}$ straight or branched alkenyl group, substituted or unsubstituted phenyl group, substituted or unsubstituted $C_3$ to $C_{10}$ cycloalkyl group, substituted or unsubstituted phenyl ($C_1$ to $C_2$)alkyl group, substituted or unsubstituted phenoxy ($C_1$ to $C_7$)alkyl group, or group representing a substituted or unsubstituted amine acid residue including the carbonyl group of the enol ester, $R^2$ is a hydrogen atom, tri($C_1$ to $C_7$ hydrocarbon)silyl group, or a group forming an acetal bond along with the oxygen atom of the hydroxyl group, $R^3$ is a hydrogen atom, 20 methyl group, or vinyl group. $R^4$ is a $C_1$ to $C_8$ straight or branched alkyl group, $C_2$ to $C_8$ straight or branched alkenyl group, $C_2$ to $C_8$ straight or branched alkynyl group, substituted or unsubstituted phenyl group, substituted or unsubstituted $C_3$ to $C_{10}$ cycloalkyl group, or further straight or branched $C_1$ to $C_5$ alkyl group, to $C_5$ alkenyl group, or $C_2$ to $C_5$ alkynyl group substituted with a $C_1$ to $C_5$ alkoxyl group, substituted or unsubstituted aromatic group, substituted or unsubstituted phenoxy group, substituted or unsubstituted $C_3$ to $C_{10}$ cycloalkyl group, or substituted or unsubstituted hereto ring group, W is a hydrogen atom, hydroxyl group, tri($C_1$ to $C_7$ hydrocarbon)siloxy group, or group forming an acetal bond, X—Y is an ethylene group, vinylene group, or ether bond where X is an oxygen atom and Y is methylene, Z is $CO_2R^5$ or $CONR^6R^7$, $R^5$ is a hydrogen atom, $C_1$ to $C_{10}$ straight or branched alkyl group, $C_2$ to $C_{10}$ straight or branched alkenyl group, substituted or unsubstituted phenyl group, substituted or unsubstituted $C_3$ to $C_{10}$ cycloalkyl group, substituted or unsubstituted phenyl ($C_1$ to $C_2$)alkyl group, or 1 equivalent of a cation, $R^6$ and $R^7$ may be the same or different and represent a hydrogen atom, $C_1$ to $C_5$ straight or branched alkyl group, or group forming a $C_4$ to $C_6$ hetero ring with the nitrogen atom of the amide, n is 0 or 1, and the symbol $=$ represents a double bond or single bond, or their enantiomers, or mixtures of any ratio of the same. In the 7-thiaprostaglandins of the above formula (I), $R^1$ is a $C_1$ to $C_{10}$ straight or branched alkyl group, $C_2$ to $C_{10}$ straight or branched alkenyl group, substituted or unsubstituted phenyl group, substituted or unsubstituted $C_3$ to $C_{10}$ cycloalkyl group, substituted or unsubstituted phenyl($C_1$ to $C_2$)alkyl group, substituted or unsubstituted phenoxy($C_1$ to $C_7$)alkyl group, or group representing a substituted or unsubstituted amino acid residue containing the carbonyl group of the enol ester. As preferable examples of the $C_1$ to $C_{10}$ straight or branched alkyl group, a methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group etc. may be mentioned. As preferable examples of the $C_2$ to $C_{10}$ straight or branched alkenyl group, the vinyl group, allyl group, 3-butenyl group, 2-butenyl group, 4-pentenyl group, 2-pentenyl group, purenyl group (3-methyl-2-butenyl group), 2,4-hexadienyl group, 2,6-octyldienyl group, neryl group, geranyl group, citronellyl group, farnesyl group, arachidyl group, etc. may be mentioned. Further, as preferable examples of the substituent of the substituted or unsubstituted phenyl group, a halogen atom, hydroxyl group, $C_2$ to $C_7$ acyloxy group, halogen atom-substitutable $C_1$ to $C_4$ alkoxyl group, nitrile group, nitro group, carboxyl group, ($C_1$ to $C_6$) alkoxylcarbonyl group, etc. may be mentioned. These substituents may be substituted at any position of the ortho, meta, para positions of the phenyl group. Further, the substitution may be performed by any combination of plurality of substituents. As preferable examples of the substituted or unsubstituted $C_3$ to $C_{10}$ cycloalkyl group, a cyclopropyl group, cyclopentyl group, cyclohexyl group, cyclohexenyl group, cycloheptyl group, cyclooctyl group, cyclodexyl group, etc. may be mentioned. These may be substituted by a $C_1$ to $C_5$ alkyl group or $C_1$ to $C_5$ alkoxyl group at any position. As the substituted or unsubstituted phenyl($C_1$ to $C_2$)alkyl group, a benzyl group substituted or unsubstituted by the same substituents as the above-mentioned phenyl group, α-phenethyl group, β-phenethyl group, etc. may be mentioned. As the substituted or unsubstituted phenoxy($C_1$ to $C_7$)alkyl group, one substituted or unsubstituted with the same substituents as the above-mentioned phenyl group may be mentioned. Further, as the amino acid of the group representing a substituted or unsubstituted amino acid residue containing the carbonyl group of the enol ester, alanine, arginine, asparagine, asparagic acid, cysteine, glutamine, glutamic acid, glycine, histidine, isoleucine, leucine, lysine, methionine, phenylalanine, proline, serine, threonine, tryptophan, tyrosine, valine, etc. may be mentioned. Among these, as $R^1$, a $C_1$ to $C_{10}$ straight or branched alkyl group or substituted or unsubstituted phenyl group is preferred. A propyl group is particularly preferred.

In the 7-thiaprostaglandins of the above formula (I), $R^2$ is a hydrogen atom, tri($C_1$ to $C_7$ hydrocarbon)silyl group, or a group forming an acetal bond along with the oxygen atom of the hydroxyl group. As preferred examples of the tri($C_1$ to $C_7$ hydrocarbon)silyl group, a trimethylsilyl group, triethylsilyl group, tertbutyldimethylsilyl group, and other tri($C_1$ to $C_4$ alkyl)silyl groups, a tert-butyldiphenylsilyl group and other diphenyl($C_1$ to $C_4$)alkyl silyl groups, a tribenzylsilyl group, etc. may be mentioned. As preferable examples of the group forming an acetal bond along with the oxygen atom of the hydroxyl group, the methoxymethyl group, 1-ethoxyethyl group, 2-methoxy-2-propyl group, 2-ethoxy-2-propyl group, (2-methoxyethoxy)methyl group, benzyloxymethyl group, 2-tetrahydropyranyl group, 2-tetrahydrofuranyl group, 6,6-dimethyl-3-oxa-2-oxobicyclo[3.1.0]hex-4-il group, etc. may be mentioned. Among these, as the $R^2$, a hydrogen atom, trimethylsilyl group, 2-tetrahydropyranyl group, and tertbutyldimethylsilyl group are particularly preferred.

In the 7-thiaprostaglandins of the above formula (I), $R^3$ is a hydrogen atom, methyl group, or vinyl group, but among these a hydrogen atom and methyl group are preferred.

In the 7-thiaprostaglandins of the above formula (I), $R^4$ is a $C_1$ to $C_8$ straight or branched alkyl group, $C_2$ to $C_8$ straight or branched alkenyl group, $C_2$ to $C_8$ straight or branched alkynyl group, substituted or unsubstituted phenyl group, substituted or unsubstituted $C_3$ to $C_{10}$ cycloalkyl group, or further straight or branched $C_1$ to $C_5$ alkyl group, $C_2$ to $C_5$ alkenyl group, or $C_2$ to $C_5$ alkynyl group substituted by a $C_1$ to $C_5$ alkoxyl group, substituted or unsubstituted aromatic group, substituted or unsubstituted phenoxy group, substituted or unsubstituted $C_3$ to $C_{10}$ cycloalkyl group, or substituted or unsubstituted hetero ring group. As preferable examples of the $C_1$ to $C_8$ straight or branched alkyl group, a methyl group, ethyl group, propyl group, butyl group, pentyl group, hexyl group, heptyl group, octyl group, 1-methyl-1-butyl group, 2-methylhexyl group, 2-hexyl group, and 1,1-dimethylpentyl group may be mentioned. As preferable examples of the $C_2$ to $C_8$ straight or branched alkenyl group, the allyl group, 3-butenyl group, 2-butenyl group, 4-pentenyl group, and 2-pentenyl group may be mentioned. As preferable examples of the $C_2$ to $C_8$ straight or branched alkynyl group, the ethynyl group, 2-propynyl group, 1-propynyl group, 2-butynyl group, 3-butynyl group, 3-hexynyl group, and 1-methyl-3-hexynyl group may be mentioned. As preferable examples of the substituents of the substituted phenyl group, the same substituents mentioned as the substituents of the substituted phenyl group at $R^1$ may be mentioned. Further, as preferable examples of the substituted or unsubstituted $C_3$ to $C_7$ cycloalkyl group, a cyclopropyl group, cyclopentyl group, cyclohexyl group, cyclohexenyl group, cycloheptyl group, cyclooctyl group, cyclodecyl group etc. may be mentioned. These may be substituted at any position by the $C_1$ to $C_5$ alkyl group or $C_1$ to $C_5$ alkoxyl group. As preferable examples of the $C_1$ to $C_5$ alkoxyl group used as a substituent in the straight or branched $C_1$ to $C_5$ alkyl group, $C_2$ to $C_5$ alkenyl group, or $C_2$ to $C_5$ alkynyl group substituted by a $C_1$ to $C_5$ alkoxyl group, substituted or unsubstituted aromatic group, substituted or unsubstituted phenoxy group, substituted or unsubstituted $C_2$ to $C_{10}$ cycloalkyl group, or substituted or unsubstituted hetero ring group, a methoxy group, ethoxy group, propoxy group, isopropoxy group, butoxy group, tert-butoxy group, hexyloxy group, etc. may be mentioned. As preferable examples of the aromatic group used as the substituent, the phenyl group, naphthyl group, etc. may be mentioned. As preferable examples of the $C_3$ to $C_{10}$ cycloalkyl group used as the substituent, the preferable examples of the cycloalkyl group at $R^1$ mentioned above may be mentioned. As preferable examples of the hetero ring group used as the substituent, a thienyl group, furanyl group, imidazolyl group, pyridyl group, pyradinyl group, etc. may be mentioned. Among these substituents, an aromatic group, phenoxy group, or hetero ring group may further be substituted. As the substituent in this case, the substituents mentioned as the substituents of the substituted phenyl group of $R^1$ may be mentioned. Regarding the positions and the numbers of the substituents as well, those mentioned for the substituted phenyl at $R^1$ may be applied as they are. As the straight or branched $C_1$ to $C_5$ alkyl group, $C_2$ to $C_5$ alkenyl group, and $C_2$ to $C_5$ alkynyl, a methyl group, ethyl group, propyl group, isopropyl group, butyl group, isobutyl group, sec-butyl group, tert-butyl group, pentyl group, allyl group, 3-butenyl group, 2-butenyl group, 4-pentenyl group, 2-pentenyl group, ethynyl group, 2-propynyl group, 1-propynyl group, 2-butynyl group, 3-butynyl group, etc. may be mentioned. The above substituents may be bonded at any position of these $C_1$ to $C_5$ alkyl group, $C_2$ to $C_5$ alkenyl group, and $C_2$ to $C_5$ alkynyl group. Among these, as $R^4$, a $C_3$ to $C_8$ straight or branched alkyl group, substituted or unsubstituted $C_3$ to $C_{10}$ cycloalkyl group, and a straight or branched $C_1$ to $C_5$ alkyl group substituted by a substituted or unsubstituted aromatic group are preferred. A pentyl group, 2-methylhexyl group, cyclohexyl group, and substituted or unsubstituted benzyl group are particularly preferred.

In the 7-thiaprostaglandins of the above formula (I), W is a hydrogen atom, hydroxyl group, tri($C_1$ to $C_7$ hydrocarbon) siloxy group, or group forming an acetal bond. As preferred examples of the tri($C_1$ to $C_7$ hydrocarbon)siloxy group, a trimethylsiloxy group, triethylsiloxy group, tert-butyldimethylsiloxy group, and other tri($C_1$ to $C_4$ alkyl) siloxy groups, tert-butyldiphenylsiloxy group and other diphenyl($C_1$ to $C_4$)alkylsiloxy groups, tribenzylsiloxy group, etc. may be mentioned. As preferable examples of the aceta forming an acetal bond, the methoxymethytoxy group, 1-ethoxyethyloxy group, 2-methoxy-2-propyloxy group, 2-ethoxy-2-propyloxy group, (2-methoxyethyloxy) methyloxy group, benzyloxymethyloxy group, 2-tetrahydropyranyloxy group, 2-tetrahydrofuranyloxy group, 6,6-dimethyl-3-oxa-2-oxobicyclo[3.1.0]hex-4-yloxy group etc. may be mentioned. Among these, as W, a hydrogen atom, hydroxyl group, trimethylsiloxyl group, 2-tetrahydropyranyloxyl group, and tert-butyldimethylsiloxyl group are particularly preferred.

In the 7-thiaprostaglandins of the above formula (I), Z is $CO_2R^5$ or $CONR^6R^7$. $R^5$ is a hydrogen atom, $C_1$ to $C_{10}$ straight or branched alkyl group, $C_2$ to $C_{10}$ straight or branched alkenyl group, substituted or unsubstituted phenyl group, substituted or unsubstituted $C_3$ to $C_{10}$ cycloalkyl group, substituted or unsubstituted phenyl ($C_1$ to $C_2$) alkyl group, or one equivalent of cations. As preferred examples of the $C_1$ to $C_{10}$ straight or branched alkyl group, a methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group etc. may be mentioned. As preferred examples of the $C_2$ to $C_{10}$ straight or branched alkenyl group, the vinyl group, allyl group, 3-butenyl group, 2-butenyl group, 4-pentenyl group, 2-pentenyl group, furanyl group (3-methyl-2-butenyl group), 2,4-hexadienyl group, 2,6-octadienyl group, neryl group, geranyl group, citronelyl group, farnesyl group, arachidyl group etc. may be mentioned. As preferable examples of the substituted or unsubstituted phenyl group, a halogen atom, hydroxyl group, $C_2$ to $C_7$ acyloxy group, $C_1$ to $C_4$ alkyl group substitutable by a halogen atom, $C_1$ to $C_4$ alkoxyl group substitutable by a halogen atom, nitrile group, nitro group, carboxyl group, and ($C_1$ to $C_6$) alkoxycarbonyl group etc. may be mentioned. As a preferable example of the substituted or unsubstituted $C_3$ to $C_{10}$ cycloalkyl group, a cyclopropyl group, cyclopentyl group, cyclohexyl group, cyclohexenyl group, cycloheptyl group, cyclooctyl group, cyclodecyl group, etc. may be mentioned. As the substituted or unsubstituted phenyl ($C_1$ to $C_2$) alkyl group, a benzyl group substituted or unsubstituted by the same substituent as the above mentioned phenyl group, an α-phenethyl group, β-phenethyl group, etc. may be mentioned. As preferable examples of the one equivalents of cations, $NH_4^+$, tetramethylammonium, monomethylammonium, dimethylammonium, trimethylammonium, benzylammonium, phenethylammonium, morpholinium cations, monoethanol ammonium, piperidinium cations, and other ammonium cations; $Na^+$, $K^+$, and other alkali metal cations; ½$Ca^{2+}$, ½$Mg^{2+}$, ½$Zn^{2+}$, ⅓$Al^{3+}$, and other bivalent or trivalent metal cations, etc. may be mentioned. Among these, as $R^2$, a hydrogen atom, $C_1$ to $C_{10}$ straight or branched alkyl group, or $C_2$ to $C_{10}$ straight or branched alkenyl group is preferable. A methyl group is particularly preferred. $R^6$ and $R^7$ may be the same or different and represent a hydrogen atom, $C_1$ to $C_5$ straight or branched alkyl group, or group forming a $C_4$ to $C_6$ hetero ring along with the nitrogen atom of the amide. As preferable examples of the $C_1$ to $C_5$ straight or branched alkyl group, the methyl group, ethyl group, propyl group, isopropyl group, butyl group, isobutyl group, sec-butyl group, pentyl group, etc. may be mentioned. As the hetero ring becoming the group forming the $C_4$ to $C_6$ hetero ring along with the nitrogen atom of the amide, the pyrrolidine ring, pyridine ring, piperadine ring, morpholine ring, etc. may be mentioned. Among these, $R^5$ and $R^6$ are preferably hydrogen atoms.

Further, in the compound of the above formula (I), the configuration of the substituent bonded on the cyclopentanone ring in the compound of the above formula (I) is a particularly useful stereo isomer in that it has the configuration derived from natural prostaglandin $E_1$, but in the present invention the enantiomers, that is, the stereo isomers of the following formula (I)ent:

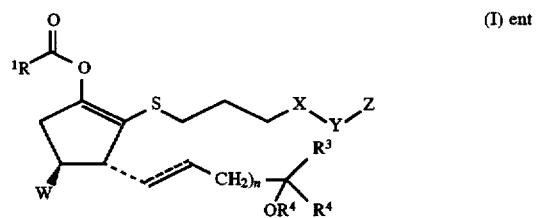

wherein, $R^1$, $R^2$, $R^3$, $R^4$, W, X—Y, Z, n, and the symbol $=$ are the same as defined above or mixtures of any ratio of the same are also included. Further, the carbon substituted with $OR^2$, $R^3$ and $R^4$ is an asymmetric carbon, so there are two types of optical isomers. All of these optical isomers and mixtures of any ratio of the same are included.

As specific preferable examples of the 7-thiaprostaglandins of the above (I) according to the present invention, the following compounds may be mentioned, but the invention is not limited to the same:

01) (11R,12S,13E,15S)-9-acetoxy-11,15-dihydroxy-7-thiaprosta-8,13-dienoic acid 02) (11R,12S,13E,15S)-9-propionyloxy-11,15-dihydroxy-7-thiaprosta-8,13-dienoic acid 03) (11R,12S,13E,15S)-9-butyryloxy-11,15-dihydroxy-7-thiaprosta-8,13-dienoic acid 04) (11R,12S,13E,15S)-9-isobutyryloxy-11,15-dihydroxy-7-thiaprosta-8,13-dienoic acid 05) (11R,12S,13E,15S)-9-valeryloxy-11,15-dihydroxy-7-thiaprosta-8,13-dienoic acid 06) (11R,12S,13E,15S)-9-isovaleryloxy-11,15-dihydroxy-7-thiaprosta-8,13-dienoic acid 07) (11R,12S,13E,15S)-9-pivaroyloxy-11,15-dihydroxy-7-thiaprosta-8,13-dienoic acid 08) (11R,12S,13E,15S)-9-acryloyloxy-11,15-dihydroxy-7-thiaprosta-8,13-dienoic acid 09) (11R,12S,13E,15S)-9-methacryloyloxy-11,15-dihydroxy-7-thiaprosta-8,13-dienoic acid 10) (11R,12S,13E,15S)-9-crotonoyloxy-11,15-dihydroxy-7-thiaprosta-8, 13-dienoic acid 11) (11R,12S,13E,15S)-9-benzoyloxy-11,15-dihydroxy-7-thiaprosta-8,13-dienoic acid 12) (11R,12S,13E,15S)-9-naphthoyloxy-11,15-dihydroxy-7-thiaprosta-8,13-dienoic acid 13) (11R,12S,13E,15S)-9-toluoyloxy-11,15-dihydroxy-7-thiaprosta-8,13-dienoic acid 14) (11R,12S,13E,15S)-9-cyclohexylcarbonyloxy-11,15-dihydroxy-7-thiaprosta-8,13-dienoic acid 15) (11R,12S,13E,15S,17R)-9-acetoxy-11,15-dihydroxy-17,20-dimethyl-7-thiaprosta-8,13-dienoic acid 16) (11R,12S,13E,15S,17R)-9-butyryloxy-11,15-dihydroxy-17,20-dimethyl-7-thiaprosta-8,13-dienoic acid
17) (11R,12S,13E,15S,17S)-9-butyryloxy-11,15-dihydroxy-17,20-dimethyl-7-thiaprosta-8,13-dienoic acid
18) (11R,12S,13E,15S,17R)-9-isobutyryloxy-11,15-dihydroxy-17,20-didimethyl-7-thiaprosta-8,13-dienoic acid
19) (11R,12S,13E,15S,17R)-9-pivaroyloxy-11,15-dihydroxy-17,20-dimethyl-7-thiaprosta-8,13-dienoic acid
20) (11R,12S,13E,15S,17R)-9-benzoyloxy-11,15-dihydroxy-17,20-dimethyl-7-thiaprosta-8,13-dienoic acid
21) (11R,12S,13E,15S)-9-butyryloxy-11,15-dihydroxy-15-methyl-7-thiaprosta-8,13-dienoic acid
22) (11R,12S,13E,15S)-9-butyryloxy-11,15-dihydroxy-15-cyclopentyl-16,17,18,19,20-pentanor-7-thiaprosta-8,13-dienoic acid
23) (11R,12S,13E,15S)-9-butyryloxy-11,15-dihydroxy-15-cyclohexyl-16,17,18,19,20-pentanor-7-thiaprosta-8,13-dienoic acid
24) (11R,12S,13E,15R)-9-butyryloxy-11,15-dihydroxy-15-cyclohexyl-16,17,18,19,20-pentanor-7-thiaprosta-8,13-dienoic acid
25) (11R,12S,13E,15S)-9-butyryloxy-11,15-dihydroxy-15-phenyl-16,17,18,19,20-pentanor-7-thiaprosta-8,13-dienoic acid
26) (11R,12S,13E,15S)-9-butyryloxy-11,15-dihydroxy-16-cyclohexyl-17,18,19,20-tetranor-7-thiaprosta-8,13-dienoic acid
27) (11R,12S,13E,15R)-9-butyryloxy-11,15-dihydroxy-16-cyclohexyl-17,18,19,20-tetranor-7-thiaprosta-8,13-dienoic acid
28) (11R,12S,13E,15S)-9-butyryloxy-11,15-dihydroxy-16-phenyl-17,18,19,20-tetranor-7-thiaprosta-8,13-dienoic acid
29) (11R,12S,13E,15R)-9-butyryloxy-11,15-dihydroxy-16-phenyl-17,18,19,20-tetranor-7-thiaprosta-8,13-dienoic acid
30) (11R,12S,13E,15S)-9-butyryloxy-11,15-dihydroxy-17-phenyl-18,19,20-trinor-7-thiaprosta-8,13-dienoic acid
31) (11R,12S,13E,15S)-9-butyryloxy-11,15-dihydroxy-18-phenyl-19,20-dinor-7-thiaprosta-8,13-dienoic acid
32) (11R,12S,13E,15R)-9-butyryloxy-11,15-dihydroxy-18-phenyl-19,20-dinor-7-thiaprosta-8,13-dienoic acid
33) (11R,12S,13E,15S)-9-butyryloxy-11,15-dihydroxy-19-phenyl-20-nor-7-thiaprosta-8,13-dienoic acid
34) (11R,12S,13E,15R)-9-butyryloxy-11,15-dihydroxy-19-phenyl-20-nor-7-thiaprosta-8,13-dienoic acid
35) (11R,12S,13E,15S)-9-butyryloxy-11,15-dihydroxy-16,16-diphenyl-17,18,19,20-tetranor-7-thiaprosta-8,13-dienoic acid
36) (11R,12S,13E,15R)-9-butyryloxy-11,15-dihydroxy-16,16-diphenyl-17,18,19,20-tetranor-7-thiaprosta-8,13-dienoic acid
37) (11R,12S,13E,15S,16S)-9-butyryloxy-11,15-dihydroxy-16-phenyl-18,19,20-trinor-7-thiaprosta-8,13-dienoic acid
38) (11R,12S,13E,15S,16R)-9-butyryloxy-11,15-dihydroxy-16-phenyl-18,19,20-trinor-7-thiaprosta-8,13-dienoic acid
39) (11R,12S,13E,15R,16S)-9-butyryloxy-11,15-dihydroxy-16-phenyl-18,19,20-trinor-7-thiaprosta-8,13-dienoic acid
40) (11R,12S,13E,15R,16R)-9-butyryloxy-11,15-dihydroxy-16-phenyl-18,19,20-trinor-7-thiaprosta-8,13-dienoic acid
41) (11R,12S,13E,15S)-9-butyryloxy-11,15-dihydroxy-16-phenyl-16-methyl-18,19,20-trinor-7-thiaprosta-8,13-dienoic acid
42) (11R,12S,13E,15R)-9-butyryloxy-11,15-dihydroxy-16-phenyl-16-methyl-18,19,20-trinor-7-thiaprosta-8,13-dienoic acid
43) (11R,12S,13E,15S)-9-butyryloxy-11,15-dihydroxy-16-paratolyl-17,18,19,20-tetranor-7-thiaprosta-8,13-dienoic acid
44) (11R,12S,13E,15R)-9-butyryloxy-11,15-dihydroxy-16-paratolyl-17,18,19,20-tetranor-7-thiaprosta-8,13-dienoic acid
45) (11R,12S,13E,15S)-9-butyryloxy-11,15-dihydroxy-16-metatolyl-17,18,19,20-tetranor-7-thiaprosta-8,13-dienoic acid
46) (11R,12S,13E,15S)-9-butyryloxy-11,15-dihydroxy-16-orthotolyl-17,18,19,20-tetranor-7-thiaprosta-8,13-dienoic acid
47) (11R,12S,13E,15S)-9-butyryloxy-11,15-dihydroxy-16-naphthyl-17,18,19,20-tetranor-7-thiaprosta-8,13-dienoic acid
48) (11R,12S,13E,15S)-9-butyryloxy-11,15-dihydroxy-16-(2-chlorophenyl)-17,18,19,20-tetranor-7-thiaprosta-8,13-dienoic acid
49) (11R,12S,13E,15S)-9-butyryloxy-11,15-dihydroxy-16-(3-chlorophenyl)-17,18,19,20-tetranor-7-thiaprosta-8,13-dienoic acid
50) (11R,12S,13E,15S)-9-butyryloxy-11,15-dihydroxy-16-(4-chlorophenyl)-17,18,19,20-tetranor-7-thiaprosta-8,13-dienoic acid
51) (11R,12S,13E,15S)-9-butyryloxy-11,15-dihydroxy-16-(3-nitrophenyl)-17,18,19,20-tetranor-7-thiaprosta-8,13-dienoic acid
52) (11R,12S,13E,15S)-9-butyryloxy-11,15-dihydroxy-16-(4-nitrophenyl)-17,18,19,20-tetranor-7-thiaprosta-8,13-dienoic acid
53) (11R,12S,13E,15S)-9-butyryloxy-11,15-dihydroxy-16-(3-methoxyphenyl)-17,18,19,20-tetranor-7-thiaprosta-8,13-dienoic acid
54) (11R,12S,13E,15S)-9-butyryloxy-11,15-dihydroxy-16-(4-methoxyphenyl)-17,18,19,20-tetranor-7-thiaprosta-8,13-dienoic acid
55) (11R,12S,13E,15S)-9-butyryloxy-11,15-dihydroxy-16-(3-methoxycarbonylphenyl)-17,18,19,20-tetranor-7-thiaprosta-8,13-dienoic acid
56) (11R,12S,13E,15S)-9-butyryloxy-11,15-dihydroxy-16-(4-methoxycarbonylphenyl)-17,18,19,20-tetranor-7-thiaprosta-8,13-dienoic acid
57) (11R,12S,13E,15S)-9-butyryloxy-11,15-dihydroxy-16-(6-chloro-metatolyl)-17,18,19,20-tetranor-7-thiaprosta-8,13-dienoic acid
58) (11R,12S,13E,15S)-9-butyryloxy-11,15-dihydroxy-16-(3-methyl-5-propylphenyl)-17,18,19,20-tetranor-7-thiaprosta-8,13-dienoic acid
59) (11R,12S,13E,15S)-9-butyryloxy-11,15-dihydroxy-16-(3,5-dimethylphenyl)-17,18,19,20-tetranor-7-thiaprosta-8,13-dienoic acid 60) (11R,12S,13E,15S)-9-butyryloxy-11,15-dihydroxy-16-(3-trifluoromethylphenyl)-17,18,19,20-tetranor-7-thiaprosta-8,13-dienoic acid 61) (11R,12S,13E,15S)-9-butyryloxy-11,15-dihydroxy-16-(2-fluoro-3-methoxyphenyl)-17,18,19,20-tetranor-7-thiaprosta-8,13-dienoic acid 62) (11R,12S,13E,15S)-9-butyryloxy-11,15-dihydroxy-16-(3-fluorophenyl)-17,18,19,20-tetranor-7-thiaprosta-8,13-dienoic acid 63) (11R,12S,13E,15S)-9-butyryloxy-11,15-dihydroxy-16-phenoxy-17,18,19,20-tetranor-7-thiaprosta-8,13-dienoic acid 64) (11R,12S,13E,15S)-9-butyryloxy-11,15-dihydroxy-18-oxa-7-thiaprosta-8,13-dienoic acid 65) (11R,12S,13E,15S)-9-butyryloxy-11,15-dihydroxy-16-furyl-17,18,19,20-tetranor-7-thiaprosta-8,13-dienoic acid 66) (11R,12S,13E,15S)-9-butyryloxy-11,15-dihydroxy-16-thienyl-17,18,19,20-tetranor-7-thiaprosta-8,13-dienoic acid 67) (11R,12S,13E,15S)-9-butyryloxy-11,15-dihydroxy-16-(3-thienyl)-17,18,19,20-tetranor-7-thiaprosta-8,13-dienoic acid 68) (11R,12S,13E,15S)-9-butyryloxy-11,15-dihydroxy-16-pyrrolyl-17,18,19,20-tetranor-7-thiaprosta-8,13-dienoic acid 69) (11R,12S,13E,15S)-9-butyryloxy-11,15-dihydroxy-16-pyridyl-17,18,19,20-tetranor-7-thiaprosta-8,13-dienoic acid 70) (11R,12S,13E,15S)-9-butyryloxy-11,15-dihydroxy-16,16-dimethyl-7-thiaprosta-8,13-dienoic acid 71) (11R,12S,13E,15S)-9-butyryloxy-11,15-dihydroxy-17-methyl-19,20-dinor-7-thiaprosta-8,13-dienoic acid 72) (11R,12S,13E,15R)-9-butyryloxy-11,15-dihydroxy-17-methyl-19,20-dinor-7-thiaprosta-8,13-dienoic acid 73) (11R,12S,13E,15S)-9-butyryloxy-11,15-dihydroxy-16,16,20-trimethyl-7-thiaprosta-8,13-dienoic acid 74) (11R,12S,13E,15S)-9-butyryloxy-11,15-dihydroxy-7-thiaprosta-8,13-diene -18-in acid 75) (11R,12S,13E,15S)-9-butyryloxy-11,15-dihydroxy-16,20-dimethyl-7-thiaprosta-8, 13-diene -18-in acid 76) (11R,12S,13E,16S)-9-butyryloxy-11,16-dihydroxy-7-thiaprosta-8,13-dienoic acid 77) (11R,12S,13E,16S)-9-butyryloxy-11,16-dihydroxy-16-methyl-7-thiaprosta-8,13-dienoic acid 78) (11R,12S,13E,15S)-9-butyryloxy-11,15-dihydroxy-3-oxa-7-thiaprosta-8,13-dienoic acid 79) (11R,12S,13E,15S,17R)-9-butyryloxy-11,15-dihydroxy-17,20-dimethyl-3-oxa-7-thiaprosta-8,13-dienoic acid 80) (11R,12S,13E,15S)-9-butyryloxy-11,15-dihydroxy-16-phenyl-17,18,19,20-tetranor-3-oxa-7-thiaprosta-8,13-dienoic acid 81) (2E,11R,12S,13E,15S)-9-butyryloxy-11,15-dihydroxy-7-thiaprosta-2,8,13-trienoic acid 82) (2E,11R,12S,13E,15S,17R)-9-butyryloxy-11,15-dihydroxy-17,20-dimethyl-7-thiaprosta-2,8,13-trienoic acid 83) (11R,12S,15S)-9-butyryloxy-11,15-dihydroxy-7-thia-8-prostenoic acid 84) (11R,12S,13E,15S)-9-(N-benzyloxycarbonylphenylalanyloxy)-11,15-dihydroxy-7-thiaprosta-8,13-dienoic acid 85) (11R,12S,13E,15S)-9-(5-(4-chlorophenoxy)-1,1-dimethylpentyryloxy)-11,15-dihydroxy-7-thiaprosta-8, 13-dienoic acid 86) (12S,13E,15S)-9-butyryloxy-15-hydroxy-7-thiaprosta-8,13-dienoic acid 87) (12S,13E,15S,17R)-9-butyryloxy-15-hydroxy-17,20-dimethyl-7-thiaprosta-8,13-dienoic acid 88) enantiomer of compound of 01) to 87)

89) methylester of compound of 01) to 88)

90) ethyl ester of compound of 01) to 88)

91) butylester of compound of 01) to 88)

92) allylester of compound of 01) to 88)

93) benzylester of compound of 01) to 88)

94) sodium salt of compound of 01) to 88)

95) a compound of the compound of 01) to 88) where the carboxylic acid at the 1-position is an amide 96) a compound of the compound of 01) to 88) where the carboxylic acid at the 1-position is dimethylamide 97) a compound of the compound of 01) to 88) where the carboxylic acid at the 1-position is diethylamide 98) an ether of the compound of 01) to 88) where the hydroxyl group (11-position, and 15-position or 16-position) is protected by a tert-butyldimethylsilyl group, and/or trimethylsilyl group, and/or 2-tetrahydropyranyl group Further, optical isomers of the hydroxyl group (15-position or 16-position) portion of the ω-chain of the compounds of 01) to 88) and all enantiomers of the same may be exemplified.

Further, the method of production of the 7-thiaprostaglandins according to the present invention of the above formula (I) is also included in the present invention. That is, the method produces the compound of the above formula (I) by reacting an organolithium compound or organotin compound having the formula (II):

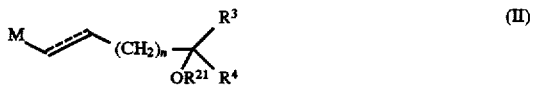

wherein, $R^3$, $R^4$, n, and the symbol $=$ are the same as defined above, and $R^{21}$ is a tri($C_1$ to $C_7$ hydrocarbon)silyl group or a group forming an acetal bond along with the oxygen atom of the hydroxyl group, M is a lithium atom or tri($C_1$ to $C_6$ hydrocarbon)stannyl group with an organocopper reagent generated from CuQ wherein, Q is a halogen atom, cyano group, phenylthio group, 1-pentynyl group, or 1-hexynyl group] with 2-organothio-2-cyclopentenones having the following formula (III):

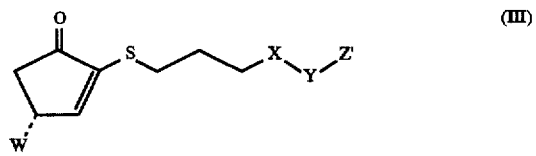

wherein, X—Y is the same as defined above, W' is a hydrogen atom, tri($C_1$ to $C_7$ hydrocarbon)siloxy group, or group forming an acetal bond, Z' is $CO_2R^{51}$, $R^{51}$ is a $C_1$ to $C_{10}$ straight or branched alkyl group, $C_2$ to $C_{10}$ straight or branched alkenyl group, substituted or unsubstituted phenyl group, substituted or unsubstituted $C_3$ to $C_{10}$ cycloalkyl group, or substituted or unsubstituted phenyl($C_1$ to $C_2$)alkyl group or their enantiomers or mixtures of any ratio of the same, followed by reacting with an acid anhydride or acid halide or mixed acid anhydride represented by, for example,

wherein, $R^1$ is the same as defined above or

wherein, $R^1$ is the same as defined above or the formula (IV):

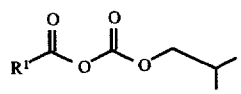

(IV)

wherein, $R^1$ is the same as defined above and, optionally, running a deprotection and/or a hydrolysis and/or a salt-forming reaction.

The process of synthesis of the 7-thiaprostaglandins according to the present invention is illustrated below:

In the conjugate addition reaction of the first step of the method according to the present invention (scheme 1), when a trivalent organic phosphorus compound, for example, trialkylphosphine (for example, triethylphosphine, tributylphosphine etc.), trialkylphosphite (for example, trimethylphosphite, triethylphosphite, triisobutylphosphite, tributylphosphite etc.), hexamethylphosphorus-triamide, triphenylphosphine, etc. are used along with the organocopper compound, the conjugate addition reaction proceeds smoothly. In particular, tributytphosphine and hexamethylphosphorus-triamide are preferably used.

The method of the present invention (scheme 1) is performed by reacting of the organolithium compound or organotin compound of the above formula (II), the organocopper compound generated from CuQ (Q is the same as defined above), and the 2-organolithio-2-cyclopentenones of the above formula (III) in the presence of an aprotonic inert organic solvent, followed by reacting with an acid anhydride, acid chloride, or mixed acid anhydride.

The 2-organolithio-2-cyclopentenones and organocopper compound are stoichiometrically equimolarly reacted, but normally 0.5 to 5.0 moles, preferably, 0.8 to 2.0 moles, particularly preferably, 1.0 to 1.5 moles of an organocopper compound are used, based on 1 mole of the 2-organolithio-2-cyclopentenones.

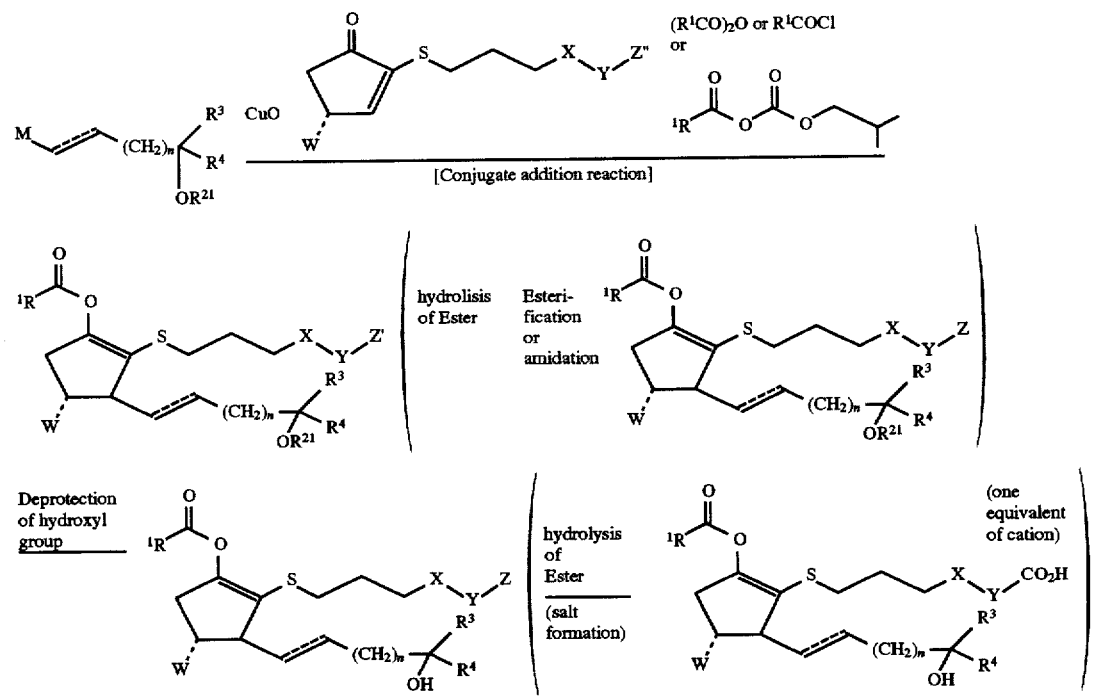

wherein, $R^1$, $R^{21}$, $R^3$, $R^4$, M, Q, W, W', X—Y, Z, Z', n, and the symbol $=$ are the same as defined above The 2-organolithio-2-cyclopentenones of the formula (III) can be obtained by known methods [Japanese Unexamined Patent Publication (Kokai) No. 60-185761].

In the scheme 1, when a racemate as the starting material is used, the synthesis proceeds stereospecifically as a mixture of the midway intermediate shown in the scheme 1 and their enantiomers, so if either of the compound of the above formula (II) or the above formula (IV) has optical activity, it is possible to isolate the individual stereo isomer as a pure product by separation at a suitable stage.

The reaction temperature range of the conjugate addition reaction of the 2-organolithio-2-cyclopentenones and organocopper compound is approximately −100° C. to 50° C., particularly preferably approximately −78° C. to 0° C.

The reaction time differs depending upon the reaction temperature, but normally it is sufficient if the reaction is performed at −78° C. to −20° C. for approximately 1 hour.

Further, the reaction intermediate obtained by the conjugate addition reaction between the 2-organolithio-2-cyclopentenones and organocopper compound and the acid anhydride, acid chloride, or mixed acid anhydride are stoichiometrically equimolarly reacted, but normally the reaction is performed with an excess of acid anhydride, acid chloride, or mixed acid anhydride. That is, the reaction is performed using 1.0 to 10.0 moles, preferably, 2.0 to 5.0 moles, of acid anhydride, acid chloride, or mixed acid anhydride based upon 1 mole of the 2-organolithio-2-cyclopentenones.

The reaction temperature of the reaction of the reaction intermediate obtained in the conjugate addition reaction of the 2-organolithio-2-cyclopentenones and organocopper compound with the acid anhydride, acid chloride, or mixed acid anhydride is approximately −30° C. to 50° C., particularly preferably approximately −20° C. to 30° C. The reaction time differs depending upon the reaction temperature, but normally it is sufficient if the reaction is performed at 0° C. to 20° C. for approximately 15 minutes.

The reaction is performed in the presence of an organic solvent. An inert aprotonic organic solvent which is liquid at the reaction temperature and does not react with the reaction reagents may be used. As the aprotonic inert organic solvent, for example, pentane, hexane, heptane, cyclohexane or other saturated hydrocarbons, benzene, toluene, xylene or other aromatic hydrocarbons, diethyl ether, tetrahydrofuran, dioxane, dimethoxyethane, diethyleneglycol dimethylether, or other ether type solvents and also hexamethylphospholic amide (HMP), N,N-dimethylformamide (DMF), N,N-dimethylacetoamide (DMA), dimethylsulfoxide (DMSO), sulfolane, N-methylpyrrolidone, and other so-called aprotonic polar solvents may be mentioned. Mixtures of two or more types of solvents may also be used. Further, as the protonic inert organic solvent, the same inert solvent used for production of the organocopper compound, that is, in this case, the reaction may be performed by adding 2-organolithio-2-cyclopentenones to the reaction system for producing the organocopper compound. The amount of the organic solvent used should be an amount sufficient for enabling the reaction to proceed smoothly. Normally, 1 to 100-fold volumes of the starting materials, preferably, 2 to 20-fold volumes may be used.

The trivalent organic phosphorus compound may be made present at the time of the generation of the organocopper compound mentioned above. Also, the reaction may be performed adding the 2-organolithio-2-cyclopentenones into the system.

Thus, among the compounds of the formula (I), those having a protected hydroxyl group and a Z of an ester can be obtained. The method of production of the present invention uses a reaction which proceeds stereospecifically, so a compound having the configuration of the formula (I) is obtained from a starting material having the configuration of the above formula (III) and an enantiomer of the formula (I) of the formula (I)ent is obtained from the enantiomer of the above formula (III).

After the reaction, the resultant product is separated from the reaction solution and refined by ordinary means. For example, extraction, washing, chromatography, or combinations of the same may be performed.

Further, the thus obtained compound with the protected hydroxyl group and the Z of an ester may, in accordance with need, be subjected to removal of the protecting group, hydrolysis, or a salt-forming reaction.

When Z is an allylester ($R^{51}$=allyl), a hydrolysis reaction using a palladium catalyst and formic acid or formic acid salt may be used to convert the allylester to a carboxylic acid ($R^{51}$=H). The carboxylic acid thus obtained may further be converted to another substituent by esterification or amidation.

In the hydrolysis reaction of an allylester using a palladium catalyst according to the present invention, as the palladium catalyst, a zero-valent and bivalent complex may be used. For example, tris(dibenzylideneacetone) dipalladium (0), bis[1,2-bis(diphenylphosphino)ethane] palladium (0), tetrakistriphenylphosphine palladium (II), palladium acetate, bistriphenylphosphine palladium (II) acetate, etc. may be mentioned.

To reduce the amount of the palladium complex necessary for ending the reaction, in some cases a ligand of the phosphine etc. may be added to the reaction system. In particular, with a palladium complex with no phosphine ligand in the complex, such as tris(dibenzylideneacetone) dipalladium (0) or palladium acetate, in many cases, the reaction is performed adding a ligand to the reaction system. As the ligand added, triphenylphosphine, diphenylphosphino-ethane, tributylphosphine, triethylphosphine, triethylphosphite, etc. may be mentioned. The amount of the palladium complex used for the reaction is 0.1 to 50 mol % of the allylester of the substrate. When adding a ligand, the amount added is approximately 0.2 to 8 equivalents based upon the palladium.

The hydrolysis reaction of the allylester is performed in the presence of an organic solvent. An inert aprotonic organic solvent which is liquid at the reaction temperature and does not react with the reaction reagents may be used. As the aprotonic inert organic solvent, for example, pentane, hexane, heptane, cyclohexane, or other saturated hydrocarbons, benzene, toluene, xylene, or other aromatic hydrocarbon, diethyl ether, tetrahydrofuran, dioxane, dimethoxyethane, diethyleneglycol dimethylether, or other ether type solvents, and also hexamethylphospholic amide (HMP), N,N-dimethylformamide (DMF), N,N-dimethylacetoamide (DMA), dimethylsulfoxide (DMSO), sulfolane, N-methylpyrrolidone, and other so-called aprotonic polar solvents may be mentioned. Mixtures of two or more types of solvents may also be used. The amount of the organic solvent used should be an amount sufficient for enabling the reaction to proceed smoothly. Normally a 1 to 100-fold volume of the material, preferably a 2 to 20-fold volume may be used.

The hydrolysis reaction of the allylester uses formic acid as the hydrogen source. While stoichiometrically an equimolar amount with respect to the allylester of the substrate is sufficient, in practice 0.5 to 10.0 equivalents of formic acid are used. Preferably, 1.0 to 5.0 equivalents are used. In actual experiments, when formic acid was used, commercially available ammonium salts were used as they were or use was made of formic acid dissolved in a solvent to which triethylamine or other base was added to control the acidity. The amount of the base used is basically an equimolar amount with the formic acid so that the reaction system becomes neutral, but considering the acid resistance and base resistance of the reaction substrate, the conditions do not necessarily have to be neutral so long as the compound is not decomposed.

The reaction temperature of the hydrolysis reaction of the allylester is approximately 0° to 100° C., preferably 15° to 70° C.

Thus, among the compounds of the formula (I), those having a protected hydroxyl group and a Z of a carboxylic acid can be obtained.

After the reaction, the resultant product is separated from the reaction solution and purified by means such as removal of the catalyst by Florisil or Celite filtration, extraction, washing, and chromatography.

The compound having a Z of a carboxylic acid obtained here may further, optionally, be treated to form ester or amido of the carboxylic acid, or to remove the protection of the hydroxyl groups, etc.

The esterification and amidation of the carboxylic acid portion may be performed using ordinary chemical reactions.

The removal of the protecting groups (W' and/or $R^{21}$) of the hydroxyl group of the compound is suitably performed, when the protecting group forms an acetal bond with the oxygen atom of the hydroxyl group, by, for example, using acetic acid, a pyridinium p-toluene sulfonate, or a positive ion exchange resin as a catalyst and using, for example, water, tetrahydrofuran, dioxane, acetone, acetonitrile, etc. as a reaction solvent. The reaction is normally performed at a temperature range of approximately −78° C. to 50° C. for 10 minutes to 3 days. Further, when the protecting group is a tri($C_1$ to C7 hydrocarbon)silyl group, the reaction is performed using, for example, acetic acid, a pyridinium p-toluene sulfonate, tetrabutylammonium fluoride, cesium fluoride, hydrogen fluoride, hydrogen fluoride-pyridine, etc. as a catalyst in the reaction solution mentioned above at the same temperature for the same amount of time.

In the case of a compound with a higher water solubility after removal of the protecting group of the hydroxyl group, the hydrolysis reaction of the ester of the compound where Z is an ester may be performed, for example, using lipase, estrase, and other enzymes in water or a water-containing solvent at a temperature range of approximately −10° C. to 60° C. for 10 minutes to 24 hours. However, the enol ester at the 9-position is hydrolyzed under these conditions, so it is desirable to frequently check the progress of the reaction and, when the enol ester of the 9-position starts to be hydrolyzed, stop the reaction without waiting for the removal of the protecting group ($R^5$) of the 1-position carboxyl group to be completed so as to obtain the desired 7-thiaprostaglandins. Note that, as mentioned above, when the Z is an allylester ($R^{51}$=allyl), it is possible to remove the protecting group ($R^{51}$) by a hydrolysis reaction using a palladium catalyst even with a compound where the protecting group of the hydroxyl group has been removed.

According to the present invention, the compound having the carboxyl group obtained by the hydrolysis reaction in the above way may then, if desired, further be subjected to a salt-forming reaction to obtain a corresponding carboxylic acid salt. The salt-forming reaction is performed by causing a neutralization reaction by an ordinary method with potassium hydroxide, sodium hydroxide, sodium carbonate, or other basic compounds or ammonia, trimethylamine, monoethanol amine, or morpholine in a substantially equal amount as the carboxylic acid.

Further, among the 7-thiaprostaglandins according to the present invention having the above formula (I), the compound where n is 0, $R^2$ and $R^3$ are hydrogen atoms, and the symbol ⚌ is a double bond can be produced by a method different from the above mentioned method of production (scheme 1). This method of production is also included in the present invention. This method of production is to synthesize a common intermediate including the ω-chain up to the 14-position in advance and finally introducing the ω-chain portion including the hydroxyl group from the 15-position on.

This is a method for synthesizing enol ester derivatives of prostaglandins $E_1$ by suitably combining 1) a reaction making just one of the two stannyls of the trans-1,2-bis(tributylstannyl)ethylene a cuprate, by using higher order cyanocuprates and causing 1,4-conjugate addition,
2) a reaction for synthesizing enol ester derivatives of prostaglandins by quenching by adding an acid anhydride or acid chloride to the reaction mixture of the enolate anions after the 1,4-conjugate addition,
3) a reaction for deriving a haloolefin from the stannyl group of the vinylstannane using a halogen while maintaining the configuration, and
4) a reaction for coupling the alkenyl halide and aldehyde using chromium chloride (II) ($CrCl_2$). In particular, this method is useful for the conversion of the ω-chain of the prostaglandins. Note that this method of production may also be used for the synthesis of prostaglandins $E_1$ with 7-positions of methylene (A=—$CH_2$—). That is, it is a method of causing a reaction of the trans-1,2-bis (trialkylstannyl)ethylene or trans-1,2-bis (triphenylstannyl)ethylene of the following formula (v):

 (V)

wherein, P is a $C_1$ to $C_6$ straight or branched alkyl group or phenyl group and an organocopper compound generated from

wherein, Q is a halogen atom, cyano group, phenylthio group, 1-pentynyl group, or 1-hexynyl group and a $C_1$ to $C_4$ straight or branched alkyllithium compound and 2-organolithio-2-cyclopentenones of the following formula (VI):

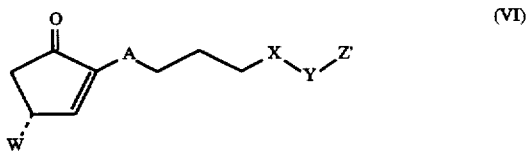 (VI)

wherein, A is a bivalent sulfur atom or methylene, W', X—Y, and Z' are the same as defined above or their enantiomers or mixtures of any ratio of the same, then causing a reaction with an acid anhydride or acid halide of

wherein, $R^1$ is the same as defined above or

wherein, $R^1$ is the same as defined above so as to synthesize the vinylstannyl compound of the formula (VII):

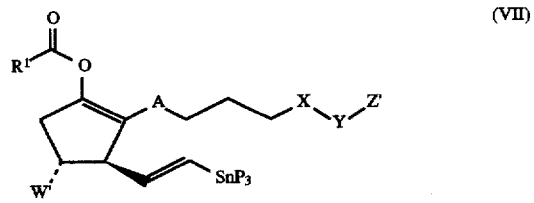 (VII)

wherein, A, $R^1$, P, W', X—Y, and Z' are the same as defined above, then followed by reacting this compound with the halogen molecule of

wherein, B is an iodine atom or bromine atom to derive the haloolefin compound having the formula (VIII):

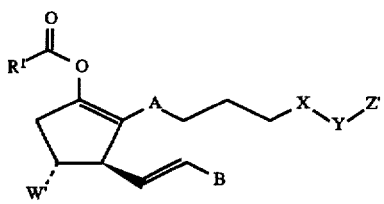  (VIII)

wherein, A, B, R¹, W', X—Y, and Z' are the same as defined above, then followed by reacting this compound with the aldehydes having the formula (IX):

  (IX)

wherein, R⁴ is the same as defined above in the presence of CrCh₂, and, in accordance with need, removing the protecting group and/or performing hydrolysis and/or a salt-forming reaction so as to produce the prostaglandins having the formula (X):

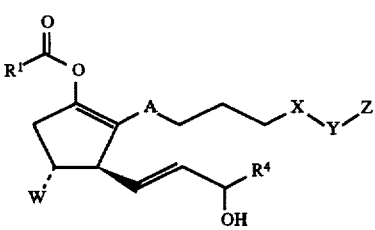  (X)

wherein, A, R¹, R⁴, W, X—Y, and Z are the same as defined above.

The process for synthesis of the prostaglandins according to the present invention is illustrated below:

Scheme 2

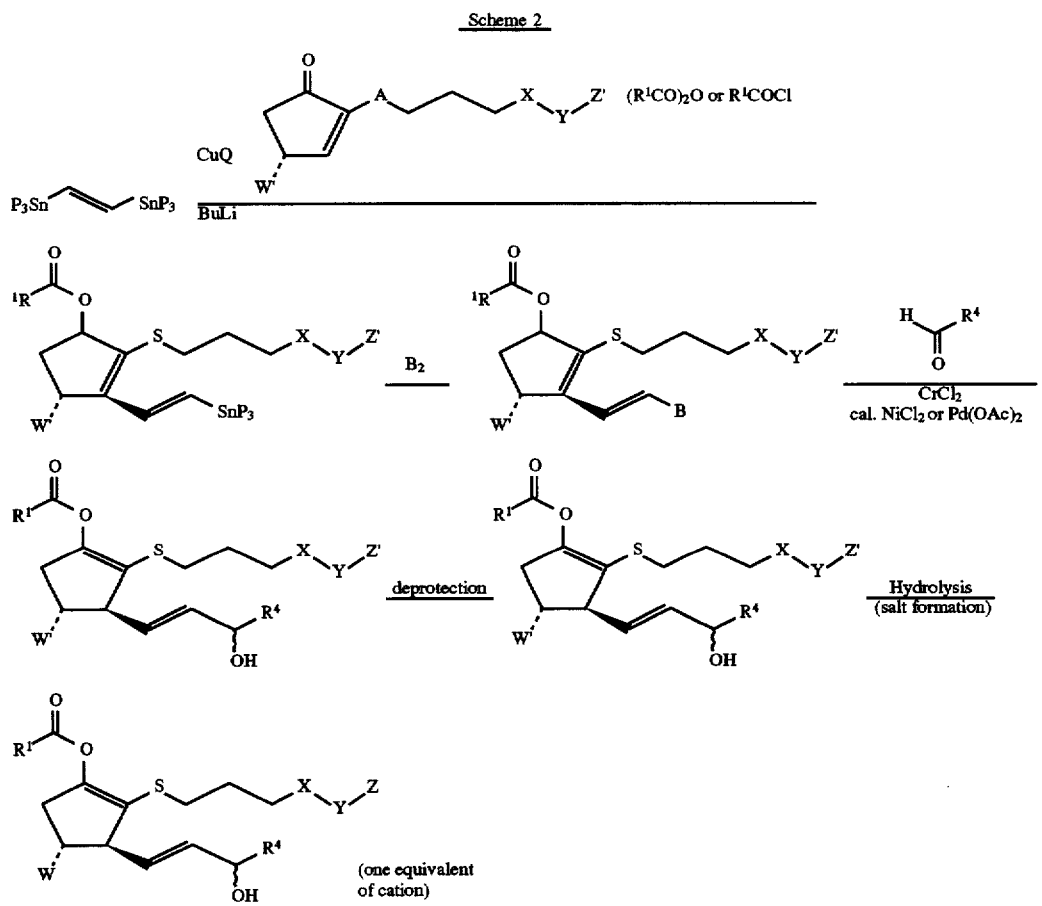

wherein, A, R¹, R⁴, P, Q, W, W', X—Y, Z, and Z' are the same as defined above.

In the method of synthesis of this scheme 2, the P in the trans-1,2-bis(trialkylstannyl)ethylene or trans-1,2-bis (triphenylstannyl)ethylene of the above formula (V) is a $C_1$ to $C_6$ straight or branched alkyl group or phenyl group. As preferable examples of the $C_1$ to $C_6$ straight or branched alkyl group, a methyl group, ethyl group, propyl group, isopropyl group, butyl group, isobutyl group, sec-butyl group, tert-butyl group, etc. may be mentioned. Among these, a butyl group is most preferred.

The Q in CuQ of the above formula is a halogen atom, cyano group, phenylthio group, 1-pentynyl group, or 1-hexynyl group. Among these, as Q, a cyano group is preferred. A $C_1$ to $C_4$ straight or branched alkyllithium compound means, for example, n-butyllithium, tert-butyllithium, etc. Normally, 1.0 to 3.0 equivalents based upon CuQ are used to prepare the organocopper reagent. In particular, when preparing higher order cyanocupretes using CuCN, 1.8 to 2.2 equivalents is preferably used. On the other hand, it is also possible to cause a reaction of 0.3 to 0.6 equivalent, preferably, 0.5 equivalent of an alkyllithium compound with the bisstannylethylene to produce a monolithio-compound, followed by reacting 0.5 to 2.0 equivalents of CuQ, preferably 1.0 to 1.3 equivalents, to prepare an organocyanocuprete for use. The organocyanocuprete is normally used in a temperature range of approximately $-100°$ C. to $50°$ C., particularly preferably, approximately $-78°$ C. to $30°$ C. The reaction time differs according to the reaction temperature, but normally it is sufficient if the reaction is performed at $-78°$ C. to $30°$ C. for approximately 2 hours.

The first step of the method of production according to the present invention (scheme 2) is performed by causing a reaction of the organocyanocuprete generated from the above organolithium compound, CuQ (Q is the same as defined above), the trans-1,2-bis(trialkylstannyl)ethylene or trans-1,2-bis(triphenylstannyl)ethylene, with the 2-substituted-2-cyclopentenones of the above formula (VI) in the presence of an aprotonic inert organic solvent, followed by reacting with an acid anhydride or acid chloride.

Note that the method of synthesis of the compound of the formula (VI) is, for example, described in Tanaka et al., Chem. Pharm. Bull. 3,3, 2356 to 2385 (1985).

In the above formula (VI), A is a bivalent sulfur atom or methylene group. Preferably, A is a bivalent sulfur atom.

In the conjugate addition reaction of the first step of the method according to the present invention (scheme 2), when a trivalent organophosphorus compound, for example, trialkylphosphine (for example, triethylphosphine, tributylphosphine etc.), trialkylphosphite (for example, trimethylphosphite, triethylphosphite, triisobutylphosphite, tributylphosphite, etc.), hexamethylphosphorustriamide, triphenylphosphine, etc. are used, along with the organocopper compound, the conjugate addition reaction sometimes proceeds smoothly. In particular, tributylphosphine and hexamethylphosphorustriamide are suitably used.

The 2-substituted-2-cyclopentenones and organocopper compound of the above formula (VI) are stoichiometrically equimolarly reacted, but normally 0.5 to 5.0 moles of the organocopper compound, preferably 0.8 to 2.0 moles, particularly preferably 1.0 to 1.5 moles are used based upon 1 mole of the 2-substituted-2-cyclopentenones.

The reaction temperature of the conjugate addition reaction of the 2-substituted-2-cyclopentenones and organocopper compound used is a temperature range of approximately $-100°$ C. to $50°$ C., particularly preferably approximately $-78°$ C. to $0°$ C. The reaction time differs according to the reaction temperature, but normally it is sufficient if the reaction is performed at $-78°$ C. to $-20°$ C. for approximately 1 hour.

Further, the reaction intermediate obtained in the conjugate addition reaction of the 2-substituted-2-cyclopentenones and organocopper compound is stoichiometrically equimolarly reacted with the acid anhydride or acid chloride, but normally the reaction is performed with an excess of acid anhydride or acid chloride. That is, the reaction is performed using 1.0 to 10.0 equivalents, preferably, 2.0 to 5.0 equivalents, of acid anhydride or acid chloride based upon the 2-substituted-2-cyclopentenones.

The reaction temperature of the reaction of the reaction intermediate obtained by the conjugate addition reaction between the 2-substituted-2-cyclopentenones and organocopper compound with the acid anhydride or acid chloride is a temperature range of approximately $-30°$ C. to $50°$ C., particularly preferably approximately $-20°$ C. to $30°$ C. The reaction time differs according to the reaction temperature, but normally it is sufficient if the reaction is performed at $0°$ C. to $20°$ C. for approximately 15 minutes.

The first step of the method of synthesis of scheme 2 is performed in the presence of an organic solvent. An inert aprotonic organic solvent which is liquid at the reaction temperature and will not react with the reaction reagents may be used.

As the aprotonic inert organic solvent, for example, pentane, hexane, heptane, cyclohexane or other saturated hydrocarbons, benzene, toluene, xylene or other aromatic hydrocarbons, diethyl ether, tetrahydrofuran, dioxane, dimethoxyethane, diethyleneglycol dimethylether, or other ether type solvents and also hexamethylphospholic amide (HMP), N,N-dimethylformamide (DMF), N,N-dimethylacetoamide (DMA), dimethylsulfoxide (DMSO), sulfolane, N-methylpyrrolidone, or other so-called aprotonic polar solvents may be mentioned. Mixtures of two or more types of solvents may also be used. Further, as the aprotonic inert organic solvent, it is possible to use as is the inert solvent used for the production of the organocopper compound. That is, in this case, the reaction may be performed by adding 2-substituted-2-cyclopentenones to the reaction system for producing the organocopper compound. The amount of the organic solvent used should be an amount sufficient for enabling the reaction to proceed smoothly. Normally, a 1 to 100-fold volume of the material, preferably a 2 to 20-fold volume is used.

The trivalent organophosphorus compound may be made to be present at the time of preparation of the organocopper compound and a reaction may be caused by adding 2-substituted-2-cyclopentenones to the reaction system.

Thus, the compound of the formula (VII), that is, a vinylstannane compound with a protected hydroxyl group and a Z of an ester is obtained. The method of production of the present invention uses a reaction which proceeds stereospecifically, so a compound having the configuration of the formula (VII) is obtained from a starting material having the configuration of the above formula (VI) and an enantiomer of the formula (VII) is obtained from the enantiomer of the above formula (VI).

After the reaction, the resultant product is separated from the reaction solution and purified by ordinary means. For example, extraction, washing, chromatography, or combinations of the same may be performed.

The second step of the method of production of the present invention (scheme 2) is performed by causing a reaction of the thus obtained vinylstannane compound of the above formula (VII) with a protected hydroxyl group and a Z of an ester with 0.5 to 1.5 equivalents, preferably, 1.0 equivalent of the halogen molecule of $B_2$ in the presence of a solvent to give the haloolefin of the above formula (VIII). In the present method of production, $B_2$ is an iodine atom or bromine. Among these, an iodine atom is most preferred as B. As the solvent of this reaction, for example, pentane, hexane, heptane, cyclohexane or other saturated hydrocarbons, benzene, toluene, xylene or other aromatic hydrocarbon, diethyl ether, tetrahydrofuran, dioxane, dimethoxyethane, diethyleneglycol dimethylether, or other ether type solvents and also hexamethylphospholic amide (HMP), N,N-dimethylformamide (DMF), N,N-dimethylacetoamide (DMA), dimethylsulfoxide (DMSO), sulfolane, N-methylpyrrolidone, and other so-called aprotonic polar solvents, methanol, ethanol, isopropylalcohol or other alcohol type solvents, acetone, methylethylketone, or other ketone type solvents, and methylene chloride chloroform and other halogen type solvents may be mentioned. Mixtures of two or more types of solvents may also be used. The amount of the organic solvent used should be an amount sufficient for enabling the reaction to proceed smoothly. Normally a 1 to 100-fold volume of the material, preferably a 2 to 20-fold volume is used. After the reaction, the resultant product is separated from the reaction solution and purified by ordinary means. For example, extraction, washing, chromatography, or combinations of the same may be performed.

Thus, the compound of the formula (VIII), that is, an alkenyl halide with a protected hydroxyl group and a Z of an ester is obtained. The method of production of the present invention uses a reaction which proceeds while holding the configuration, so the compound of the configuration of the above formula (VIII) is obtained from a starting material having the configuration of the above formula (VII) and an enantiomer of the formula (VIII) is obtained from the enantiomer of the above formula (VII).

The third step of the method of production of the present invention (scheme 2) is performed by a Grignard type addition reaction of the alkenyl halide of the above formula (VIII) obtained here to the aldehydes of the above formula (IX) using $CrCl_2$, to derive the prostaglandins with a protected hydroxyl group and a Z of an ester of the above formula (X). Note that at the time of this addition reaction, if a $NiCl_2$ or $Pd(OAc)_2$ catalyst is added, the reaction is sometimes promoted.

The coupling reaction of the alkenyl halide and aldehyde in the present method of production (scheme 2) uses 1.0 to 10.0 equivalents, preferably, approximately 5.0 equivalents of chromium(II) chloride ($CrCl_2$). Further, use of 0.01 to 1 mol % of $NiCl_2$ or $Pd(OAc)_2$ as a catalyst is preferable.

As the reaction solvent, hexamethylphospholicamide (HMP), N,N-dimethylformamide (DMF), N,N-dimethylacetoamide (DMA), dimethylsulfoxide (DMSO), sulfolane, N-methylpyrrolidone, or another so-called aprotonic polar solvents may be used. Mixtures of two or more types of solvents may also be used. Among these, N,N-dimethylacetoamide (DMA) and dimethylsulfoxide (DMSO) are preferred. The amount of the organic solvent used should be an amount sufficient for enabling the reaction to proceed smoothly. Normally a 1 to 100-fold volume of the material, preferably a 2 to 20-fold volume, is used. The reaction temperature of the present coupling reaction used is approximately −30° C. to 50° C., particularly preferably a temperature of approximately −20° C. to 30° C. The reaction time differs according to the reaction temperature, but normally it is sufficient if the reaction is performed at 0° C. to 30° C. for approximately 3 hours. After the reaction, the resultant product is separated from the reaction solution and purified by ordinary means. For example, extraction, washing, chromatography or combinations of the same may be performed.

Thus, the compounds of the formula (X), that is, prostaglandins with a protected hydroxyl group and a Z of an ester are obtained.

The compounds of the formula (X) may, optionally, be subjected to removal of the protecting group, hydrolysis, or a salt-forming reaction.

The removal of the protecting group, hydrolysis, or salt-forming reaction used here may be performed by the same method as the method of production (scheme 1) of the above-mentioned compound (I).

In the method of the present invention (scheme 2), if a racemic mixture is used as the starting material, the synthesis proceeds stereospecifically as a mixture of the midway intermediate shown in the scheme and their enantiomers. If the compound of the formula (VI) has optical activity, it is possible to isolate the individual stereo isomers as pure products by separation at a suitable stage.

Further, the compounds of the formulas (VII), (VIII), and (IX) have configurations derived from compounds having the configurations of natural prostaglandin, so these compounds are particularly useful stereo isomers, but in the present invention, enantiomers or any mixtures of the same are also included in the present invention. The carbon atom where the hydroxyl group and $R^4$ bond (15-position) is an asymmetric carbon, so there are two types of stereo isomers derived from the asymmetric carbon. When an optically active substance (W is not equal to H) is used for the starting material (VI), these two types of stereo isomers can be easily obtained as pure products, after removal of the protecting group of the hydroxyl group at the 11-position, by silica gel column chromatography or other separation and purifying methods.

INDUSTRIAL APPLICABILITY

The compounds according to the present invention comprised 7-thiaprostaglandins, wherein the $R^2$ is a hydrogen atom and the W is a hydroxyl group, their enantiomers, mixtures of any ratio of the same, and drugs containing their pharmaceutically acceptable salts as active ingredients have the activity of inhibiting the cell migration induced by chemokines, for example, MCP-1/MCAF and are useful as agents for prevention and treatment of restenosis or reocclusion occurring after trauma to the intima of arteries in angioplasty etc., stenosis or occlusion caused by progression of atherosclerosis at the coronary artery, carotid artery, etc., and accumulation of blood monocytes into the lesions.

Further, the 7-thiaprostaglandins of the present invention have the physiological action typical of prostaglandins, that is, an activity inhibiting the aggregation of platelets, and are useful as agents for the prevention and treatment of thrombosis, cardiac infarction, angia, etc. which prostaglandins have traditionally been considered useful for.

EXAMPLES

Example 1

Synthesis of methyl(11R,12S,13E,15S,17R)-9-butyryloxy-11,15-bis(tert-butyldimethylsiloxy)-17,20-dimethyl-7-thiaprosta-8,13-dienoate (R$^1$=Pr, R$^2$=$^t$BuMe$_2$Si, R$^3$=H, R$^4$=2-Me-hexyl, W=$^t$BuMe$_2$SiO, X—Y=CH$_2$—CH$_2$, Z=CO$_2$Me, n=0, ═=trans-CH═CH)

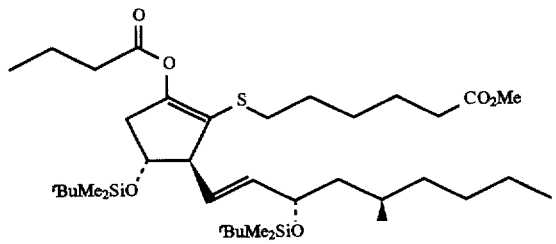

An ether (3 ml) solution of (1E,3S,5R)-1-iodo-3-(tert-butyldimethylsiloxy)-5-methyl-1-nonene (476 mg, 1.2 mmol) was cooled to −78° C., then tert-butyllithium (1.54 mol/l, 1.56 ml, 2.4 mmol) was added. The mixture was stirred as is at −78° C. for two hours. Further, an ether (6 ml) solution of 174 mg of 1-hexynylcopper and hexamethylphosphorous triamide (436 µl) was added thereto. The solution was further stirred as is at −78° C. for one hour to produce a copper reagent.

A tetrahydrofuran (20 ml) solution of (4R)-tert-butyldimethylsiloxy-2-(5-methoxycarbonylpentylthio)-2-cyclopenten-1-on (373 mg, 1 mmol) was dropwise added to the copper reagent thus obtained. This reaction mixture was stirred as is at −78° C. for 15 minutes, then the reaction temperature was raised and the mixture was stirred at −40° to −30° C. for one hour. Further, butyric anhydride (441 µl) was added at 0° C. and the mixture was stirred for 15 minutes while raising the reaction temperature to room temperature. The reaction solution was poured into saturated ammonium sulfate (40 ml), the organic layer was separated, the aqueous layer was extracted with ether, the extract was combined with the organic layer, then the solution was dried over anhydrous magnesium sulfate. This solution was concentrated under reduced pressure, then was purified by silica gel column chromatography (5 to 10% ethyl acetate/hexane) to obtain methyl(11R,12S,13E,15S,17R)-9-butyryloxy-11,15-bis(tert-butyldimethylsiloxy)-17,20-dimethyl-7-thiaprosta-8,13-dienoate (428 mg, 60%).

$^1$H-NMR (270 MHz, δppm, CDCl$_3$) 0.04 (s), 0.05 (s) ..... 12H 0.87 (s, 9H) 0.8–1.0 (m, 6H) 0.89 (s, 9H) 1.00 (t, J=7.3 Hz, 3H) 1.0–1.8 (m, 17H) 2.30 (t, J=7.6 Hz, 2H) 2.42 (t, J=7.3 Hz, 2H) 2.3–2.7 (m, 3H) 2.92 (dd, J=16.3 & 6.8 Hz, 1H) 3.12 (d, J=7.9 Hz, 1H) 3.66 (s, 3H) 4.1–4.2 (m, 2H) 5.43 (dd, J=15.5 & 8.6 Hz, 1H) 5.62 (dd, J=15.3 & 6.1 Hz, 1H)

Example 2

Synthesis of methyl(11R,12S,13E,15S,17R)-9-butyryloxy-11,15-dihydroxy-17,20-dimethyl-7-thiaprosta-8,13-dienoate (R$^1$=Pr, R$^2$=H, R$^3$=H, R$^4$=2-Me-hexyl, W=OH, X—Y=CH$_2$—CH$_2$, Z=CO$_2$Me, n=0, ═=trans-CH═CH)

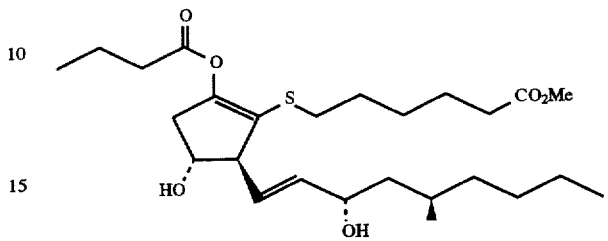

A hydrogen fluoride-pyridine solution (0.3 ml) was added to an ice-cooled acetonitrile (3 ml) and pyridine (0.1 ml) solution. A pyridine (50 µl) solution of methyl(11R,12S,13E,15S,17R)-9-butyryloxy-11,15-bis(tert-butyldimethylsiloxyl)-17,20-dimethyl-7-thiaprosta-8,13-dienoate (214 mg) was added thereto. The ice bath was removed and the mixture was stirred for four hours while returning the temperature to room temperature. The reaction solution was poured into a mixture of ethyl acetate and saturated sodium hydrogen carbonate. The desired substance was extracted from the mixture by ethyl acetate. The extract was washed with saturated sodium chloride solution then was dried over anhydrous sodium sulfate. This solution was concentrated under reduced pressure, then was purified by silica gel column chromatography (40 to 50% ethyl acetate/hexane) to obtain methyl(11R,12S,13E,15S,17R)-9-butyryloxy-11,15-dihydroxy-17,20-dimethyl-7-thiaprosta-8,13-dienoate (119 mg, 82%).

$^1$H-NMR (270 MHz, δppm, CDCl$_3$) 0.8–1.0 (m, 6H) 1.00 (t, J=7.4 Hz, 3H) 1.0–1.8 (m, 17H) 2.30 (t, J=7.4 Hz, 2H) 2.43 (t, J=7.4 Hz, 2H) 2.3–2.7 (m, 3H) 2.89 (ddd, J=16.5 & 6.9 & 1.3 Hz, 1H) 3.20 (dd, J=8.1 & 3.5 Hz, 1H) 3.67 (s, 3H) 4.1–4.3 (m, 2H) 5.55 (dd, J=15.3 & 8.1 Hz, 1H) 5.68 (dd, J=15.3 & 6.4 Hz, 1H)

Example 3

Synthesis of (11R,12S,13E,15S,17R)-9-butyloxy-11,15-dihydroxy-17,20-dimethyl-7-thiaprosta-8,13-dienoic acid (R$^1$=Pr, R$^2$=H, R$^3$=H, R$^4$=2-Me-hexyl, W=OH, X—Y=CH$_2$—CH$_2$, Z=CO$_2$H, n=0, ═=trans-CH═CH)

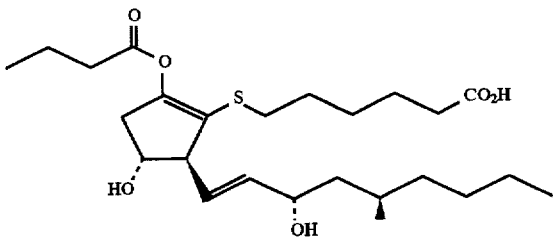

Methyl(11R,12S,13E,15S,17S)-9-butyloxy-11,15-dihydroxy-17,20-dimethyl-7-thiaprosta-8,13-dienoate (51 mg, 0.11 mmol) was dissolved in acetone (1 ml). To this solution was added a pH 8 phosphate buffer (10 ml). Further esterase (from porcine liver made by Sigma Co., 114 µl) was added and the mixture was stirred at room temperature for five hours. Further in a state with methyl ester remaining, the reaction solution was ice cooled, was made pH 4 by dilute hydrochloric acid, and was saturated by ammonium sulfate. The mixture was extracted by ethyl acetate, the extract was dried, then was concentrated under reduced pressure. The concentrate was purified by thin layer chromatography (developing solvent: ethyl acetate, Rf=0.2) to obtain (11R, 12S,13E,15S,17S)-9-butyloxy-11,15-dihydroxy-17,20-dimethyl-7-thiaprosta-8,13-dienoic acid (7 mg, 14%).

$^1$H-NMR (270 MHz, δppm, CDCl$_3$) 0.8–1.0 (m, 6H) 1.00 (t, J=7.4 Hz, 3H) 1.0–1.8 (m, 17H) 2.30 (t, J=7.4 Hz, 2H) 2.43 (t, J=7.4 Hz, 2H) 2.3–2.7 (m, 3H) 2.89 (ddd, J=16.5 & 6.9 & 1.3 Hz, 1H) 3.20 (dd, J=8.1 & 3.5 Hz, 1H) 4.1–4.3 (m, 2H) 5.55 (dd, J=15.3 & 8.1 Hz, 1H) 5.68 (dd, J=15.3 & 6.4 Hz, 1H)

Example 4

Synthesis of methyl(11R,12S,13E,15S,17R)-9-acetoxy-11,15-bis(tert-tubyldimethylsiloxy)-17,20-dimethyl-7-thiaprosta-8,13-dienoate (R$^1$=Me, R$^2$= $^t$BuMe$_2$Si, R$^3$=H, R$^4$=2-Me-hexyl, W=$^t$BuMe$_2$SiO, X—Y=CH$_2$—CH$_2$, Z=CO$_2$Me, n=0, =trans-CH=CH)

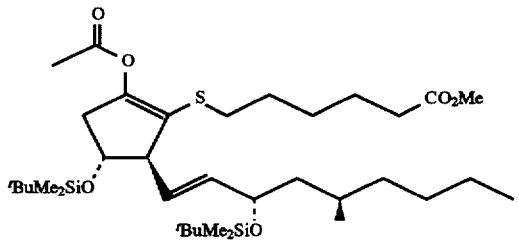

Using as the materials and reagents (1E,3S,5R)-1-iodo-3-(tert-butyldimethylsiloxy)-5-methyl-1-nonene (476 mg, 1.2 mmol), tert-butyllithium (1.54 mol/l, 1.56 ml, 2.4 mmol), 174 mg of 1-hexynylcopper, hexamethylphosphorous triamide (436 μl), (4R)-1-tert-butyldimethylsiloxy-2-(5-methoxycarbonylpentylthio)-2-cyclopenten-1-one (373 mg, 1 mmol), and acetic anhydride (255 μl), the same procedure was performed as in Example 1 to obtain methyl (11R,12S,13E,15S,17R)-9-acetoxy-11,15-bis(tert-butyldimethylsiloxy)-17,20-dimethyl-7-thiaprosta-8,13-dienoate (484 mg, 71%).

$^1$H-NMR (270 MHz, δppm, CDCl$_3$) 0.02 (s), 0.03 (s) ...... 12H 0.8–0.9 (m, 6H) 0.86 (s, 9H) 0.87 (s, 9H) 1.0–1.7 (m, 15H) 2.16 (s, 3H) 2.28 (t, J=7.4 Hz, 2H) 2.3–2.7 (m, 3H) 2.91 (ddd, J=1.4 & 6.7 & 16.4 Hz, 1H) 3.10 (d, J=6.6 Hz, 1H) 3.64 (s, 3H) 4.0–4.2 (m, 2H) 5.41 (dd, J=8.6 & 15.8 Hz, 1H) 5.60 (dd, J=6.1 & 15.3 Hz, 1H)

Example 5

Synthesis of methyl(11R,12S,13E,15S,17R)-9-acetoxy-11,15-dihydroxy-17,20-dimethyl-7-thiaprosta-8,13-dienoate (R$^1$=Me, R$^2$H, R$^3$H, R$^4$=2-Me-hexyl, W=OH, X—Y=CH$_2$—CH$_2$, Z=CO$_2$Me, n=0, =trans-CH=CH)

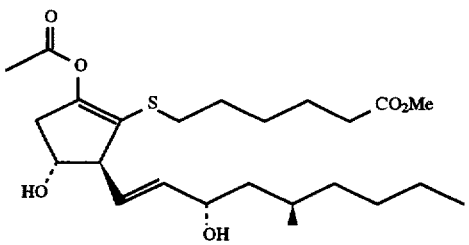

Using as the material and reagent a hydrogen fluoride-pyridine solution (0.6 ml) and methyl(11R,12S,13E,15S,17R)-9-acetoxy-11,15-bis(tert-butyldimethylsiloxy)-17,20-dimethyl-7-thiaprosta-8,13-dienoate (484 mg), the same procedure as in Example 2 was performed to obtain methyl (11R,12S,13E,15S,17R)-9-acetoxy-11,15-dihydroxy-17,20-dimethyl-7-thiaprosta-8,13-dienoate (179 mg, 56%).

$^1$H-NMR (270 MHz, δppm, CDCl$_3$) 0.8–1.0 (m, 6H) 1.1–1.7 (m, 15H) 2.19 (s, 3H) 2.31 (t, J=7.4 Hz, 2H) 2.4–2.8 (m, 3H) 2.91 (ddd, J=1.1 & 6.8 & 16.4 Hz, 1H) 3.20 (dd, J=3.3 & 8.3 Hz, 1H) 3.67 (s, 3H) 4.1–4.3 (m, 2H) 5.56 (dd, J=8.1 & 15.3 Hz, 1H) 5.68 (dd, J=6.6 & 15.5 Hz, 1H)

Example 6

Synthesis of methyl(11R,12S,13E,15S,17R)-9-isobutyryloxy-11,15-bis(tert-butyldimethylsiloxy)-17,20-dimethyl-7-thiaprosta-8,13-dienoate (R$^1$=iPr, R$^2$=$^t$BuMe$_2$Si, R$^3$=H, R$^4$=2-Me-hexyl, W= $^t$BuMe$_2$SiO, X—Y=CH$_2$—CH$_2$, Z=CO$_2$Me, n=0, =trans-CH=CH)

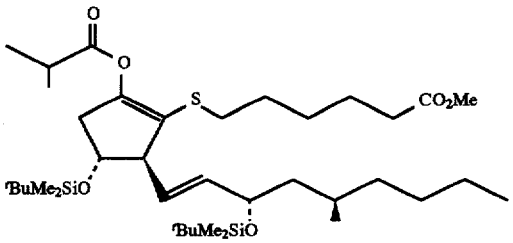

Using as the materials and reagents (1E,3S,5R)-1-iodo-3-(tert-butyldimethylsiloxy)-5-methyl-1-nonene (476 mg, 1.2 mmol), tert-butyllithium (1.54 mol/l, 1.56 ml, 2.4 mmol), 174 mg of 1-hexynylcopper, hexamethylphosphorous triamide (436 μl), (4R)-1-tert-butyldimethylsiloxy-2-(5-methoxycarbonylpentylthio)-2-cyclopenten-1-one (373 mg, 1 mmol), and isobutyric anhydride (448 μl), the same procedure was performed as in Example 1 to obtain methyl (11R,12S,13E,15S,17R)-9-isobutyryloxy-11,15-bis(tert-butyldimethylsiloxy)-17,20-dimethyl-7-thiaprosta-8,13-dienoate (466 mg, 65%).

$^1$H-NMR (270 MHz, δppm, CDCl$_3$) 0.04 (s), 0.05 (s) ...... 12H 0.8–0.9 (m, 6H) 0.88 (s, 9H) 0.89 (s, 9H) 1.1–1.7 (m, 15H) 1.24 (d, J=6.9 Hz, 3H) 1.25 (d, J=6.9 Hz, 3H) 2.30 (t, J=7.6 Hz, 2H) 2.3–2.8 (m, 4H) 2.91 (ddd, J=1.3 & 6.6 & 16.2 Hz, 1H) 3.12 (d, J=8.6 Hz, 1H) 3.66 (s, 3H) 4.1–4.2 (m, 2H) 5.43 (dd, J=8.6 & 15.2 Hz, 1H) 5.62 (dd, J=5.9 & 15.5 Hz, 1H)

Example 7

Synthesis of methyl(11R,12S,13E,15S,17R)-9-isobutyryloxy-11,15-dihydroxy-17,20-dimethyl-7-thiaprosta-8,13-dienoate (R$^1$=$^i$Pr, R$^2$=H, R$^3$=H, R$^4$=2-Me-hexyl, W=$^t$BuMe$_2$SiO, X—Y=CH$_2$—CH$_2$, Z=CO$_2$Me, n=0, ≕=trans-CH═CH)

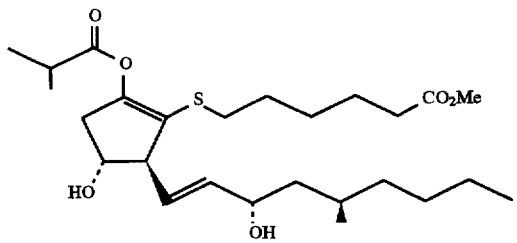

Using as the material and reagent a hydrogen fluoride-pyridine solution (0.6 ml) and methyl(11R,12S,13E,15S,17R)-9-isobutyryloxy-11,15-bis(tert-butyldimethylsiloxy)-17,20-dimethyl-7-thiaprosta-8,13-dienoate (466 mg), the same procedure as in Example 2 was performed to obtain methyl(11R,12S,13E,15S,17R)-9-isobutyryloxy-11,15-dihydroxy-17,20-dimethyl-7-thiaprosta-8,13-dienoate (192 mg, 64%).

$^1$H-NMR (270 MHz, δppm, CDCl$_3$) 0.8–1.0 (m, 6H) 1.1–1.7 (m, 15H) 1.25 (d, J=6.9 Hz, 6H) 2.31 (t, J=7.4 Hz, 2H) 2.4–2.8 (m, 4H) 2.90 (ddd, J=1.2 & 6.8 & 16.3 Hz, 1H) 3.21 (dd, J=3.1 & 8.1Hz, 1H) 3.67 (s, 3H) 4.1–4.3 (m, 2H) 5.56 (dd, J=8.1 & 15.3 Hz, 1H) 5.68 (dd, J=6.4 & 15.3 Hz, 1H)

Example 8

Synthesis of methyl(11R,12S,13E,15S,17R)-9-pivaloyloxy-11,15-bis(tert-butyldimethylsiloxy)-17,20-dimethyl-7-thiaprosta-8,13-dienoate (R$^1$=tBu, R$^2$=$^t$BuMe$_2$Si, R$^3$=H, R$^4$=2-Me-hexyl, W=$^t$BuMe$_2$SiO, X—Y=CH$_2$—CH$_2$, Z=CO$_2$Me, n=0, ≕=trans-CH═CH)

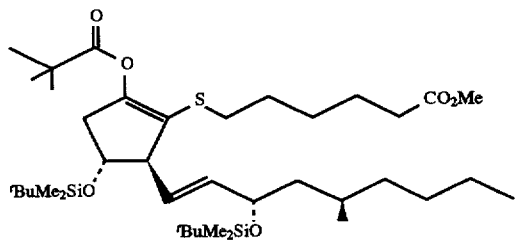

Using as the materials and reagents (1E,3S,5R)-1-iodo-3-(tert-butyldimethylsiloxy)-5-methyl-1-nonene (476 mg, 1.2 mmol), tert-butyllithium (1.54 mol/l, 1.56 ml, 2.4 mmol), 174 mg of 1-hexynylcopper, hexamethylphosphorous triamide (436 μl), (4R)-tert-butyldimethylsiloxy-2-(5-methoxycarbonylpentylthio)-2-cyclopenten-1-one (373 mg, 1 mmol), and pivaloyl anhydride (534 μl), the same procedure was performed as in Example 1 to obtain methyl(11R,12S,13E,15S,17R)-9-pivaloyloxy-11,15-bis(tert-butyldimethylsiloxy)-17,20-dimethyl-7-thiaprosta-8,13-dienoate (564 mg, 78%).

$^1$H-NMR (270 MHz, δppm, CDCl$_3$) 0.04 (s), 0.05 (s) ...... 12H 0.8–1.0 (m, 6H) 0.88 (s, 9H) 0.89 (s, 9H) 1.1–1.7 (m, 15H) 1.28 (s, 9H) 2.30 (t, J=7.6 Hz, 2H) 2.3–2.7 (m, 3H) 2.89 (ddd, J=1.3 & 6.9 & 16.2 Hz, 1H) 3.12 (d, J=8.3 Hz, 1H) 3.66 (s, 3H) 4.0–4.2 (m, 2H) 5.43 (dd, J=8.7 & 15.3 Hz, 1H) 5.62 (dd, J=6.3 & 15.5 Hz, 1H)

Example 9

Synthesis of methyl(11R,12S,13E,15S,17R)-9-pivaloyloxy-11,15-dihydroxy-17,20-dimethyl-7-thiaprosta-8,13-dienoate (R$^1$=tBu, R$^2$=H, R$^3$=H, R$^4$=2-Me-hexyl, W=OH, X—Y=CH$_2$—CH$_2$, Z=CO$_2$Me, n=0, ≕=trans-CH═CH)

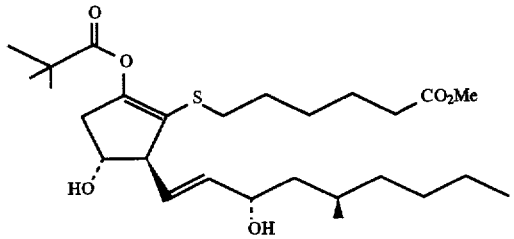

Using as the material and reagent a hydrogen fluoride-pyridine solution (0.7 ml) and methyl(11R,12S,13E,15S,17R)-9-pivaloyloxy-11,15-bis(tert-butyldimethylsiloxy)-17,20-dimethyl-7-thiaprosta-8,13-dienoate (564 mg), the same procedure was performed as in Example 2 was performed to obtain methyl(11R,13E,15S,17R)-9-pivaloyloxy-11,15-dihydroxy-17,20-dimethyl-7-thiaprosta-8,13-dienoate (211 mg, 55%).

$^1$H-NMR (270 MHz, δppm, CDCl$_3$) 0.8–1.0 (m, 6H) 1.1–1.7 (m, 15H) 1.29 (s, 9H) 2.31 (t, J=7.6 Hz, 2H) 2.4–2.8 (m, 3H) 2.94 (dd, J=6.3 & 16.5 Hz, 1H) 3.22 (d, J=7.6 Hz, 1H) 3.67 (s, 3H) 4.1–4.3 (m, 2H) 5.57 (dd, J=8.2 & 15.5 Hz, 1H) 5.72 (dd, J=5.9 & 15.5 Hz, 1H)

Example 10

Synthesis of butyl(11R,12S,13E,15S,17R)-9-butyryloxy-11,15-bis(t-butyldimethylsiloxy)-17,20-dimethyl-7-thiaprosta-8,13-dienoate (R$^1$=Pr, R$^2$=$^t$BuMe$_2$Si, R$^3$=H, R$^4$=2-Me-hexyl, W=$^t$BuMe$_2$SiO, X—Y=CH$_2$—CH$_2$, Z=CO$_2$Bu, n=0, ≕=trans-CH═CH)

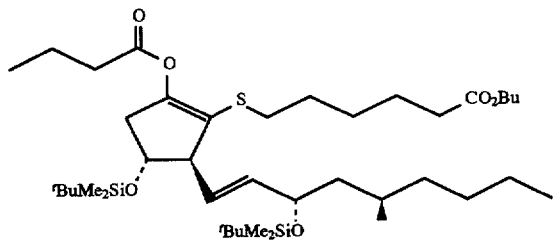

Using as the materials and reagents (1E,3S,5R)-1-iodo-3-(tert-butyldimethylsiloxy)-5-methyl-1-nonene (120 mg, 0.302 mmol), tert-butyllithium (1.54 mol/l, 392 μl, 0.302 mmol), 43.6 mg of 1-hexynylcopper, hexamethylphosphorous triamide (110 μl), (4R)-tert-butyldimethylsiloxy-2-(5-butoxycarbonylpentylthio)-2-cyclopenten-1-one (104 mg, 0.251 mmol), and butyric anhydride (111 μl), the same procedure was performed as in Example 1 to obtain butyl (11R,12S,13E,15S,17R)-9-butyryloxy-11,15-bis(tert-butyldimethylsiloxy)-17,20-dimethyl-7-thiaprosta-8,13-dienoate (138 mg, 73%).

$^1$H-NMR (270 MHz, δppm, CDCl$_3$) 0.03 (s), 0.04 (s) ...... 12H 0.8–0.9 (m, 6H) 0.86 (s, 9H) 0.88 (s, 9H) 0.92 (t, J=7.3 Hz, 3H) 0.99 (t, J=7.4 Hz, 3H) 1.0–1.8 (m, 21H) 2.27 (t, J=7.6 Hz, 2H) 2.3–2.7 (m, 3H) 2.41 (t, J=7.3 Hz, 2H) 2.91 (ddd, J=1.3 & 6.6 & 16.2 Hz, 1H) 3.10 (d, J=8.6 Hz, 1H) 4.0–4.2 (m, 2H) 4.05 (t, J=6.8 Hz, 2H) 5.42 (dd, J=8.6 & 15.2 Hz, 1H) 5.60 (dd, J=5.9 & 15.5 Hz, 1H)

Example 11

Synthesis of butyl(11R,12S,13E,15S,17R)-9-butylyloxy-11,15-dihydroxy-17,20-dimethyl-7-thiaprosta-8,13-dienoate (R$^1$=Pr, R$^2$=H, R$^3$=H, R$^4$= 2-Me-hexyl, W=OH, X—Y=CH$_2$—CH$_2$, Z=CO$_2$Bu, n=0, ═══trans-CH═CH)

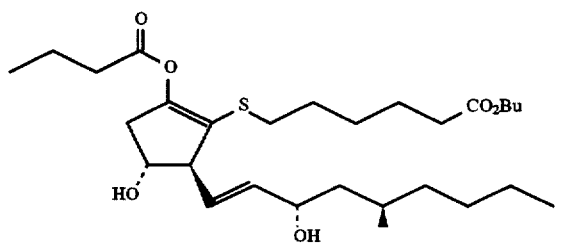

Using as the material and reagent a hydrogen fluoride-pyridine solution (0.2 ml) and butyl (11R,12S,13E,15S,17R)-9-butyryloxy-11,15-bis(tert-butyldimethylsiloxy)-17,20-dimethyl-7-thiaprosta-8,13-dienoate (138 mg), the same procedure as in Example 2 was performed to obtain butyl (11R,12S,13E,15S,17R)-9-butyryloxy-11,15-dihydroxy-17,20-dimethyl-7-thiaprosta-8,13-dienoate (69 mg, 72%).

$^1$H-NMR (270 MHz, δppm, CDCl$_3$) 0.8–1.0 (m, 6H) 0.94 (t, J=7.3 Hz, 3H) 1.01 (t, J=7.3 Hz, 3H) 1.1–1.8 (m, 21H) 2.29 (t, J=7.4 Hz, 2H) 2.4–2.8 (m, 3H) 2.44 (t, J=7.4 Hz, 2H) 2.96 (ddd, J=1.2 & 6.3 & 16.2 Hz, 1H) 3.21 (d, J=10.2 Hz, 1H) 4.07 (t, J=6.6 Hz, 2H) 4.1–4.3 (m, 2H) 5.57 (dd, J=8.1 & 15.7 Hz, 1H) 5.60 (dd, J=5.9 & 15.5 Hz, 1H)

Example 12

Synthesis of methyl(11R,12S,13E,15S)-9-butyryloxy-11,15-bis(tert-butyldimethylsiloxy)-7-thiaprosta-8,13-dienoate (R$^1$=Pr, R$^2$=$^t$BuMe$_2$Si, R$^3$= H, R$^4$=Pentyl, W=$^t$BuMe$_2$SiO, X—Y=CH$_2$—CH$_2$, Z=CO$_2$Me, n=0, ═══trans-CH═CH)

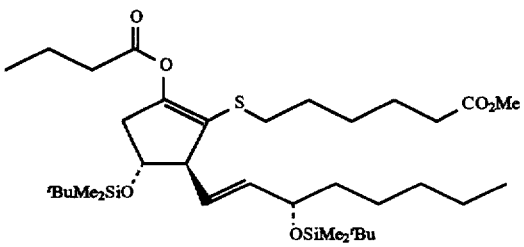

Using as the materials and reagents (1E,3S)-1-iodo-3-(tert-butyldimethylsiloxy)-1-octene (442 mg, 1.2 mmol), tert-butyllithium (1.54 mol/l, 1.56 ml, 2.4 mmol), 174 mg of 1-hexynylcopper, hexamethylphosphorous triamide (436 µl), (4R)-tert-butyldimethylsiloxy-2-(5-methoxycarbonylpentylthio)-2-cyclopenten-1-one (373 mg, 1.0 mmol), and burytic anhydride (441 µl), the same procedure was performed as in Example 1 to obtain methyl (11R,12S,13E,15S)-9-butyryloxy-11,15-bis(tert-butyldimethylsiloxy)-7-thiaprosta-8,13-dienoate (538 mg, 79%)

$^1$H-NMR (270 MHz, δppm, CDCl$_3$) 0.04 (s), 0.05 (s) ...... 12H 0.8–1.0 (m, 3H) 0.87 (s, 9H) 0.89 (s, 9H) 1.00 (t, J=7.3 Hz, 3H) 1.0–1.7 (m, 16H) 2.30 (t, J=7.6 Hz, 2H) 2.3–2.7 (m, 3H) 2.42 (t, J=7.3 Hz, 2H) 2.91 (ddd, J=1.3 & 6.8 & 16.3 Hz, 1H) 3.12 (d, J=5.9 Hz, 1H) 3.66 (s, 3H) 4.0–4.2 (m, 2H) 5.43 (dd, J=8.7 & 15.3 Hz, 1H) 5.57 (dd, J=5.8 & 15.3 Hz, 1H)

Example 13

Synthesis of methyl(11R,12S,13E,15S)-9-butyryloxy-11,15-dihydroxy-7-thiaprosta-8,13-dienoate (R$^1$=Pr, R$^2$=H, R$^3$=H, R$^4$=Pentyl, W=OH, X—Y=CH$_2$—CH$_2$, Z=CO$_2$Me, n=0, ═══trans-CH═CH)

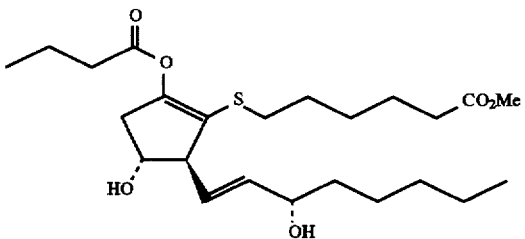

As the material and reagent, adding a hydrogen fluoride-pyridine solution (0.7 ml) and using methyl (11R,12S,13E,15S)-9-butyryloxy-11,15-bis(tert-butyldimethylsiloxy)-7-thiaprosta-8,13-dienoate (538 mg), the same procedure was performed as in Example 2 to obtain methyl(11R,12S,13E,15S)-9-butyryloxy-11,15-dihydroxy-7-thiaprosta-8,13-dienoate (287 mg, 80%).

$^1$H-NMR (270 MHz, δppm, CDCl$_3$) 0.89 (t, J=6.6 Hz, 3H) 1.01 (t, J=7.4 Hz, 3H) 1.2–1.8 (m, 16H) 2.31 (t, J=7.3 Hz, 2H) 2.4–2.8 (m, 3H) 2.43 (t, J=7.3 Hz, 2H) 2.96 (dd, J=6.3 & 16.5 Hz, 1H) 3.22 (d, J=8.3 Hz, 1H) 3.67 (s, 3H) 4.0–4.2 (m, 2H) 5.56 (dd, J=7.9 & 15.5 Hz, 1H) 5.70 (dd, J=6.3 & 15.5 Hz, 1H)

Example 14

Synthesis of methyl(11R,12S,13E,15S)-9-butyryloxy-11,15-bis(tert-butyldimethylsiloxy)-15-cyclopentyl-16,17,18,19,20-pentanor-7-thiaprosta-8,13-dienoate (R$^1$=Pr, R$^2$=$^t$BuMe$_2$Si, R$^3$=H, R$^4$=cyclo-Pentyl, W=$^t$BuMe$_2$SiO, X—Y=CH$_2$—CH$_2$, Z=CO$_2$Me, n=0, ═=trans-CH═CH)

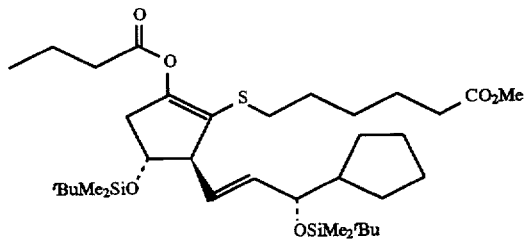

Using as the materials and reagents (1E,3S)-1-iodo-3-(tert-butyldimethylsiloxy)-3-cyclopentyl-1-propene (440 mg, 1.2 mmol), tert-butyllithium (1.54 mol/l, 1.56 ml, 2.4 mmol), 174 mg of 1-hexynylcopper, hexamethylphosphorous triamide (436 μl), (4R)-tert-butyldimethylsiloxy-2-(5-methoxycarbonylpentylthio)-2-cyclopenten-1-one (373 mg, 1.0 mmol), and butyric anhydride (441 μl), the same procedure was performed as in Example 1 to obtain methyl (11R,12S,13E,15S)-9-butyryloxy-11,15-bis(tert-butyldimethylsiloxy)-15-cyclopentyl-16,17,18,19,20-pentanor-7-thiaprosta-8,13-dienoate (321 mg, 47%).

$^1$H-NMR (270 MHz, δppm, CDCl$_3$) 0.02 (s), 0.04 (s), 0.05 (s) ...... 12H 0.88 (s, 9H) 0.89 (s, 9H) 1.00 (t, J=7.4 Hz, 3H) 1.2–2.0 (m, 17H) 2.30 (t, J=7.4 Hz, 2H) 2.3–2.7 (m, 3H) 2.42 (t, J=7.3 Hz, 2H) 2.95 (ddd, J=1.3 & 6.4 & 16.3 Hz, 1H) 3.11 (d, J=7.6 Hz, 1H) 3.66 (s, 3H) 3.90 (dd, J=6.6 & 6.6 Hz, 1H) 4.0–4.2 (m, 1H) 5.41 (dd, J=8.6 & 15.5 Hz, 1H) 5.62 (dd, J=6.4 & 15.3 Hz, 1H)

Example 15

Synthesis of methyl(11R,12S,13E,15S)-9-butyryloxy-11,15-dihydroxy-15-cyclopentyl-16,17,18,19,20-pentanor-7-thiaprosta-8,13-dienoate (R$^1$=Pr, R$^2$=H, R$^3$=H, R$^4$=cyclopentyl, W=OH, X—Y=CH$_2$—CH$_2$, Z=CO$_2$Me, n=0, ═=trans-CH═CH)

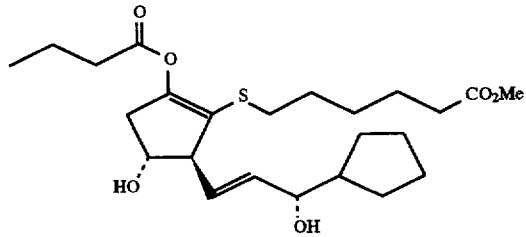

Using as the material and reagent a hydrogen fluoride-pyridine solution (0.4 ml) and methyl(11R, 12S,13E,15S)-9-butyryloxy-11,15-bis(tert-butyldimethylsiloxy)-15-cyclopentyl-16,17,18,19,20-pentanor-7-thiaprosta-8,13-dienoate (321 mg), the same procedure as in Example 2 was performed to obtain methyl (11R,12S,13E,15S)-9-butyryloxy-11,15-dihydroxy-15-cyclopentyl-16,17,18,19,20-pentanor-7-thiaprosta-8,13-dienoate (140 mg, 66%).

$^1$H-NMR (270 MHz, δppm, CDCl$_3$) 1.01 (t, J=7.4 Hz, 3H) 1.2–2.1 (m, 17H) 2.31 (t, J=7.4 Hz, 2H) 2.4–2.8 (m, 3H) 2.43 (t, J=7.3 Hz, 2H) 2.95 (ddd, J=1.3 & 6.6 & 16.5 Hz, 1H) 3.11 (d, J=2.5 & 8.3 Hz, 1H) 3.67 (s, 3H) 3.91 (dd, J=7.3 & 7.3 Hz, 1H) 4.1–4.2 (m, 1H) 5.57 (dd, J=7.9 & 15.5 Hz, 1H) 5.71 (dd, J=6.6 & 15.5 Hz, 1H)

Example 16

Synthesis of methyl(11R,12S,13E,15S)-9-butyryloxy-11,15-bis(tert-butyldimethylsiloxy)-15-cyclohexyl-16,17,18,19,20-pentanor-7-thiaprosta-8,13-dienoate (R$^1$=Pr, R$^2$=$^t$BuMe$_2$Si, R$^3$=H, R$^4$=cyclo-Hexyl, W=$^t$BuMe$_2$SiO, X—Y=CH$_2$—CH$_2$, Z=CO$_2$Me, n=0, ═=trans-CH═CH)

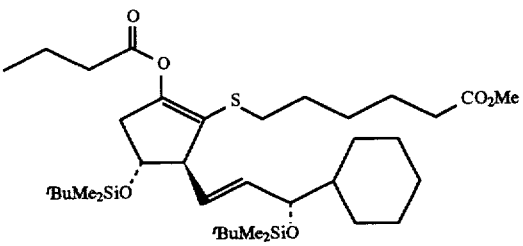

Using as the materials and reagents (1E,3S)-1-iodo-3-(tert-butyldimethylsiloxy)-3-cyclohesyl-1-propene (150 mg, 0.4 mmol), tert-butyllithium (1.50 mol/l, 0.53 ml, 0.79 mmol) 1-hexynylcopper (58 mg), hexamethylphosphorous triamide (145 μl), (4R)-4-(tert-butyldimethylsiloxy)-2-(5-methoxycarbonylpentylthio)-2-cyclopenten-1-one (124 mg, 0.33 mmol), and butyric anhydride (147 μl), the same procedure was performed as in Example 1 to obtain methyl (11R,12S,13E,15S)-9-butyryloxy-11,15-bis(tert-butyldimethylsiloxy)-15-cyclohexyl-16,17,18,19,20-pentanor-7-thiaprosta-8,13-dienoate (133 mg, 48%).

$^1$H-NMR (270 MHz, δppm, CDCl$_3$) 0.01 (s), 0.03 (s) ...... 12H 0.88 (s, 9H) 0.89 (s, 9H) 1.00 (t, J=7.5 Hz, 3H) 1.1–1.9 (m, 19H) 2.30 (t, J=7.6 Hz, 2H) 2.3–2.7 (m, 3H) 2.42 (t, J=7.5 Hz, 2H) 2.94 (ddd, J=1.0 & 6.6 & 16.2 Hz, 1H) 3.13 (d, J=8.5 Hz, 1H) 3.66 (s, 3H) 3.82 (t, J=6.0 Hz, 1H) 4.0–4.2 (m, 1H) 5.38 (dd, J=8.5 & 15.5 Hz, 1H), 5.60 (dd, J=6.3 & 15.5 Hz, 1H)

Example 17

Synthesis of methyl(11R,12S,13E,15S)-9-butyryloxy-11,15-dihydroxy-15-cyclohexyl-16,17,18,19,20-pentanor-7-thiaprosta-8,13-dienoate (R$^1$=Pr, R$^2$=H, R$^3$=H, R$^4$=cyclo-Hexyl, W=OH, X—Y=CH$_2$—CH$_2$, Z=CO$_2$Me, n=0, ═=trans-CH═CH)

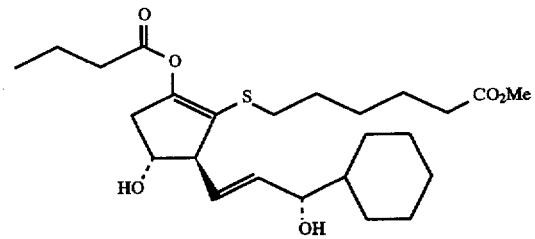

Using as the material and reagent a hydrogen fluoride-pyridine solution (0.2 ml) and methyl (11R,12S,13E,15S)-9-butyryloxy-11,15-bis(tert-butyldimethylsiloxy)-15-cyclohexyl-16,17,18,19,20-pentanor-7-thiaprosta-8,13-dienoate (130 mg), the same procedure as in Example 2 was performed to obtain methyl(11R,12S,13E,15S)-9-butyryloxy-11,15-dihydroxy-15-cyclohexyl-16,17,18,19,20-pentanor-7-thiaprosta-8,13-dienoate (60 mg, 67%).

$^1$H-NMR (270 MHz, δppm, CDCl$_3$) 1.01 (t, J=7.5 Hz, 3H) 0.9–1.9 (m, 19H) 2.31 (t, J=7.5 Hz, 2H) 2.43 (t, J=7.5 Hz, 2H) 2.5–2.8 (m, 3H) 2.94 (ddd, J=1.2 & 6.6 & 16.5 Hz, 1H) 3.22 (dd, J=2.5 & 8.2 Hz, 1H) 3.67 (s, 3H) 3.85 (dd, t=6.6 Hz, 1H) 4.1–4.2 (m, 1H) 5.53 (dd, J=7.9 & 15.5 Hz, 1H) 5.68 (dd, J=6.6 & 15.5 Hz, 1H)

Example 18

Synthesis of methyl(11R,12S,13E,15R)-9-butyryloxy-11,15-bis(tert-butyldimethylsiloxy)-15-cyclohexyl-16,17,18,19,20-pentanor-7-thiaprosta-8,13-dienoate (R$^1$=Pr, R$^2$=$^t$BuMe$_2$Si, R$^3$=H, R$^4$=cyclo-Hexyl, W=$^t$BuMe$_2$SiO, X—Y=CH$_2$—CH$_2$, Z=CO$_2$Me, n=0, ⚌=trans-CH=CH)

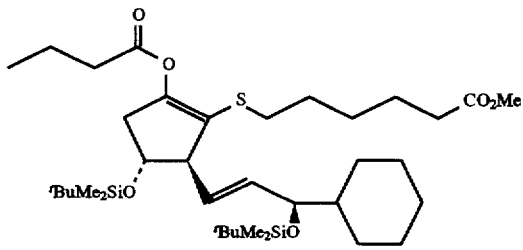

Using as the materials and reagents (1E,3R)-1-iodo-3-(tert-butyldimethylsiloxy)-3-cyclohexyl-1-propene (457 mg, 1.2 mmol), tert-butyllithium (1.54 mol/l, 1.56 ml, 2.4 mmol), 1-hexynylcopper (174 mg), hexamethylphosphorous triamide (436 μl), (4R)-tert-butyldimethylsiloxy-2-(5-methoxycarbonylpentylthio)-2-cyclopenten-1-one (373 mg, 1.0 mmol), and butyric anhydride (441 μl), the same procedure was performed as in Example 1 to obtain methyl (11R,12S,13E,15R)-9-butyryloxy-11,15-bis(tert-butyldimethylsiloxy)-15-cyclohexyl-16,17,18,19,20-pentanor-7-thiaprosta-8,13-dienoate (80 mg, 12%).

$^1$H-NMR (270 MHz, δppm, CDCl$_3$) 0.02 (s), 0.03 (s), 0.04 (s) ...... 12H 0.88 (s, 9H) 0.89 (s, 9H) 1.00 (t, J=7.4 Hz, 3H) 1.1–1.9 (m, 19H) 2.30 (t, J=7.4 Hz, 2H) 2.3–2.7 (m, 3H) 2.42 (t, J=7.4 Hz, 2H) 2.90 (ddd, J=1.3 & 6.9 & 16.2 Hz, 1H) 3.13 (dd, J=2.6 & 8.6 Hz, 1H) 3.66 (s, 3H) 3.81 (dd, J=6.3 & 6.3 Hz, 1H) 4.11 (ddd, J=3.3 & 3.6 & 6.6 Hz, 1H) 5.39 (dd, J=8.6 & 15.2 Hz, 1H) 5.59 (dd, J=6.9 & 15.5 Hz, 1H)

Example 19

Synthesis of methyl(11R,12S,13E,15R)-9-butyryloxy-11,15-dihydroxy-15-cyclohexyl-16,17,18,19,20-pentanor-7-thiaprosta-8,13-dienoate (R$^1$=Pr, R$^2$=H, R$^3$=H, R$^4$=cyclo-Hexyl, W=OH, X—Y=CH$_2$—CH$_2$, Z=CO$_2$Me, n=0, ⚌=trans-CH=CH)

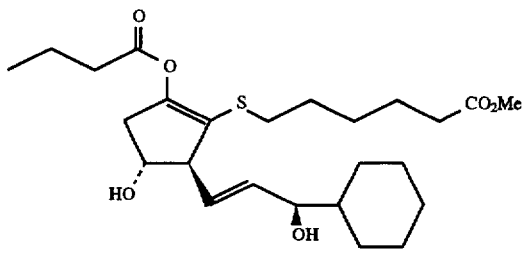

Using as the material and reagent a hydrogen fluoride-pyridine solution (0.1 ml) and methyl(11R,12S,13E,15R)-9-butyryloxy-11,15-bis(tert-butyldimethylsiloxy)-15-cyclohexyl-16,17,18,19,20-pentanor-7-thiaprosta-8,13-dienoate (80 mg), the same procedure as in Example 2 was performed to obtain methyl(11R,12S,13E,15R)-9-butyryloxy-11,15-dihydroxy-15-cyclohexyl-16,17,18,19,20-pentanor-7-thiaprosta-8,13-dienoate (32 mg, 59%).

$^1$H-NMR (270 MHz, δppm, CDCl$_3$) 1.01 (t, J=7.4 Hz, 3H) 1.1–1.9 (m, 19H) 2.31 (t, J=7.4 Hz, 2H) 2.3–2.8 (m, 3H) 2.44 (t, J=7.3 Hz, 2H) 2.90 (ddd, J=1.3 & 6.4 & 16.7 Hz, 1H) 3.23 (dd, J=1.3 & 7.9 Hz, 1H) 3.67 (s, 3H) 3.86 (dd, J=6.4 & 6.4 Hz, 1H) 4.1–4.2 (m, 1H) 5.55 (dd, J=8.3 & 15.5 Hz, 1H) 5.59 (dd, J=6.6 & 15.5 Hz, 1H)

Example 20

Synthesis of methyl(11R,12S,13E,15S)-9-benzoyloxy-11,15-bis(tert-butyldimethylsiloxy)-7-thiaprosta-8,13-dienoate (R$^1$=Ph, R$^2$=$^t$BuMe$_2$Si R$^3$=H, R$^4$=Pentyl, W=$^t$BuMe$_2$SiO, X—Y=CH$_2$—CH$_2$, Z=CO$_2$Me, n=0, ⚌=trans-CH=CH)

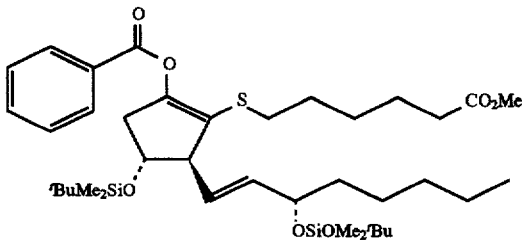

Using as the materials and reagents (1E,3S)-1-iodo-3-(tert-butyldimethylsiloxy)-1-octene (442 mg, 1.2 mmol), tert-butyllithium (1.54 mol/l, 1.56 ml, 2.4 mmol), 1-hexynylcopper (174 mg), hexamethylphosphorous triamide (436 μl), (4R)-tert-butyldimethylsiloxy-2-(5-methoxycarbonyl-pentylthio)-2-cyclopenten-1-one (373 mg, 1.0 mmol), and benzoic anhydride (661 mg), the same procedure was performed as in Example 1 to obtain methyl (11R,12S,13E,15S)-9-benzoyloxy-11,15-bis(tert-butyldimethylsiloxy)-7-thiaprosta-8,13-dienoate (239 mg, 33%).

$^1$H-NMR (270 MHz, δppm, CDCl$_3$) 0.06 (s), 0.07 (s), 0.07 (s) ...... 12H 0.8–1.0 (m, 3H) 0.89 (s, 9H) 0.91 (s, 9H) 1.00 (t, J=7.3 Hz, 3H) 1.2–1.7 (m, 14H) 2.25 (t, J=7.6 Hz, 2H) 2.4–2.8 (m, 3H) 3.07 (ddd, J=1.6 & 5.4 & 16.2 Hz, 1H) 3.19 (d, J=8.6 Hz, 1H) 3.65 s, 3H) 4.11 (dd, J=5.8 & 11.7 Hz, 1H) 4.20 (ddd, J=3.3 & 3.3 & 6.6 Hz, 1H) 5.48 (dd, J=8.4 & 15.7 Hz, 1H) 5.60 (dd, J=5.8 & 15.3 Hz, 1H) 7.47 (dd, J=7.2 & 7.9 Hz, 2H) 7.60 (dd, J=6.2 & 7.3 Hz, 1H) 8.12 (d, J=7.3 Hz, 2H)

Example 21

Synthesis of methyl(11R,12S,13E,15S)-9-benzoyloxy-11,15-dihydroxy-7-thiaprosta-8,13-dienoate ($R^1$=Ph, $R^2$=H, $R^3$=H, $R^4$=Pentyl, W=OH, X—Y=$CH_2$—$CH_2$, Z=$CO_2$Me, n=0, ⸗=trans-CH=CH)

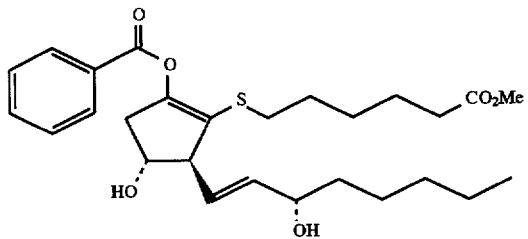

Using as the material and reagent a hydrogen fluoride-pyridine solution (0.3 ml) and methyl(11R,12S,13E,15S)-9-benzoyloxy-11,15-bis(tert-butyldimethylsiloxy)-7-thiaprosta-8,13-dienoate (239 mg), the same procedure as in Example 2 was performed to obtain methyl(11R,13E,15S)-9-benzoyloxy-11,15-dihydroxy-7-thiaprosta-8,13-dienoate (144 mg, 86%).

$^1$H-NMR (270 MHz, δppm, $CDCl_3$) 0.89 (t, J=6.8 Hz, 3H) 1.2–1.7 (m, 14H) 2.26 (t, J=7.4 Hz, 2H) 2.5–2.8 (m, 3H) 3.11 (dd, J=5.3 & 16.3 Hz, 1H) 3.28 (d, J=10.9 Hz, 1H) 3.65 (s, 3H) 4.14 (dd, J=6.3 & 12.5 Hz, 1H) 4.24 (ddd, J=3.0 & 3.3 & 6.2 Hz, 1H) 5.61 (dd, J=8.4 & 15.7 Hz, 1H) 5.75 (dd, J=6.3 & 15.5 Hz, 1H) 7.49 (dd, J=7.3 & 7.9 Hz, 2H) 7.62 (dd, J=6.3 & 7.6 Hz, 1H) 8.11 (d, J=7.3 Hz, 2H)

Example 22

Synthesis of methyl(11R,12S,13E,16S)-9-butyryloxy-11-(tert-butyldimethylsiloxy)-16-(trimethylsiloxy)-16-methyl-7-thiaprosta-8,13-dienoate ($R^1$=Pr, $R^2$=$^t$BuMe$_2$Si, $R^3$=Me, $R^4$=Bu, W=$^t$BuMe$_2$SiO, X—Y=$CH_2$—$CH_2$, Z=$CO_2$Me, n=1, ⸗=trans-CH=CH)

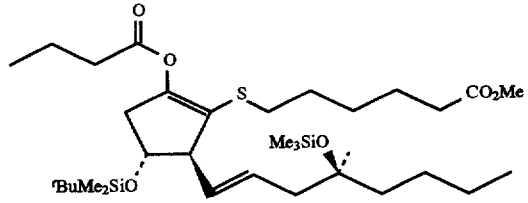

Using as the materials and reagents (1E,4S)-1-iodo-4-methyl-4-(trimethylsiloxy)-1-octene (408 mg, 1.2 mmol), tert-butyllithium (1.54 mol/l, 1.56 ml, 2.4 mmol), 1-hexynylcopper (174 mg), hexamethylphosphorous triamide (436 μl), (4R)-tert-butyldimethylsiloxy-2-(5-methoxycarbonyl-pentylthio)-2-cyclopenten-1-one (373 mg, 1.0 mmol), and butyric anhydride (441 μl), the same procedure was performed as in Example 1 to obtain methyl (11R,12S,13E,16S)-9-butyryloxy-11-(tert-butyldimethylsiloxy)-16-(trimethylsiloxyl)-16-methyl-7-thiaprosta-8,13-dienoate (226 mg, 35%).

$^1$H-NMR (270 MHz, δppm, $CDCl_3$) 0.04 (s), 0.10 (s) ...... 15H 0.8–1.0 (m, 3H) 0.87 (s, 9H) 1.00 (t, J=7.4 Hz, 3H) 1.17 (s, 3H) 1.2–1.8 (m, 14H) 2.0–2.8 (m, 9H) 2.88 (dd, J=6.6 & 16.5 Hz, 1H) 3.13 (d, J=6.4 Hz, 1H) 3.67 (s, 3H) 4.1–4.2 (m, 1H) 5.1–5.4 (m, 1H) 5.5–5.7 (m, 1H)

Example 23

Synthesis of methyl(11R,12S,13E,16S)-9-butyryloxy-11,16-dihydroxy-16-methyl-7-thiaprosta-8,13-dienoate ($R^1$=Pr, $R^2$=H, $R^3$=Me, $R^4$=Bu, W=OH, X—Y=$CH_2$—$CH_2$, Z=$CO_2$Me, n=1, ⸗=trans-CH=CH)

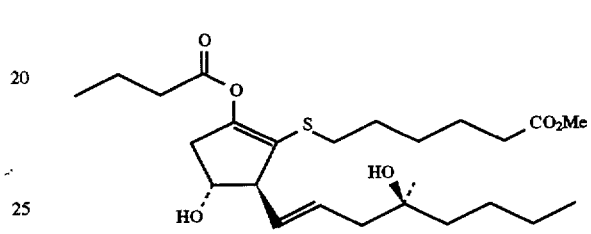

Using as the material and reagent a hydrogen fluoride-pyridine solution (0.1 ml) and methyl(11R,12S,13E,16S)-9-butyryloxy-11-(tert-butyldimethylsiloxy)-16-(trimethylsiloxy)-16-methyl-7-thiaprosta-8,13-dienoate (19 mg), the same procedure as in Example 2 was performed to obtain methyl(11R,12S,13E,16S)-9-butyryloxy-11,16-dihydroxy-16-methyl-7-thiaprosta-8,13-dienoate (5 mg, 37%).

$^1$H-NMR (270 MHz, δppm, $CDCl_3$) 0.91 (t, J=6.9 Hz, 3H) 1.00 (t, J=7.4 Hz, 3H) 1.16 (s, 3H) 1.2–1.8 (m, 14H) 2.20 (d, J=7.3 Hz, 2H) 2.31 (t, J=7.3 Hz, 2H) 2.43 (t, J=7.4 Hz, 2H) 2.5–2.8 (m, 3H) 2.95 (ddd, J=1.3 & 6.6 & 16.5 Hz, 1H) 3.22 (d, J=6.3 Hz, 1H) 3.67 (s, 3H) 4.18 (dt, J=3.3 & 3.3 Hz, 1H) 5.41 (dd, J=8.6 & 15.2 Hz, 1H) 5.72 (dt, J=15.2 & 7.3 Hz, 1H)

Example 24

Synthesis of allyl(11R,12S,13E,15S)-9-butyryloxy-11,15-bis(tert-butyldimethylsiloxy)-7-thiaprosta-8,13-dienoate ($R^1$=Pr, $R^2$=$^t$BuMe$_2$Si, $R^3$=H, $R^4$=Pentyl, W=$^t$BuMe$_2$SiO, X—Y=$CH_2$—$CH_2$, Z=$CO_2$-Allyl, n=0, ⸗=trans-CH=CH)

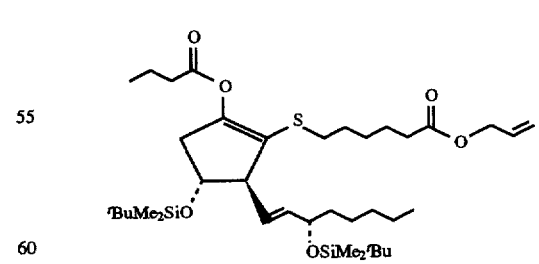

Using as the materials and reagents (1E,3S)-1-iodo-3-(tert-butyldimethylsiloxy)-1-octene (1.31 g, 3.57 mmol), tert-butyllithium(1.57 mol/l, 4.55 ml, 7.13 mmol), 1-hexynylcopper (516 mg), hexamethylphosphorous triamide (1.30 ml), (4R)-4-(tert-butyldimethylsiloxy)-2-(5-allyl oxycarbonylpentylthio)-2-cyclopenten-1-one (1.19 g, 2.97 mmol), and butyric anhydride (1.31 ml), the same procedure was performed as in Example 1 to obtain allyl(11R,12S, 13E,15S)-9-butyryloxy-11,15-bis(tert-butyldimethylsiloxyl)-7-thiaprosta-8,13-dienoate (1.63 mg, 77%).

$^1$H-NMR (270 MHz, δppm, CDCl$_3$) 0.04 (s), 0.05 (s) ...... 12H 0.8–0.9 (m, 3H) 0.87 (s, 9H) 0.89 (s, 9H) 1.00 (t, J=7.4 Hz, 3H) 1.2–1.8 (m, 16H) 2.32 (t, J=7.4 Hz, 2H) 2.4–2.7 (m, 3H) 2.42 (t, J=7.4 Hz, 2H) 2.91 (ddd, J=1.5 & 6.8 & 16.2 Hz, 1H) 3.12 (dd, J=2.6 & 8.6 Hz, 1H) 4.0–4.2 (m, 2H) 4.57 (dt, J=5.9 & 1.3 Hz, 2H) 5.23 (dd, J=1.3 & 10.6 Hz, 1H) 5.31 (dd, J=1.7 & 17.2 Hz, 1H) 5.43 (dd, J=8.6 & 16.2 Hz, 1H) 5.62 (dd, J=5.9 & 15.5 Hz, 1H) 5.8–6.0 (m, 1H)

Example 25

Synthesis of (11R,12S,13E,15S)-9-butyryloxy-11,15-bis(tert-butyldimethylsiloxy)-7-thiaprosta-8,13-dienoic acid (R$^1$=Pr, R$^2$=$^t$BuMe$_2$Si, R$^3$=H, R$^4$= pentyl, W=$^t$BuMe$_2$SiO, X—Y=CH$_2$—CH$_2$, Z= CO$_2$H, n=0, ==trans-CH=CH)

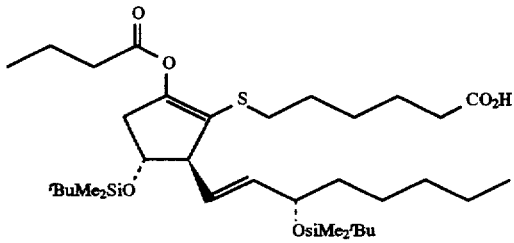

A tetrahydrofuran (10 ml) solution of formic acid (347 µl) and triethylamine (57.3 µl) was added to a tetrahydrofuran (20 ml) solution of palladium acetate (52 mg) and tributylphosphine (229 µl). Further a tetrahydrofuran (10 ml) solution of allyl(11R,12S,13E,15S)-9-butyryloxy-11,15-bis (tert-butyldimethylsiloxyl)-7-thiaprosta-8,13-dienoate (1.63 g) was added and the mixture was refluxed for one hour. The reaction solution was cooled, then was passed through a short column of Florisil to remove the catalyst. This solution was concentrated under reduced pressure, then was purified by silica gel column chromatography (10 to 20% ethyl acetate/hexane) to obtain (11R,12S,13E,15S)-9-butyryloxy-11,15-bis(tert-butyldimethylsiloxy)-7-thiaprosta-8,13-dienoic acid (1.41 g, 91%).

$^1$H-NMR (270 MHz, δppm, CDCl$_3$) 0.04 (s), 0.05 (s) ...... 12H 0.8–0.9 (m, 3H) 0.88 (s, 9H) 0.89 (s, 9H) 1.00 (t, J=7.3 Hz, 3H) 1.2–1.8 (m, 16H) 2.34 (t, J=7.2 Hz, 2H) 2.4–2.8 (m, 3H) 2.42 (t, J=7.4 Hz, 2H) 2.92 (ddd, J=1.7 & 5.3 & 16.5 Hz, 1H) 3.13 (dd, J=6.9 Hz, 1H) 4.0–4.2 (m, 2H) 5.43 (dd, J=8.6 & 16.2 Hz, 1H) 5.62 (dd, J=5.6 & 15.5 Hz, 1H)

Example 26

Synthesis of (11R,12S,13E,15S)-9-butyryloxy-11,15-dihydroxy-7-thiaprosta-8,13-dienoic acid (R$^1$=Pr, R$^2$=H, R$^3$=H, R$^4$=Pentyl, W=OH, X—Y=CH$_2$—CH$_2$, Z=CO$_2$H, n=0, ==trans-CH=CH)

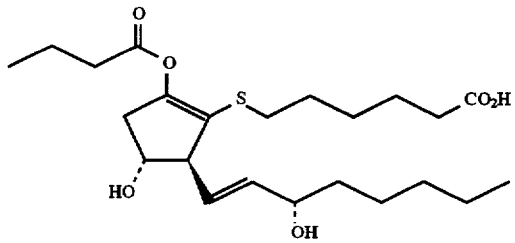

A hydrogen fluoride-pyridine solution (0.1 ml) was added to a solution of ice-cooled acetonitrile (1 ml) and pyridine (0.1 ml), then a pyridine (0.1 ml) solution of (11R,12S,13E, 15S)-9-butyryloxy-11,15-bis(tert-butyldimethylsiloxy)-7-thiaprosta-8,13-dienoic acid (79 mg) was added. The ice bath was detached, then the solution was stirred for 20 hours while raising it to room temperature. The reaction solution was poured into a mixture of ethyl acetate and saturated sodium hydrogencarbonate. The target substance was extracted from the mixture by ethyl acetate. The extract was washed with saturated sodium chloride solution, then was dried over anhydrous sodium sulfate. This solution was concentrated under reduced pressure, then was purified by a preparative TLC (Merck TLC plate silica gel 60 F$_{254}$, 20×20 cm, layer thickness 0.25 mm, 2 pieces, ethyl acetate:hexane 4:1) to obtain (11R,12S,13E,15S)-9-butyryloxy-11,15-dihydroxy-7-thiaprosta-8,13-diene acid (17 mg, 33%).

$^1$H-NMR (270 MHz, δppm, CDCl$_3$) 0.8–1.1 (m, 6H) 1.2–1.8 (m, 16H) 2.34 (t, J=7.1 Hz, 2H) 2.4–2.8 (m, 3H) 2.44 (t, J=7.4 Hz, 2H) 2.96 (dd, J=6.3 & 16.2 Hz, 1H) 3.23 (d, J=7.6 Hz, 1H) 4.0–4.2 (m, 2H) 5.56 (dd, J=7.9 & 15.5 Hz, 1H) 5.70 (dd, J=6.6 & 15.5 Hz, 1H)

Example 27

Synthesis of methyl(11R,12S,13E,15S)-9-butyryloxy-11,15-bis(tert-butyldimethylsiloxy)-18-oxa-7-thiaprosta-8,13-dienoate (R$^1$=Pr, R$^2$= $^t$BuMe$_2$Si, R$^3$=H, R$^4$=2-ethoxyethyl, W= $^t$BuMe$_2$SiO, X—Y=CH$_2$—CH$_2$, Z=CO$_2$Me, n=0, ==trans-CH=CH)

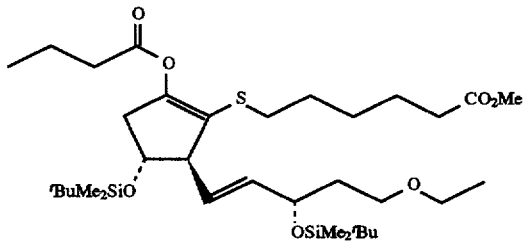

Using as the materials and reagents (1E,3S)-1-iodo-3-(tert-butyldimethylsiloxy)-5-ethoxy-1-pentene (444 mg, 1.2 mmol), tert-butyllithium (1.54 mol/l, 1.56 ml, 2.4 mmol), 1-hexynylcopper (174 mg), hexamethylphosphorous triamide (436 µl), (4R)-4-(tert-butyldimethylsiloxy)-2-(5-methoxycarbonylpentylthio)-2-cyclopenten-1-one (373 mg, 1.0 mmol), and butyric anhydride (441 µl), the same procedure was performed as in Example 1 to obtain methyl (11R,12S,13E,15S)-9-butyryloxy-11,15-bis(tert-butyldimethylsiloxy)-18-oxa-7-thiaprosta-8,13-dienoate (192 mg, 28%).

¹H-NMR (270 MHz, δppm, CDCl₃) 0.04 (s), 0.06 (s) ...... 12H 0.87 (s, 9H) 0.90 (s, 9H) 1.00 (t, J=7.4 Hz, 3H) 1.19 (t, J=6.9 Hz, 3H) 1.2–1.8 (m, 10H) 2.30 (t, J=7.4 Hz, 2H) 2.4–2.8 (m, 3H) 2.42 (t, J=7.4 Hz, 2H) 2.91 (ddd, J=1.6 & 6.6 & 16.2 Hz, 1H) 3.12 (d, J=5.9 Hz, 1H) 3.4–3.6 (m, 4H) 3.66 (s, 3H) 4.1–4.2 (m, 1H) 4.28 (dt, J=5.9 & 6.3 Hz, 1H) 5.46 (dd, J=8.7 & 15.3 Hz, 1H) 5.63 (dd, J=5.8 & 15.3 Hz, 1H)

Example 28

Synthesis of methyl(11R,12S,13E,15S)-9-butyryloxy-11,15-dihydroxy-18-oxa-7-thiaprosta-8,13-dienoate (R¹=Pr, R²=H, R³=H, R⁴=2-Ethoxyethyl, W=OH, X—Y=CH₂—CH₂, Z=CO₂Me, n=0, ═=trans-CH═CH)

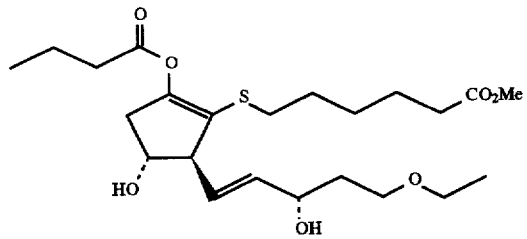

Using as the materias and reagent a hydrogen fluoride-pyridine solution (0.2 ml) and methyl(11R,12S,13E,15S)-9-butyryloxy-11,15-bis(tert-butyldimethylsiloxy)-18-oxa-7-thiaprosta-8,13-dienoate (192 mg), the same procedure as in Example 2 was performed to obtain methyl(11R,13E,15S)-9-butyryloxy-11,15-dihydroxy-18-oxa-7-thiaprosta-8,13-dienoate (115 mg, 89%).

¹H-NMR (270 MHz, δppm, CDCl₃) 1.00 (t, J=7.4 Hz, 3H) 1.20 (t, J=6.9 Hz, 3H) 1.13–1.9 (m, 10H) 2.31 (t, J=7.4 Hz, 2H) 2.4–2.8 (m, 3H) 2.43 (t, J=7.4 Hz, 2H) 2.90 (ddd, J=1.3 & 6.9 & 16.2 Hz, 1H) 3.21 (dd, J=3.3 & 7.9 Hz, 1H) 3.49 (q, J=6.9 Hz, 2H) 3.5–3.7 (m, 2H) 3.67 (s, 3H) 4.1–4.2 (m, 1H) 4.32 (dt, J=5.6 & 5.8 Hz, 1H) 5.60 (dd, J=7.9 & 15.5 Hz, 1H) 5.70 (dd, J=5.9 & 15.2 Hz, 1H)

Example 29

Synthesis of methyl(11R,12S,13E,15S,17R)-9-benzoyloxy-11,15-bis(tert-butyldimethylsiloxy)-17,20-dimethyl-7-thiaprosta-8,13-dienoate (R¹=Ph, R²=ᵗBuMe₂Si, R³=H, R⁴=2-Me-hexyl, W=ᵗBuMe₂SiO, X—Y=CH₂—CH₂, Z=CO₂Me, n=0, ═=trans-CH═CH)

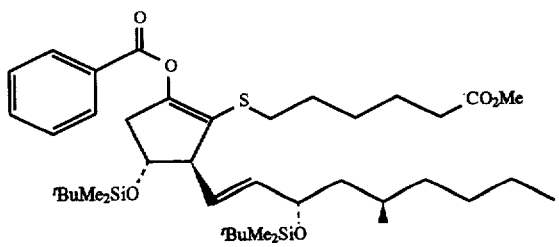

Using as materials (1E,3S,5R)-1-iodo-3-(tert-butyldimethylsiloxy)-5-methyl-1-nonene (476 mg, 1.2 mmol), tert-butyllithium (1.54 mol/l, 1.56 ml, 2.4 mmol), 1-hexynylcopper (174 mg), hexamethylphosphorous triamide (436 µl), (4R)-4-(tert-butyldimethylsiloxy)-2-(5-methoxycarbonylpentylthio)-2-cyclopenten-1-one (373 mg, 1.0 mmol), and benzoic anhydride (611 mg), the same procedure was performed as in Example 1 to obtain methyl (11R,12S,13E,15S,17R)-9-benzoyloxy-11,15-bis(tert-butyldimethylsiloxy)-17,20-dimethyl-7-thiaprosta-8,13-dienoate (734 mg, 98%).

¹H-NMR (270 MHz, δppm, CDCl₃) 0.06 (s), 0.06 (s), 0.07 (s), 0.08 (s) ...... 12H 0.8–1.0 (m, 6H) 0.90 (s, 9H) 0.90 (s, 9H) 1.0–1.7 (m, 15H) 2.25 (t, J=7.4 Hz, 2H) 2.5–2.8 (m, 3H) 3.08 (dd, J=5.5 & 16.2 Hz, 1H) 3.18 (d, J=6.3 Hz, 1H) 3.64 (s, 3H) 4.1–4.2 (m, 1H) 5.48 (dd, J=8.6 & 15.5 Hz, 1H) 5.67 (dd, J=6.1 & 15.3 Hz, 1H) 7.47 (t, J=7.6 Hz, 2H) 7.60 (t, J=7.4 Hz, 1H) 8.12 (d, J=7.3 Hz, 2H)

Example 30

Synthesis of methyl(11R,12S,13E,15S,17R)-9-benzoyloxy-11,15-dihydroxy-17,20-dimethyl-7-thiaprosta-8,13-dienoate (R¹=Ph, R²=H, R³=H, R⁴=2-Me-hexyl, W=OH, X—Y=CH₂—CH₂, Z=CO₂Me, n=0, ═=trans-CH═CH)

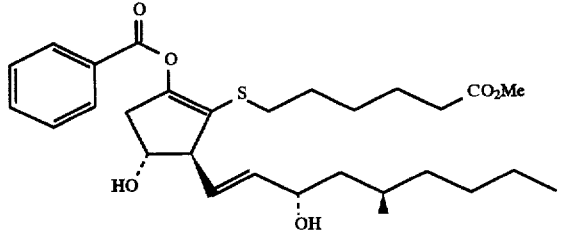

Using as the material and reagent a hydrogen fluoride-pyridine solution (0.7 ml) and methyl(11R,12S,13E,15S,17R)-9-benzoyloxy-11,15-bis(tert-butyldimethylsiloxy)-17,20-dimethyl-7-thiaprosta-8,13-dienoate (734 mg), the same procedure as in Example 2 was performed to obtain methyl (11R,12S,13E,15S,17R)-9-benzoyloxy-11,15-dihydroxy-17,20-dimethyl-7-thiaprosta-8,13-dienoate (141 mg, 28%)

¹H-NMR (270 MHz, δppm, CDCl₃) 0.89 (t, J=6.3 Hz, 3H) 0.92 (d, J=6.3 Hz, 9H) 1.1–1.7 (m, 15H) 2.26 (t, J=7.4 Hz, 2H) 2.5–2.8 (m, 3H) 3.10 (dd, J=6.8 & 16.7 Hz, 1H) 3.28 (d, J=5.6 Hz, 1H) 3.65 (s, 3H) 4.2–4.3 (m, 1H) 5.63 (dd, J=8.1 & 15.3 Hz, 1H) 5.76 (dd, J=6.3 & 15.5 Hz, 1H) 7.49 (t, J=7.8 Hz, 2H) 7.62 (t, J=7.3 Hz, 1H) 8.11 (d, J=7.3 Hz, 2H)

Example 31

Synthesis of methyl(11R,12S,13E,15S)-9-(N-benzyloxycarbonylphenylalanyloxy)-11,15-bis(tert-butyldimethylsiloxy)-7-thiaprosta-8,13-dienoate (R¹=1-(Cbz-NH)-2-Ph—ethyl, R²=ᵗBuMe₂Si, R³=H, R⁴=Pentyl, W=ᵗBuMe₂SiO, X—Y=CH₂—CH₂, Z=CO₂Me, n=0, ═=trans-CH═CH)

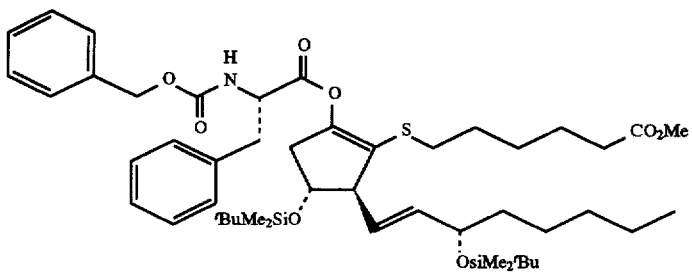

An ether (1.5 ml) solution of (1E,3S)-1-iodo-3-(tert-butyldimethylsiloxy)-1-octene (221 mg, 0.6 mmol) was cooled to −78° C., then tert-butyllithium (1.50 mol/l, 0.80 ml, 1.2 mmol) was added and the mixture was stirred as is at −78° C. for two hours. Further an ether (3 ml) solution of 1-hexynylcopper (87 mg) and hexamethylphosphorous triamide (218 μl) was added thereto and the mixture was further stirred as is at −78° C. for one hour to produce a copper reagent. A tetrahydrofuran (10 ml) solution of (4R)-tert-butyldimethylsiloxy-2-(5-methoxycarbonylpentylthio)-2-cyclopenten-1-one (187 mg, 0.5 mmol) was dropwise added to the copper reagent thus obtained. This reaction mixture was stirred as is at −78° C. for 15 minutes, then the reaction temperature was raised and the mixture was stirred at −50° to −30° C. for one hour. Further, a tetrahydrofuran (6 ml) solution of a mixed acid anhydride (1.35 mmol) of N-benzyloxycarbonylphenylalanine separately prepared at −30° C. was added then the mixture was stirred for 15 hours while raising the reaction temperature to room temperature. The reaction solution was poured into saturated ammonium sulfate (40 ml), then the organic layer was separated, then the aqueous layer was extracted with ether, the extract was combined with the organic layer, then was dried over anhydrous magnesium sulfate. This solution was concentrated under reduced pressure, then was purified by silica gel column chromatography (10% ethyl acetate/hexane) to obtain methyl(11R,13E,15S)-9-(N-benzyloxycarbonylphenylalanyloxy)-11,15-bis(tert-butyldimethylsiloxy)-7-thiaprosta-8,13-dienoate (148 mg, 33%).

The mixed acid anhydride of N-benzyloxycarbonylphenylalanine was prepared as follows. A tetrahydrofuran (6 ml) solution of N-benzyloxycarbonylphenylalanine (414 mg, 1.35 mmol) was stirred and cooled to −15° C. N-Methyl morpholine (137 mg, 1.35 mmol) was added, then isobutyl chloroformate (184 mg, 1.35 mmol) was added and the mixture stirred at −15° C. for 30 minutes. The resulting precipitate was removed and the mixture was used for the reaction.

$^1$H-NMR (270 MHz, δppm, CDCl$_3$) 0.06 (s), 0.06 (s) ..... 12H 0.88 (s, 9H) 0.90 (s, 9H) 1.1–1.8 (m, 18H) 2.28 (t, J=7.6 Hz, 2H) 2.3–3.0 (m, 4H) 3.1–3.4 (m, 2H) 3.64 (s, 3H) 4.0–4.2 (m, 2H) 4.7–4.8 (m, 1H) 5.09 (d, J=13.0 Hz, 2H) 5.21 (d, J=8.5 Hz, 1H) 5.44 (dd, J=7.9 & 15.5 Hz, 1H) 5.62 (dd, J=5.3 & 15.5 Hz, 1H) 7.1–7.4 (m, 11H)

Example 32

Synthesis of methyl(11R,12S,13E,15S)-9-(N-benzyloxycarbonylphenylalanyloxy)-11,15-dihydroxy-7-thiaprosta-8,13-dienoate (R$^1$=1-(Cbz-NH)-2-Ph-ethyl, R$^2$=H, R$^3$=H, R$^4$=Pentyl, W=OH, X—Y=CH$_2$—CH$_2$, Z=CO$_2$Me, n=0, ═=trans-CH═CH)

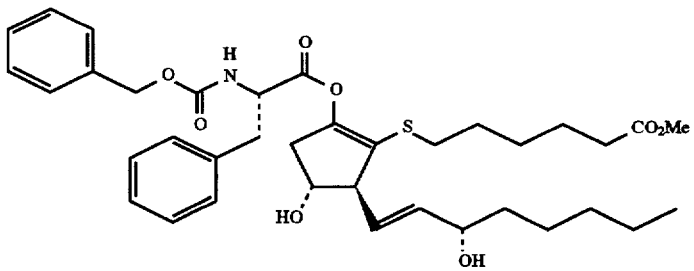

Using as the material and reagent a hydrogen fluoride-pyridine solution (0.3 ml) and methyl(11R,12S,13E,15S)-9-(N-benzyloxycarbonylphenylalanyloxy)-11,15-bis(tert-butyldimethylsiloxy)-7-thiaprosta-8,13-dienoate (140 mg), methyl(11R,12S,13E,15S)-9-(N-benzyloxycarbonylphenylalanyloxy)-11,15-dihydroxy-7-thiaprosta-8,13-dienoate (53 mg, 51%) was obtained.

$^1$H-NMR (270 MHz, δppm, CDCl$_3$) 0.89 (t, J=7.0 Hz, 3H) 1.1–2.1 (m, 14H) 2.28 (t, J=7.2 Hz, 2H) 2.4–3.0 (m, 5H) 3.1–3.4 (m, 3H) 3.64 (s, 3H) 4.1–4.2 (m, 2H) 4.7–4.8 (m, 1H) 5.09 (d, J=3.0 Hz, 2H) 5.28 (d, J=7.9 Hz, 1H) 5.55 (dd, J=7.9 & 15.5 Hz, 1H) 5.68 (dd, J=6.4 & 15.5 Hz, 1H) 7.1–7.4 (m, 10H)

Example 33

Synthesis of methyl(11R,12S,15S)-9-butyrxloxy-11-tert-butyldimethylsiloxy-15-(2-tetrahydropyranyloxy)-7-thia-8-prostenoate (R¹=Pr, R²=THP, R³=H, R⁴=Pentyl, W=ᵗBuMe₂SiO, X—Y=CH₂—CH₂, Z=CO₂Me, n=0, ⸗CH₂—CH₂)

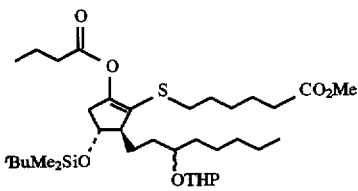

Using as the materials and reagents 1-iodo-3-(2-tetrahydropyranyloxy)-octane (263 mg, 0.773 mmol), tert-butyllithium (1.54 mol/l, 1.0 ml, 1.55 mmol), 1-hexynylcopper (112 mg), hexamethylphosphorous triamide (281 μl), (4R)-4-(tert-butyldimethylsiloxy)-2-(5-methoxycarbonyl-pentylthio)-2-cyclopenten-1-one (240 mg, 0.644 mmol), and butyric anhydride (284 μl), the same procedure was performed as in Example 1 to obtain methyl (11R,12S,15S)-9-butyryloxy-11-tert-butyldimethylsiloxy-15-(2-tetrahydropyranyloxy)-7-thia-8-prostenoate (171 mg, 40%).

¹H-NMR (270 MHz, δppm, CDCl₃) 0.06 (s, 3H) 0.07 (s, 3H) 0.8–0.9 (m, 3H) 0.88 (s, 9H) 1.00 (t, J=7.3 Hz, 3H) 1.2–1.8 (m, 20H) 2.30 (t, J=7.4 Hz, 2H) 2.4–2.8 (m, 4H) 2.42 (t, J=7.4 Hz, 2H) 2.8–3.0 (m, 1H) 3.3–3.5 (m, 1H) 3.5–3.7 (m, 1H) 3.66 (s, 3H) 3.8–4.0 (m, 1H) 4.0–4.2 (m, 1H) 4.5–4.7 (m, 1H)

Example 34

Synthesis of meth(11R,12S,15S)-9-butyryloxy-11,15-dihydroxy-7-thia-8-prostenoate (R¹=Pr, R²=H, R³=H, R⁴=Pentyl, W=OH, X—Y=CH₂—CH₂, Z=CO₂Me, n=0,⸗CH=CH₂)

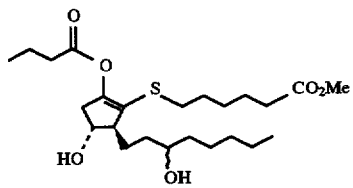

A hydrogen fluoride-pyridine solution (0.2 ml) was added to a solution of ice-cooled acetonitrile (2 ml) and pyridine (0.2 ml), then a pyridine (0.2 ml) solution of methyl(11R, 12S,15S)-9-butyryloxy-11-tert-butyldimethylsiloxy-15-(2-tetrahydropyranyloxy)-7-thia-8-prostenoate (171 mg) was added. The ice bath was removed and the solution was stirred for 20 hours while raising it to room temperature. The reaction solution was poured into a mixture of ethyl acetate and saturated sodium hydrogen carbonate. The desired substance was extracted from the mixture by ethyl acetate. The extract was washed with saturated sodium chloride solution, then was dried over anhydrous sodium sulfate. This solution was concentrated under reduced pressure, then tetrahydrofuran (4 ml) was added to make a solution, water (2 ml) and acetic acid (8 ml) were added, then the mixture was stirred at 45° C. for two hours. The reaction solution was diluted by ethyl acetate, then was washed by saturated sodium chloride solution and was dried over anhydrous sodium sulfate. This solution was concentrated under reduced pressure, then was purified by silica gel column chromatography (40 to 50% ethyl acetate/hexane) to obtain methyl(11R,12S,15S)-9-butyryloxy-11,15-hydroxy-7-thia-8-prostenoate (85 mg, 71%).

¹H-NMR (270 MHz, δppm, CDCl₃) 0.89 (t, J=6.6 Hz, 3H) 1.00 (t, J=7.4 Hz, 3H) 1.2–1.9 (m, 20H) 2.31 (t, J=7.4 Hz, 2H) 2.4–2.8 (m, 4H) 2.42 (t, J=7.4 Hz, 2H) 2.96 (ddt, J=6.6 & 16.8 & 1.0 Hz, 1H) 3.5–3.7 (m, 1H) 3.67 (s, 3H) 4.1–4.2 (m, 1H)

Example 35

Synthesis of (3S,4R)-4-(tert-butyldimethylsiloxy)-1-butyryloxy-2-(5-methoxycarbonylpentylthio)-3-(trans-2-tributylstanylvinyl)-1-cyclopentene

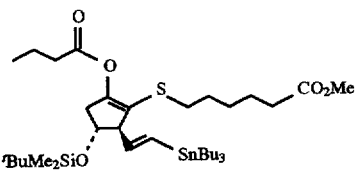

Methyllithium (1.25 mol/l, 37 ml) was added to a tetrahydrofuran (35 ml) suspension of ice-cooled copper(I) cyanide (1.88 g), then the reaction solution was raised to room temperature. To this was added a tetrahydrofuran (35 ml) solution of trans-1,2-bis(tributylstanyl)ethylene (14.4 g), then the mixture was stirred as is at room temperature for a further 1.5 hours to produce a copper reagent. The thus obtained copper reagent was cooled to −78° C., then a tetrahydrofuran (30 ml) solution of (4R)-tert-butyldimethylsiloxy-2-(5-methoxycarbonylpentylthio)-2-cyclopenten-1-one (5.60 g) was dropwise added. This reaction solution was raised in temperature to −35° C. over one hour, then was stirred as is for 30 minutes. Further, butyric anhydride (8.60 ml) was added to the reaction solution and the mixture was stirred for three hours while raising the reaction temperature to room temperature. The reaction solution was poured into a mixture of an aqueous solution of saturated ammonium sulfate and concentrated ammonium hydroxide solution (9:1, 300 ml). Extraction was performed from this mixture by ether the extract was washed with saturated sodium chloride solution, then was dried over anhydrous magnesium sulfate, was concentrated under reduced pressure, then was purified by silica gel column chromatography (3 to 5% ethyl acetate/hexane) to obtain (3S,4R)-4-(tert-butyldimethylsiloxy)-1-butyryloxy-2-(5-methoxycarbonylpentylthio)-3-(trans-2-tributylstanylvinyl)-1-cyclopentene (10.5 g, 92%).

¹H-NMR (270 MHz, δppm, CDCl₃) 0.00 (s, 6H) 0.84 (s, 9H) 0.85 (t, J=7.0 Hz, 9H) 0.97 (t, J=7.4 Hz, 3H) 1.1–1.8 (m, 26H) 2.26 (t, J=7.5 Hz, 2H) 2.39 (t, J=7.5 Hz, 2H) 2.4–2.7 (m, 3H) 2.81 (dd, J=6.9 & 16.5 Hz, 1H) 3.1–3.2 (m, 1H) 3.63 (s, 3H) 4.1–4.2 (m, 1H) 5.80 (dd, J=8.2 & 18.8 Hz, 1H) 6.09 (d, J=18.8 Hz, 1H)

Example 36

Synthesis of (3S,4R)-4-(tert-butyldimethylsiloxy)-1-butyryloxy-2-(5-methoxycarbonylpentylthio)-3-(trans-2-iodovinyl)-1-cyclopentene

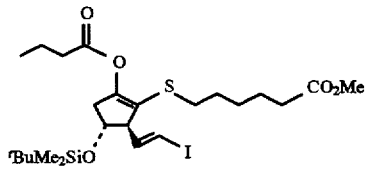

Iodine (2.92 g) was added to an ether (90 ml solution of (3S,4R)-4-(tert-butyldimethylsiloxy)-1-butyryloxy-2-(5-methoxycarbonylpentylthio)-3-(trans-2-tributylstanylvinyl)-1-cyclopentene (8.74 g) and the mixture was stirred at room temperature for one hour. A saturated sodium thiosulfate solution (50 ml) was added to the reaction solution, then the mixture was extracted by ether. The extract was washed with saturated sodium chloride solution, then was dried over anhydrous magnesium sulfate, was concentrated under reduced pressure, then was purified by silica gel column chromatography (5% ethyl acetate/hexane) to obtain (3S, 4R)-4-(tert-butyldimethylsiloxy)-1-butyryloxy-2-(5-methoxycarbonylpentylthio)-3-(trans-2-iodovinyl)-1-cyclopentene (6.44 g, 94%).

$^1$H-NMR (270 MHz, δppm, $CDCl_3$) 0.05 (s, 6H) 0.87 (s, 9H) 1.00 (t, J=7.4 Hz, 3H) 1.2–1.8 (m, 8H) 2.31 (t, J=7.3 Hz, 2H) 2.4–2.7 (m, 3H) 2.42 (t, J=7.4 Hz, 2H) 2.84 (dd, J=6.9 & 16.5 Hz, 1H) 3.1–3.2 (m, 1H) 3.67 (s, 3H) 4.0–4.2 (m, 1H) 6.28 (d, J 14.5 Hz, 1H) 6.45 (dd, J=8.3 & 14.5 Hz, 1H)

Example 37

Synthesis of methyl(11R,12S,13E)-9-butyryloxy-11, 15-bis(tert-butyldimethylsiloxy)-17-phenyl-18,19, 20-trinor-7-thiaprosta-8,13-dienoate ($R^1$=Pr, $R^2$=H, $R^3$=H, $R^4$=2-phenylethyl, W=$^t$BuMe$_2$SiO, X—Y=$CH_2$—$CH_2$, Z=$CO_2$Me, n=0, ═=trans-CH═CH)

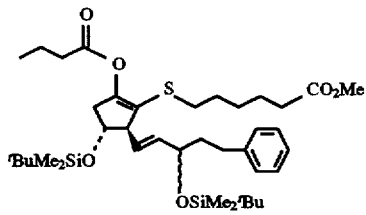

A tetrahydrofuran (1 ml) suspension of copper cyanide(I) (63 mg) was ice cooled, then methyllithium (1.25 mol/l, 1.23 ml) was added and the mixture was raised to room temperature while stirring. To this solution was added a tetrahydrofuran (1.5 ml) solution of (1E)-1-tributylstannio-3-(tert-butyldimethylsiloxy)-5-phenyl-1-pentene (447 mg, 0.79 mmol), then the mixture was stirred at room temperature for one hour to produce a copper reagent. The resultant copper reagent was cooled to −78° C., then a tetrahydrofuran (1.5 ml) solution of (4R)-tert-butyldimethylsiloxy-2-(5-methoxycarbonylpentylthio)-2-cyclopenten-1-one (186 mg, 0.5 mmol) was dropwise added thereto. The reaction mixture was immediately raised to −35° C. then was stirred at −35° C. for 30 minutes. Further, burytic anhydride (286 μl) was added to the reaction solution at −35° C., then the mixture was stirred for one and a half hours while raising the reaction temperature to room temperature. The reaction solution was poured into a mixture (9:1, 40 ml) of saturated ammonium sulfate and concentrated ammonium hydroxide solution, the organic layer was separated, then the aqueous layer was extracted with ether, the extract was combined with the organic layer, then this was dried over anhydrous magnesium sulfate. This solution was concentrated under reduced pressure, then was purified by silica gel column chromatography (4% ethyl acetate/hexane) to obtain methyl (11R,12S,13E)-9-butyryloxy-11,15-bis(tert-butyldimethylsiloxy)-17-phenyl-18,19,20-trinor-7-thiaprosta-8,13-dienoate (322 mg, 90%).

Note that the methyl(11R,12S,13E)-9-butyryloxy-11,15-bis(tert-butyldimethylsiloxy)-17-phenyl-18,19,20-trinor-7-thiaprosta-8,13-dienoate thus obtained is a diastereomer mixture of mixed stereo isomers of different hydroxyl groups at the 15-position.

$^1$H-NMR (270 MHz, δppm, $CDCl_3$) 0.04 (s), 0.05 (s), 0.05 (s), 0.06 (s) . . . . . . 12H 0.87 (s, 9H) 0.90 (s, 9H) 1.00 (t, J=7.4 Hz, 3H) 1.5–1.8 (m, 12H) 2.1–2.3 (m, 2H) 2.3–2.7 (m, 3H) 2.7–3.0 (m, 1H) 3.14 (d, J=10.0 Hz, 1H) 3.65 (s, 3H) 4.0–4.2 (m, 1H) 5.3–5.5 (m, 1H) 5.62 (dd, J=6.3 & 15.2 Hz, 1H) 7.0–7.3 (m, 5H)

Example 38

Synthesis of methyl(11R,12S,13E)-9-butyryloxy-11 15-dihydroxy-17-phenyl-18,19,20-trinor-7-thiaprosta-8,13-dienoate ($R^1$=Pr, $R^2$=H, $R^3$=H, $R^4$=2-phenylethyl, W=OH, X—Y=$CH_2$—$CH_2$, Z=$CO_2$Me, n=0, ═=trans-CH═CH)

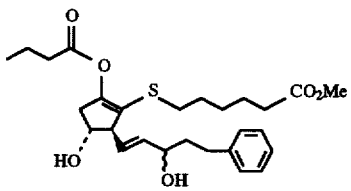

Using as the material and reagent a hydrogen fluoride-pyridine solution (0.5 ml) and methyl (11R,12S,13E)-9-butyryloxy-11,15-bis(tert-butyldimethylsiloxy)-17-phenyl-18,19,20-trinor-7-thiaprosta-8,13-dienoate (300 mg), the same procedure as in Example 2 was performed to separately obtain two stereoisomers of methyl(11R,13E)-9-butyryloxy-11,15dihydroxy-17-phenyl-18,19,20-trinor-7-thiaprosta-8,13-dienoate different at the 15-position. (Low polarity compound: 71 mg, 34% high polarity compound: 101 mg, 50%)

[Low polarity compound]

$^1$H-NMR (270 MHz, δppm, $CDCl_3$) 1.01 (t, J=7.2 Hz, 3H) 1.2–1.9 (m, 10H) 2.15 (d, J=6.3 Hz, 1H) 2.29 (d, J=7.3 Hz, 2H) 2.43 (t, J=7.5 Hz, 2H) 2.5–2.8 (m, 4H) 2.96 (dd, J=6.3 & 16.5 Hz, 1H) 3.23 (d, J=7.9 Hz, 1H) 3.66 s, 3H) 4.1–4.2 (m, 2H) 5.59 (dd, J=7.9 & 15.5 Hz, 1H) 5.76 (dd, J=6.0 & 15.5 Hz, 1H) 7.1–7.3 (m, 5H)

[High polarity compound]

$^1$H-NMR (270 MHz, δppm, $CDCl_3$) 1.01 (t, J=7.4 Hz, 3H) 1.2–2.0 (m, 10H) 2.28 (t, J=7.6 Hz, 2H) 2.43 (t, J=7.6 Hz, 2H) 2.5–2.8 (m, 5H) 2.94 (ddd, J=6.6 & 16.5 Hz, 1H) 3.22 (dd, J=2.7 & 8.2 Hz, 1H) 3.67 (s, 3H) 4.1–4.2 (m, 2H) 5.58 (dd, J=8.3 & 15.5 Hz, 1H) 5.73 (dd, J=6.5 & 15.5 Hz, 1H) 7.1–7.4 (m, 5H)

Example 39

Synthesis of methyl(11R,12S,13E)-9-butyryloxy-11-tert-butyldimethylsiloxy-15-hydroxy-16-phenyl-17,18,19,20-tetranor-7-thiaprosta-8,13-dienoate ($R^1$=Pr, $R^2$=H, $R^3$=H, $R^4$=Benzyl, W=$^t$BuMe$_2$SiO, X—Y=CH$_2$—CH$_2$, Z=CO$_2$Me, n=0, ==trans-CH=CH)

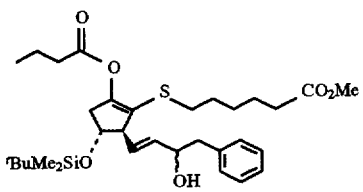

Chromium(II) chloride (344 mg) and nickel chloride (0.3 mg) were suspended in dimethylformamide (3.0 then a dimethylformamide solution (2.0 ml) of (3S,4R)-4-(tert-butyldimethylsiloxy)-1-butyryloxy-2-(5-methoxycarbonylpentylthio)-3-(trans-2-iodovinyl)-1-cyclopentene (418 mg) and phenylacetoaldehyde (168 mg) was added while stirring at room temperature. The mixture was further stirred as is at room temperature for a further 2.5 hours, then water (70 ml) was added, then organic layer was separated, then extraction was performed from the aqueous layer by ether (50 ml×3). The extracts were combined with the organic layer and 10 were washed by saturated sodium chloride solution, then was dried over anhydrous magnesium sulfate. This was concentrated under reduced pressure, then the resultant yellow oil was purified by silica gel column chromatography (15% ethyl acetate/hexane) to obtain methyl(11R,12S,13E)-9-butyryloxy-11-tert-butyldimethylsiloxy-15-hydroxy-16-phenyl-17,18,19,20-tetranor-7-thiaprosta-8,13-dienoate (268 mg, 65%).

Note that the thus obtained methyl(11R,12S,13E)-9-butyryloxy-11-tert-butyldimethylsiloxy-15-hydroxy-16-phenyl-17,18,19,20-tetranor-7-thiaprosta-8,13-dienoate is a diastereomer mixture of mixed stereo isomers of different hydroxyl groups at the 15-position.

$^1$H-NMR (270 MHz, δppm, CDCl$_3$) 0.04 (s, 6H) 0.88 (s, 9H) 1.01 (t, J=7.3 Hz, 3H) 1.2–1.75 (m, 10H) 2.30 (t, J=7.4 Hz, 2H) 2.35–2.45 (m, 1H) 2.42 (t, J=7.3 Hz, 2H) 2.7–2.9 (m, 3H) 3.1 (d-like, J=8.0 Hz, 1H) 3.66 (s, 3H) 4.0–4.1 (m, 1H) 4.3–4.4 (m, 1H) 5.45–5.6 (m, 1H) 5.65–5.8 (m, 1H) 7.1–7.3 (m, 5H)

Example 40

Synthesis of methyl(11R,12S,13E)-9-butyryloxy-11,15-dihydroxy-16-phenyl-17,18,19,20-tetranor-7-thiaprosta-8,13-dienoate ($R^1$=Pr, $R^2$=H, $R^3$=H, $R^4$=benzyl, W=OH, X—Y=CH$_2$—CH$_2$, Z=CO$_2$Me, n=0, ==trans-CH=CH)

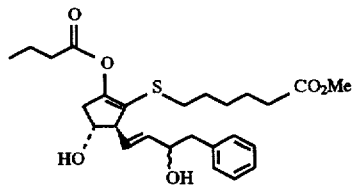

Using as the material and reagent a hydrogen fluoride-pyridine solution (0.5 ml) and methyl(11R,12S,13E)-9-butyryloxy-11-tert-butyldimethylsiloxy-15-hydroxy-16-phenyl-17,18,19,20-tetranor-7-thiaprosta-8,13-dienoate (260 mg), the same procedure was performed as in Example 2 to separately obtain two stereoisomers of methyl(11R,12S,13E)-9-butyryloxy-11,15-dihydroxy-16-phenyl-17,18,19,20-tetranor-7-thiaprosta-8,13-dienoate different at the 15-position. (Low polarity compound: 75 mg, 36%; high polarity compound: 79 mg, 38%)

[Low polarity compound]

$^1$H-NMR (270 MHz, δppm, CDCl$_3$) 1.01 (t, J=7.4 Hz, 3H) 1.3–1.8 (m, 8H) 1.86 (br.d, J=3.9 Hz, 1H) 2.06 (d-like, J=6.3 Hz, 1H) 2.31 (t, J=7.3 Hz, 2H) 2.4–2.8 (m, 3H) 2.43 (t, J=7.3 Hz, 2H) 2.85 (dd, J=2.5 & 6.8 Hz, 2H) 2.93 (d, J=8.0 Hz, 1H) 3.18 (dd, J=1.9 & 8.1 Hz, 1H) 3.66 (s, 3H) 3.99 (m, 1H) 4.38 (m, 1H) 5.50 (ddd, J=1.0 & 8.2 & 15.5 Hz, 1H) 5.75 (ddd, J=0.7 & 6.3 & 15.5 Hz, 1H) 7.1–7.4 (m, 5H)

[High polarity compound]

$^1$H-NMR (270 MHz, δppm, CDCl$_3$) 1.01 (t, J=7.4 Hz, 3H) 1.3–1.8 (m, 8H) 1.82 (br, 1H) 2.3 (br, 1H) 2.30 (t, J=7.3 Hz, 2H) 2.4–2.7 (m, 3H) 2.44 (t, J=7.2 Hz, 2H) 2.7–3.0 (m, 3H) 3.19 (d-like, J=6.2 Hz, 1H) 3.66 (s, 3H) 4.08 (br, 1H) 4.38 (m, 1H) 5.57 (dd, J=7.2 & 15.5 Hz, 1H) 5.75 (dd, J=6.0 & 15.5 Hz, 1H) 7.1–7.4 (m, 5H)

Example 41

Synthesis of methyl(11R,12S,13E)-9-butyryloxy-11-tert-butyldimethylsiloxy-15-hydroxy-16,16,20-trimethyl-7-thiaprosta-8,13-dienoate ($R^1$=Pr, $R^2$=H, $R^3$=H, $R^4$=1,1-dimethylhexyl, W=$^t$BuMe$_2$SiO, X—Y=CH$_2$—CH$_2$, Z=CO$_2$Me, n=0, ==trans-CH=CH)

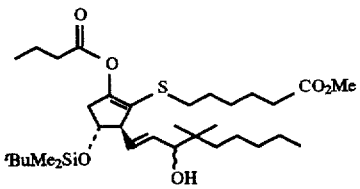

Using as the materials and reagents chromium(II) chloride (344 mg), nickel chloride (0.3 mg), (3S,4R)-4-(tert-butyldimethylsiloxy)-1-butyryloxy-2-(5-methoxycarbonylpentylthio)-3-(trans-2-iodovinyl)-1-cyclopente (418 mg), and 2,2-dimethylpentane aldehyde (199 mg), the same procedure was performed as in Example 39 to obtain methyl(11R,12S,13E)-9-butyryloxy-11-tert-butyldimethylsiloxy-15-hydroxy-16,16,20-trimethyl-7-thiaprosta-8,13-dienoate (103 mg, 24%)

Note that the thus obtained methyl(11R,12S,13E)-9-butyryloxy-11-tert-butyldimethylsiloxy-15-hydroxy-16,16,20-trimethyl-7-thiaprosta-8,13-dienoate is a diastereomer mixture of mixed stereoisomers of different hydroxyl groups at the 15-position.

$^1$H-NMR (270 MHz, δppm, CDCl$_3$) 0.05 (s, 6H) 0.85 (s, 3H) 0.88 (s, 3H) 0.90 (t, J=7.7 Hz, 3H) 0.91 (s, 9H) 1.1–1.8 (m, 16H) 2.30 (t, J=7.4 Hz, 2H) 2.3–2.7 (m, 3H) 2.42 (t, J=7.3 Hz, 2H) 2.8–2.9 (m, 1H) 3.1–3.2 (m, 1H) 3.67 (s, 3H) 3.83 (d-like, J=6.9 Hz, 1H) 4.0–4.2 (m, 1H) 5.4–5.6 (m, 1H) 5.6–5.8 (m, 1H)

Example 42

Synthesis of methyl(11R,12S,13E)-9-butyryloxy-11,15-dihydroxy-16,16,20-trimethyl-7-thiaprosta-8,13-dienoate ($R^1$=Pr, $R^2$=H, $R^3$=H, $R^4$=1,1-dimethylhexyl, W=OH, X—Y=$CH_2$—$CH_2$, Z=$CO_2Me$, n=0, ═=trans-CH═CH)

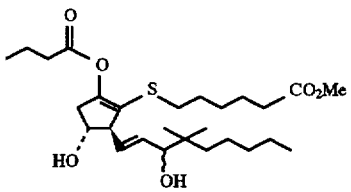

Using as the materials a hydrogen fluoride-pyridine solution (0.25 ml) and methyl(11R,12S,13E)-9-butyryloxy-11-tert-butyldimethylsiloxy-15-hydroxy-16,16,20-trimethyl-7-thiaprosta-8,13-dienoate (100 mg), the same procedure as in Example 2 was performed to separately obtain two stereoisomers of methyl(11R,12S,13E)-9-butyryloxy-11,15-dihydroxy-16,16,20-trimethyl-7-thiaprosta-8,13-dienoate different at the 15-position. (Low polarity compound: 26 mg, 33%; high polarity compound: 28 mg, 35%)

[Low polarity compound]

$^1$H-NHR (270 MHz, δppm, $CDCl_3$) 0.85 (s, 3H) 0.8–0.9 (m, 3H) 0.88 (s, 3H) 1.00 (t, J=7.4 Hz, 3H) 1.1–1.8 (m, 16H) 2.11 (d-like, J=7.0 Hz, 1H) 2.31 (t, J=7.3 Hz, 2H) 2.4–2.8 (m, 3H) 2.44 (t, J=7.3 Hz, 2H) 2.97 (ddd, J=1.3 & 6.3 & 16.5 Hz, 1H) 3.25 (d-like, J=8.3 Hz, 1H) 3.67 (s, 3H) 3.8–3.9 (m, 1H) 4.1–4.2 (m, 1H) 5.58 (dd, J=7.9 & 15.5 Hz, 1H) 5.79 (dd, J=6.9 & 15.5 Hz, 1H)

[High polarity compound]

$^1$H-MNR (270 MHz, δppm, $CDCl_3$) 0.85 (s, 3H) 0.8–0.9 (m, 3H) 0.88 (s, 3H) 1.01 (t, J=7.4 Hz, 3H) 1.1–1.8 (m, 16H) 2.18 (d-like, J=7.3 Hz, 1H) 2.31 (t, J=7.3 Hz, 2H) 2.4–2.8 (m, 3H) 2.43 (t, J=7.3 Hz, 2H) 2.97 (ddd, J=1.3 & 6.6 & 16.5 Hz, 1H) 3.23 (d-like, J=7.6 Hz, 1H) 3.67 (s, 3H) 3.82 (d-like, J=6.9 Hz, 1H) 4.15 (m, 1H) 5.56 (dd, J=7.6 & 15.5 Hz, 1H) 5.77 (dd, J=6.7 & 15.5 Hz, 1H)

Example 43

Synthesis of methyl(11R,12S,13E)-9-butyryloxy-11-tert-butyldimethylsiloxy-15-hydroxy-16-methyl-16-phenyl-18,19,20-trinor-7-thiaprosta-8,13-dienoate ($R^1$=Pr, $R^2$=H, $R^3$=H, $R^4$=1-ph-1-Me-ethyl, W=$^tBuMe_2SiO$, X—Y=$CH_2$—$CH_2$, Z=$CO_2Me$, n=0, ═=trans-CH═CH)

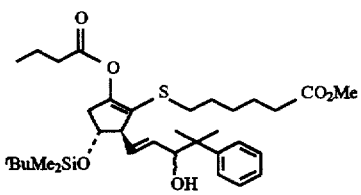

Using as the materials and reagents chromium(II) chloride (630 mg), nickel chloride (0.1 mg), (3S,4R)-4-(tert-butyldimethylsiloxy)-1-butyryloxy-2-(5-methoxycarbonylpentylthio)-3-(trans-2-iodovinyl)-1-cyclopentene (418 mg), and dimethylphenylacetoaldehyde (311 mg), the same procedure was performed as in Example 39 to obtain methyl(11R,12S,13E)-9-butyryloxy-11-tert-butyldimethylsiloxy-15-hydroxy-16-methyl-16-phenyl-18,19,20-trinor-7-thiaprosta-8,13-dienoate (214 mg, 24%).

Note that the thus obtained methyl(11R,12S,13E)-9-butyryloxy-11-tert-butyldimethylsiloxy-15-hydroxy-16-methyl-16-phenyl-18,19,20-trinor-7-thiaprosta-8,13-dienoate is a diastereomer mixture of mixed stere isomers of different hydroxyl groups at the 15-position.

$^1$H-NMR (270 MHz, δppm, $CDCl_3$) 0.02 (s, 3H) 0.03 (s, 3H) 0.84 (s), 0.87 (s) ..... 9H 1.00 (t, J=7.4 Hz, 3H) 1.2–1.8 (m, 8H) 1.34 (s, 3H) 1.35 (s, 3H) 2.29 (t, J=7.3 Hz, 2H) 2.3–2.7 (m, 3H) 2.43 (t, J=7.3 Hz, 2H) 2.87 (ddd, J=1.3 & 6.9 & 16.5 Hz, 1H) 3.09 (br.d, J=7.3 Hz, 1H) 3.66 (s, 3H) 5.4–5.7 (m, 2H) 7.1–7.5 (m, 5H)

Example 44

Synthesis of methyl(11R,12S,13E)-9-butyryloxy-11,15-dihydroxy-16-methyl-16-phenyl-18,19,20-trinor-7-thiaprosta-8,13-dienoate ($R^1$=Pr, $R^2$=H, $R^3$=H, $R^4$=1-Ph-1-Me-ethyl, W=OH, X—Y=$CH_2$—$CH_2$, Z=$CO_2Me$, n=0, ═=trans-CH═CH)

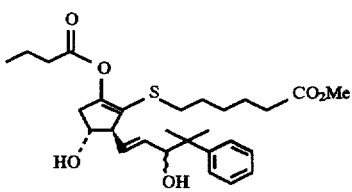

A pyridinium p-toluene sulfonate polymer bound (280 mg) was added to a methanol (4.0 ml) solution of methyl (11R,12S,13E)-9-butyryloxy-11-tert-butytdimethylsiloxy-15-hydroxy-16-methyl-16-phenyl-18,19,20-trinor-7-thiaprosta-8,13-dienoate (180 mg), then the mixture was stirred at 40° C. for two hours. The reaction solution was filtered to remove the insolubles, then the filtrate was concentrated under reduced pressure and was purified by silica gel column chromatography (40% ethyl acetate/hexane) to separately obtain two stereo isomers of methyl (11R,12S,13E)-9-butyryloxy -11,15-dihydroxy-16-methyl-16-phenyl-18,19,20-trinor-7-thiaprosta-8,13-dienoate different at the 15-position. (Low polarity compound: 34 mg, 23%; high polarity compound: 48 mg, 33%)

[Low polarity compound]

$^1$H-NMR (270 MHz, δppm, $CDCl_3$) 1.00 (t, J=7.4 Hz, 3H) 1.34 (s, 3H) 1.37 (s, 3H) 1.2–1.8 (m, 8H) 1.98 (d-like, J=7.0 Hz, 1H) 2.30 (t, J=7.4 Hz, 2H) 2.4–2.7 (m, 3H) 2.42 (t, J=7.4 Hz, 1H) 2.88 (ddd, J=1.3 & 6.3 & 16.5 Hz, 1H) 3.13 (dd, J=3.0 & 8.2 Hz, 1H) 3.66 (s, 3H) 3.9–4.0 (m, 1H) 4.1–4.3 (m, 1H) 5.46 (dd, J=8.2 & 15.5 Hz, 1H) 5.60 (dd, J=6.2 & 15.5 Hz, 1H) 7.1–7.5 (m, 5H)

[High polarity compound]

$^1$H-NMR (270 MHz, δppm, $CDCl_3$) 1.00 (t, J=7.4 Hz, 3H) 1.34 (s, 3H) 1.35 (s, 3H) 1.2–1.8 (m, 8H) 2.18 (br. 1H) 2.30 (t, J=7.4 Hz, 2H) 2.4–2.7 (m, 3H) 2.43 (t, J=7.4 Hz, 1H) 2.90 (dd, J=6.3 & 16.5 Hz, 1H) 3.16 (d-like, J=7.2 Hz, 1H) 3.66 (s, 3H) 4.05 (br. 1H) 4.13 (br. 1H) 5.4–5.7 (m, 2H) 7.1–7.5 (m, 5H)

Example 45

Synthesis of methyl(11R,12S,13E,16R)-9-butyryloxy-11-tert-butyldimethylsiloxy-15-hydroxy-16-phenyl-18,19,20-trinor-7-thiaprosta-8,13-dienoate (R$^1$=Pr, R$^2$=H, R$^3$=H, R$^4$=1-ph-ethyl, W=$^t$BuMe$_2$SiO, X—Y=CH$_2$—CH$_2$, Z=CO$_2$Me, n=0, ==trans-CH=CH)

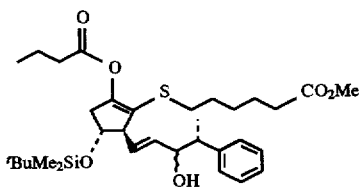

Using as the materials and reagents chromium(II) chloride (430 mg), nickel chloride (0.1 mg), (3S,4R)-4-(tert-butyldimethylsiloxy)-1-butyryloxy-2-(5-methoxycarbonylpentylthio)-3-trans-2-iodovinyl)-1-cyclopentene (418 mg), and (R)-methylphenylacetoaldehyde (186 mg), the same procedure was performed as in Example 39 to obtain methyl(11R,12S,13E,16R)-9-butyryloxy-11-tert-butyldimethylsiloxy-15-hydroxy-16-phenyl-18,19,20-trinor-7-thiaprosta-8,13-dienoate (259 mg, 61%).

Note that the methyl(11R,12S,13E,16R)-9-butyryloxy11-tert-butyldimethylsiloxy-15-hydroxy-16-phenyl-18,19,20-trinor-7-thiaprosta-8,13-dienoate thus obtained is a diastereomer mixture of mixed stereo isomers of different hydroxyl groups at the 15-position.

$^1$H-NMR (400 MHz, δppm, CDCl$_3$) −0.01 (s, 3H) 0.03 (s, 3H) 0.84 (s), 0.87 (s) ...... 9H 0.98 (t, J=7.4 Hz, 3H) 1.2–1.8 (m, 11 H) 2.28 (t, J=7.3 Hz, 2H) 2.3–3.2 (m, 6H) 2.41 (t, J=7.3 Hz, 2H) 3.65 (s, 3H) 3.95 (m, 1H) 4.2 (m, 1H) 5.4–5.8 (m, 2H) 7.1–7.4 (m, 5H)

Example 46

Synthesis of methyl(11R,12S,13E,16R)-9-butyryloxy-11,15-dihydroxy-16-phenyl-18,19,20-trinor-7-thiaprosta-8,13-dienoate (R$^1$=Pr, R$^2$=H, R$^3$= H, R$^4$=1-Ph-ethyl, W=OH, X—Y=CH$_2$—CH$_2$, Z=CO$_2$Me, n=0, ==trans-CH=CH)

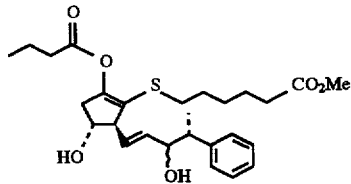

Using as the material and reagent a hydrogen fluoride-pyridine solution (0.5 ml) and methyl(11R,12S,13E,16R)-9-butyryloxy-11-tert-butyldimethylsiloxy-15-hydroxy-16-phenyl-18,19,20-trinor-7-thiaprosta-8,13-dienoate (247 mg), the same procedure as in Example 2 was performed to separately obtain two stereoisomers of methyl(11R,12S,13E,16R)-9-butyryloxy-11,15-dihydroxy-16-phenyl-18,19,20-trinor-7-thiaprosta-8,13-dienoate different at the 15-position. (Low polarity compound: 28 mg, 19%; high polarity compound: 109 mg, 54%)

[Low polarity compound]

$^1$H-NMR (400 MHz, δppm, CDCl$_3$) 1.00 dr, J=6.3 & 7.4 Hz, 3H) 1.2–1.8 (m, 8H) 1.27 (d, J=6.8 Hz, 3H) 2.3–3.3 (m, 8H) 2.32 (t, J=7.3 Hz, 2H) 3.66 s), 3.67 (s) ......3H 3.7–4.2 (m, 2H) 5.37 (dd, J=8.8 & 15.6 Hz, 0.5H) 5.5–5.7 (m, 1H) 5.72 (dd, J=8.8 & 15.6 Hz, 0.5H) 7.1–7.4 (m, 5H)

[High polarity compound]

$^1$H-NMR (400 MHz, δppm, CDCl$_3$) 1.01 (t, J=7.3 Hz, 3H) 1.3–1.7 (m, 6H) 1.33 (d, J=6.8 Hz, 3H) 1.74 (d, J=7.3 Hz, 3H) 2.24 (br. 1H) 2.30 (t, J=7.3 Hz, 2H) 2.3–2.5 (m, 2H) 2.43 (t, J=7.3 Hz, 2H) 2.58 (dq, J=7.8 & 6.3 Hz, 1H) 2.83 (ddd, J=1.4 & 6.7 & 16.5 Hz, 1H) 2.91 (t-like, J=6.5 Hz, 1H) 3.13 (br.d, J=5.5 Hz, 1H) 3.66 (s, 3H) 3.96 (br. 1H) 4.22 (br.t, J=5.8 Hz, 1H) 5.50 (dd, J=7.5 & 15.5 Hz, 1H) 5.58 (dd, J=6.4 & 15.5 Hz, 1H) 7.1–7.4 (m, 5H)

Example 47

Synthesis of methyl(11R,12S,13E,16S)-9-butyryloxy-11-tert-butyldimethylsiloxy-15-hydroxy-16-phenyl-18,19,20-trinor-7-thiaprosta-8,13-dienoate (R$^1$=Pr R$^2$=H R$^3$=H, R$^4$=1-Ph-ethyl W=$^t$BuMe$_2$SiO X—Y=CH$_2$—CH$_2$, Z=CO$_2$Me, n=0, ==trans-CH=CH )

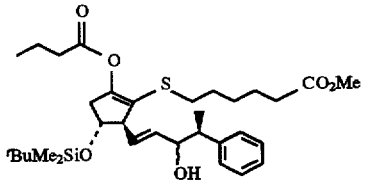

Using as the materials and reagents chromium(II) chloride (789 mg), nickel chloride (0.1 mg), (3S,4R)-4-(tert-butyldimethylsiloxy)-1-butyryloxy-2-(5-methoxycarbonylpentylthio)-3-(trans-2-iodovinyl)-1-cyclopentene (418 mg), and (S)-methylphenylacetoaldehyde (186 mg), the same procedure was performed as in Example 39 to obtain methyl(11R,12S,13E,16S)-9-butyryloxy-11-tert-butyldimethylsiloxy-15-hydroxy-16-phenyl-18,19,20-trinor-7-thiaprosta-8,13-dienoate (276 mg, 65%).

Note that the thus obtained methyl(11R,12S,13E,16S)-9-butyryloxy-11-tert-butyldimethylsiloxy-15-hydroxy-16-phenyl-18,19,20-trinor-7-thiaprosta-8,13-dienoate is a diastereomer mixture of mixed stereo isomers of different hydroxyl groups at the 15-position.

$^1$H-NMR (400 MHz, δppm, CDCl$_3$) 0.00 (s, 6H) 0.86 (s, 9H) 1.00 (t, J=7.5 Hz, 3H) 1.2–1.8 (m, 8H) 1.51 (d, J=1.0 Hz, 3H) 2.29 (t, J=7.3 Hz, 2H) 2.3–3.2 (m, 6H) 2.42 (t, J=7.3 Hz, 2H) 3.66 (s, 3H) 3.97 (m, 1H) 4.23 (m, 1H) 5.47 (m, 1H) 5.5–5.8 (m, 1H) 7.1–7.4 (m, 5H)

Example 48

Synthesis of methyl(11R,12S,13E,16S)-9-butyryloxy-11,15-dihydroxy-16-phenyl-18,19,20-trinor-7-thiaprosta-8,13-dienoate (R¹=Pr, R²=H, R³=H, R⁴=1-Ph-ethyl, W=OH, X—Y=CH₂—CH₂, Z=CO₂Me, n=0, ═=trans-CH═CH)

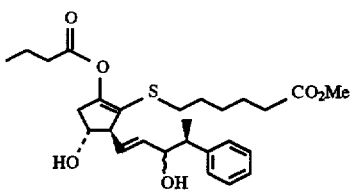

Using as the material and reagent a hydrogen fluoride-pyridine solution (0.5 ml) and methyl(11R,12S,13E,16S)-9-butyryloxy-11-tert-butyldimethylsiloxy-15-hydroxy-16-phenyl-18,19,20-trinor-7-thiaprosta-8,13-dienoate (270 mg), the same procedure as in Example 2 was performed to separately obtain two stereo isomers of methyl(11R,12S,13E,16S)-9-butyryloxy-11,15-dihydroxy-16-phenyl-18,19,20-trinor-7-thiaprosta-8,13-dienoate different at the 15-postion. (Low polarity compound: 142 mg, 64%; high polarity compound: 38 mg, 17%)

[Low polarity compound]
¹H-NMR (270 MHz, δppm, CDCl₃) 1.00 (t, J=7.3 Hz, 3H) 1.3–1.8 (m, 8H) 1.36 (d, J=7.0 Hz, 3H) 1.85 (br, 1H) 2.30 (t, J=7.3 Hz, 2H) 2.3–2.7 (m, 3H) 2.41 (t, J=7.3 Hz, 2H) 2.7–2.9 (m, 2H) 3.07 (dd, J=3.0 & 8.6 Hz, 1H) 3.67 (s, 3H) 3.78 (br, 1H) 4.19 (t-like, J=5.0 Hz, 1H) 5.37 (dd, J=8.2 & 15.5 Hz, 1H) 5.58 (dd, J=6.6 & 15.5 Hz, 1H) 7.1–7.4 (m, 5H)

[High polarity compound]
¹H-NMR (270 MHz, δppm, CDCl₃) 1.01 (t, J=7.3 Hz, 3H) 1.2–1.8 (m, 8H) 1.26 (d, J=7.0 Hz, 3H) 2.31 (t, J=7.4 Hz, 2H) 2.3–3.0 (m, 5H) 2.44 (t, J=7.3 Hz, 2H) 3.1–3.3 (m, 1H) 3.66 (s, 3H) 4.0–4.3 (m, 2H) 5.4–5.8 (m, 2H) 7.1–7.4 (m, 5H)

Example 49

Synthesis of methyl(11R,12S,13E)-9-butyryloxy-11-tert-butyldimethylsiloxy-15-hydroxy-16,16-diphenyl-17,18,19,20-tetranor-7-thiaprosta-8,13-dienoate (R¹=Pr, R²=H, R³=H, R⁴=Benzhydryl, W=ᵗBuMe₂SiO, X—Y=CH₂—CH₂, Z=CO₂Me, n=0, ═=trans-CH═CH)

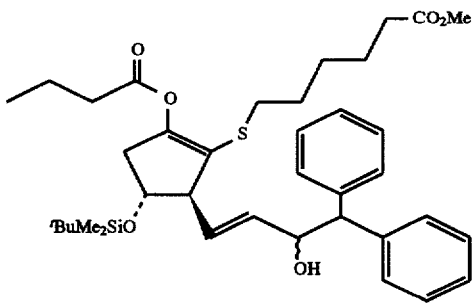

Using as the materials and reagents chromium chloride(II) (550 mg), nickel chloride (0.3 mg), (3S,4R)-4-(tert-butyldimethylsiloxy)-1-butyryloxy-2-(5-methoxycarbonylpentylthio)-3-(trans-2-iodovinyl)-1-cyclopentene (418 mg), and diphenylacetoaldehyde (275 mg), the same procedure was performed as in Example 39 to obtain methyl(11R,12S,13E)-9-butyryloxy-11-tert-butyldimethylsiloxyl-15-hydroxy-16,16-diphenyl-17,18,19,20-tetranor-7-thiaprosta-8,13-dienoate (137 mg.

Note that the methyl(11R,12S,13E)-9-butyryloxy-11-tert-butyldimethylsiloxy-15-hydroxy-16,16-diphenyl-17,18,19,20-tetranor-7-thiaprosta-8,13-dienoate thus obtained is a diastereomer mixture of mixed stereo isomers of different hydroxyl groups at the 15-position.

¹H-NMR (270 MHz, δppm, CDCl₃) −0.04 (s, 3H) −0.03 (s, 3H) 0.84 (d, J=3.0 Hz, 9H) 1.26 (t, J=7.1 Hz, 3H) 1.3–1.8 (m, 9H) 2.2–2.9 (m, 8H) 3.01 (br.d, J=6.6 Hz, 1H) 3.67 (s, 3H) 3.8–4.1 (m, 2H) 4.8–5.0 (m, 1H) 5.4–5.8 (m, 2H) 7.1–7.4 (m,10H)

Example 50

Synthesis of methyl(11R,12S,13E)-9-butyryloxy-11,15-dihydroxy-16,16-diphenyl-17,18,19,20-tetranor-7-thiaprosta-8,13-dienoate (R¹=Pr, R²=H, R³=H, R⁴=Benzhydryl, W=OH, X—Y=CH₂—CH₂, Z=CO₂Me, n=0, ═=trans-CH═CH)

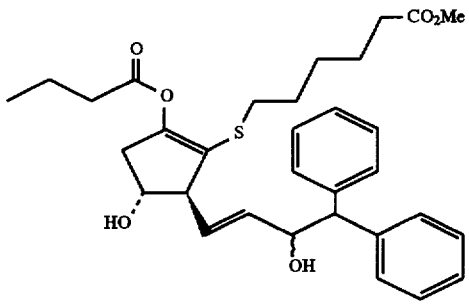

Using as the material and reagent a hydrogen fluoride-pyridine solution (0.25 ml) and methyl(11R,12S,13E)-9-butyryloxy-11-tert-butyldimethylsiloxyl-15-hydroxy-16,16-diphenyl-17,18,19,20-tetranor-7-thiaprosta-8, and 13-dienoate (137 mg), the same procedure as in Example 2 was performed to separately obtain two stereo isomers of methyl(11R,12S,13E)-9-butyryloxy-11,15-dihydroxy-16,16-diphenyl-17,18,19,20-tetranor-7-thiaprosta-8,13-dienoate different at the 15-position. (Low polarity compound: 31 mg, 27%; high polarity compound: 32 mg, 28%)

[Low polarity compound]
¹H-NMR (270 MHz, δppm, CDCl₃) 0.99 (t, J=7.2 Hz, 3H) 1.3–1.9 (m, 8H) 2.29 (t, J=7.2 Hz, 2H) 2.2–2.8 (m, 5H) 2.41 (t, J=7.3 Hz, 1H) 3.04 (ddd, J=1.4 & 3.6 & 8.6 Hz, 1H) 3.66 (s, 3H) 3.99 (d, J=8.9 Hz, 1H) 4.8–5.0 (m, 1H) 5.45 (dd, J=8.5 & 15.4 Hz, 1H) 5.64 (dd, J=6.6 & 15.4 Hz, 1H) 7.1–7.5 (m,10H)

[High polarity compound]
¹H-NMR (270 MHz, δppm, CDCl₃) 1.00 (t, J=7.3 Hz, 3H) 1.2–1.9 (m, 8H) 2.28 (t, J=7.3 Hz, 2H) 2.1–2.5 (m, 4H) 2.42 (t, J=7.2 Hz, 2H) 2.73 (dd, J=6.5 & 16.5 Hz, 1H) 3.08 (d-like, J=5.0 Hz, 1H) 3.66 (s, 3H) 3.8–3.9 (br, 1H) 3.99 (d, J=8.0 Hz, 1H) 4.8–4.9 (m, 1H) 5.63 (t-like, J=5.3 Hz, 2H) 7.1–7.4 (m, 10H)

Example 51

Synthesis of methyl(11R,12S,13E,15S,17R)-9-butyryloxy-11,15-bis(tert-butyldimethylsiloxy)-17,20-dimethyl-3-oxa-7-thiaprosta-8,13-dienoate ($R^1$= Pr, $R^2$=$^t$BuMe$_2$Si, $R^3$=H, $R^4$=2-Me-hexyl, W=$^t$BuMe$_2$SiO, X—Y=O—CH$_2$, Z=CO$_2$Me, n=0, ═=trans-CH═CH)

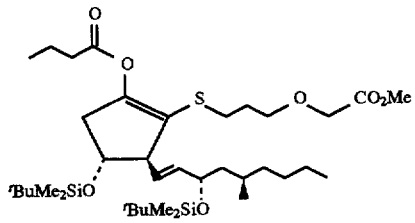

Using as the materials and reagents (1E,3S,5R)-1-iodo-3-(tert-butyldimethylsiloxy)-5-methyl-1-nonene (476 mg, 1.2 mmol), tert-butyllithium (1.54 mol/l, 1.56 ml, 2.4 mmol, 1-hexynylcopper (174 mg), hexamethylphosphorous triamide (436 µl), (4R)-4-(tert-butyldimethylsiloxy)-2-(5-methoxycarbonyl-4-oxa-pentylthio)-2-cyclopenten-1-one (375 mg, 1.0 mmol), and butyric anhydride (441 µl), the same procedure was performed as in Example 1 to obtain methyl(11R,12S,13E,15S,17R)-9-butyryloxy-11,15-bis(tert-butyldimethylsiloxy)-17,20-dimethyl-3-oxa-7-thiaprosta-8,13-dienoate (524 mg, 73%).

$^1$H-NMR (270 MHz, δppm, CDCl$_3$) 0.04 (s), 0.05 ...... 12H 0.8–1.0 (m, 6H) 0.87 (s, 9H) 0.89 (s, 9H) 1.00 (t, J=7.3 Hz, 3H) 1.0–1.9 (m, 13H) 2.3–2.5 (m, 1H) 2.42 (t, J=7.4 Hz, 2H) 2.5–2.8 (m, 2H) 2.92 (dd, J=6.8 & 16.3 Hz, 1H) 3.13 (d, J=6.3 Hz, 1H) 3.5–3.6 (m, 2H) 3.75 (s, 3H) 4.07 (s, 2H) 4.1–4.2 (m, 1H) 5.43 (dd, J=8.6 & 15.5 Hz, 1H) 5.63 (dd, J=6.1 & 15.3 Hz, 1H)

Example 52

Synthesis of methyl(11R,12S,13E,15S,17R)-9-butyryloxy-11,15-dihydroxy-17,20-dimethyl-3-oxa-7-thiaprosta-8,13-dienoate ($R^1$=Pr, $R^2$=H, $R^3$=H, $R^4$=2-Me-hexyl, W=OH, X—Y=O—CH$_2$, Z=CO$_2$Me, n=0, ═=trans-CH═CH)

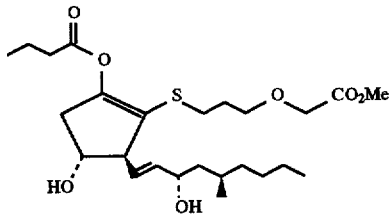

A hydrogen fluoride-pyridine solution (50 µl) was added to a solution of ice-cooled acetonitrile (0.5 ml) and pyridine (50 µl), then a pyridine (50 µl) solution of methyl(11R,12S,13E,15S,17R)-9-butyryloxy-11,15-bis(tert-butyldimethylsiloxyl)-17,20-dimethyl-3-oxa-7-thiaprosta-8,13-dienoic acid (52 mg) was added. The ice bath was removed, then the solution was stirred for 20 hours while raising it to room temperature. The reaction solution was poured into a mixture of ethyl acetate and saturated sodium hydrogen carbonate. The desired substance was extracted from the mixture by ethyl acetate. The extract was washed with saturated sodium chloride solution, then was dried over anhydrous sodium sulfate. This solution was concentrated under reduced pressure, then was purified by a preparative TLC (Merck TLC plate silica gel 60 F$_{254}$, 20×20 cm, layer thickness 0.25 mm, 3 pieces, ethyl acetate:hexane=4:1) to obtain methyl(11R,12S,13E,15S,17R)-9-butyryloxy-11,15-dihydroxy-17,20-dimethyl-3-oxa-7-thiaprosta-8,13-dienoate (22 mg, 63%).

$^1$H-NMR (270 MHz, δppm, CDCl$_3$) 0.8–1.0 (m, 6H) 1.00 (t, J=7.4 Hz, 3H) 1.0–1.9 (m, 13H) 2.4–2.6 (m, 1H) 2.43 (t, J=7.3 Hz, 2H) 2.6–2.9 (m, 2H) 2.92 (dd, J=6.6 & 16.5 Hz, 1H) 3.27 (d, J=8.2 Hz, 1H) 3.5–3.7 (m, 2H) 3.75 (s, 3H) 4.07 (s, 2H) 4.1–4.3 (m, 1H) 5.58 (dd, J=8.1 & 15.3 Hz, 1H) 5.72 (dd, J=6.1 & 15.3 Hz, 1H)

Example 53

Synthesis of methyl(11R,12S,13E,15S)-9-butyryloxy-11,15-bis(tert-butyldimethylsiloxy)-16-phenyl-17,18,19,20-tetranor-3-oxa-7-thiaprosta-8,13-dienoate ($R^1$=Pr, $R^2$=$^t$BuMe$_2$Si, $R^3$=H, $R^4$=benzyl, W=$^t$BuMe$_2$SiO, X—Y=O—CH$_2$, Z=CO$_2$Me, n=0, ═=trans-CH═CH)

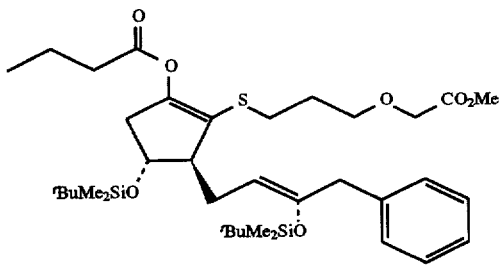

Using as the materials and reagents (1E,3S)-1-iodo-3-(tert-butyldimethylsiloxy)-4-phenyl-1-butene (466 mg, 1.2 mmol), tert-butyllithium (1.54 mol/l, 1.56 ml, 2.4 mmol), 1-hexynylcopper (174 mg), hexamethylphosphorous triamide (436 µl), (4R)-4-(tert-butyldimethylsiloxy)-2-(5-methoxycarbonyl-4-oxa-pentylthio)-2-cyclopenten-1-one (375 mg, 1.0 mmol), and butyric anhydride (442 µl), the same procedure was performed as in Example 1 to obtain methyl(11R,12S,13E,15S)-9-butyryloxy-11,15-bis(tert-butyldimethylsiloxy)-16-phenyl-17,18,19,20-tetranor-3-oxa-7-thiaprosta-8,13-dienoate (238 mg, 34%).

$^1$H-NMR (270 MHz, δppm, CDCl$_3$) 0.04 (s, 12H) 0.83 (s, 9H) 0.87 (s, 9H) 1.00 (t, J=7.4 Hz, 3H) 1.6–2.0 (m, 4H) 2.3–2.5 (m, 1H) 2.43 (t, J=7.3 Hz, 2H) 2.5–3.0 (m, 2H) 3.11 (br.d, J=6.6 Hz, 1H) 3.5–3.7 (m, 2H) 3.74 (s, 3H) 4.0–4.2 (m, 1H) 4.06 (s, 2H) 4.27 (dt, J=5.9 & 5.9 Hz, 1H) 5.47 (dd, J=8.4 & 16.3 Hz, 1H) 5.65 (dd, J=5.6 & 15.5 Hz, 1H) 7.1–7.3 (m, 5H)

Example 54

Synthesis of methyl(11R,12S,13E,15S)-9-butyryloxy-11,15-dihydroxy-16-phenyl-17,18,19,20-tetranor-3-oxa-7-thiaprosta-8,13-dienoate (R$^1$=Pr, R$^2$=H, R$^3$=H, R$^4$=Benzyl, W=OH, X—Y=O—CH$_2$, Z=CO$_3$Me, n=0, ≡=trans-CH=CH)

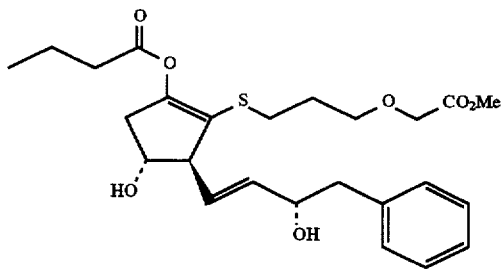

Using as the material and reagent a hydrogen fluoride-pyridine solution (0.25 ml) and methyl(11R,12S,13E,15S)-9-butyryloxy-11,15-bis(tert-butyldimethylsiloxy)-16-phenyl-17,18,19,20-tetranor-3-oxa-7-thiaprosta-8,13-dienoate (238 mg), the same procedure as in Example 2 was performed to obtain methyl(11R,12S,13E,15S)-9-butyryloxy-11,15-dihydroxy-16-phenyl-17,18,19,20-tetranor-3-oxa-7-thiaprosta-8,13-dienoate (122 mg, 76%).

$^1$H-NMR (270 MHz, δppm, CDCl$_3$) 1.01 (t, J=7.4 Hz, 3H) 1.5–1.9 (m, 4H) 2.3–2.5 (m, 1H) 2.44 (t, J=7.3 Hz, 2H) 2.6–3.0 (m, 5H) 3.26 (br.d, J=8.3 Hz, 1H) 3.58 (dt, J=1.4 & 5.9 Hz, 2H) 3.74 (s, 3H) 4.0–4.2 (m, 1H) 4.06 (s, 2H) 4.37 (dt, J=6.3 & 6.6 Hz, 1H) 5.57 (dd, J=8.1 & 15.3 Hz, 1H) 5.72 (dd, J=5.9 & 15.5 Hz, 1H) 7.2–7.4 (m, 5H)

Example 55

Synthesis of methyl(2E,11R,12S,13E,15S,17R)-9-butyryloxy-11,15-bis(tert-butyldimethylsiloxy)-17,20-dimethyl-7-thiaprosta-2,8,13-trienoate (R$^1$=Pr, R$^2$=$^t$BuMe$_2$Si, R$_3$=H, R$^4$=2-Me-hexyl, W=$^t$BuMe$_2$SiO, X—Y=trans-CH=CH, Z=CO$_2$Me, n=0, ≡=trans-CH=CH)

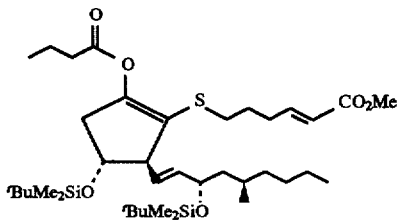

Using as the materials and reagents (1E,3S,5R)-1-iodo-3-(tert-butyldimethylsiloxy)-5-methyl-1-nonene (476 mg, 1.2 mmol), tert-butyllithium (1.54 mol/l, 1.56 ml, 2.4 mmol), 1-hexynylcopper (174 mg), hexamethylphosphorous triamide (436 μl), (4R)-4-(tert-butyldimethylsiloxy)-2-(5-methoxycarbonyl-4-trans-pentenylthio)-2-cyclopenten-1-one (371 mg, 1.0 mmol), and butyric anhydride (442 μl), the same procedure was performed as in Example 1 to obtain methyl(2E,11R,12S,13E,15S,17R)-9-butyryloxy-11,15-bis(tert-butyldimethylsiloxy)-17,20-dimethyl-7-thiaprosta-2,8,13-trienoic acid (232 mg, 33%).

$^1$H-NMR (270 MHz, δppm, CDCl$_3$) 0.03 (s), 0.05 . . . . . . 12H 0.8–1.0 (m, 6H) 0.87 (s, 9H) 0.89 (s, 9H) 1.00 (t, J=7.4 Hz, 3H) 1.0–1.8 (m, 13H) 2.2–2.6 (m, 4H) 2.42 (t, J=7.4 Hz, 2H) 2.6–2.8 (m, 1H) 2.92 (ddd, J=1.3 & 6.6 & 16.5 Hz, 1H) 3.10 (d, J=8.6 Hz, 1H) 3.72 (s, 3H) 4.1–4.2 (m, 2H) 5.42 (dd, J=8.6 & 15.5 Hz, 1H) 5.61 (dd, J=5.9 & 15.5 Hz, 1H) 5.83 (d, J=15.5 Hz, 1H) 6.92 (dt, J=15.5 & 6.9 Hz

Example 56

Synthesis of methyl(2E,11R,12S,13E,15S,17R)-9-butyryloxy-11,15-dihydroxy-17,20-dimethyl-7-thiaprosta-2,8,13-trienoate (R$^1$=Pr, R$^2$=H, R$^3$=H, R$^4$=2-Me-hexyl, W=OH, X—Y=trans-CH=CH), Z=CO$_2$Me, n=0, ≡=trans-CH=CH)

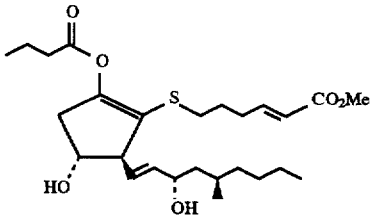

Using as the material and reagent a hydrogen fluoride-pyridine solution (0.2 ml) and methyl(2E,11R,12S,13E,15S,17R)-9-butyryloxy-11,15-bis(tert-butyldimethylsiloxy)-17,20-dimethyl-7-thiaprosta-2,8,13-trienoate (232 mg), the same procedure as in Example 2 was performed to obtain methyl(2E,11R,12S,13E,15S,17R)-9-butyryloxy-11,15-dihydroxy-17,20-dimethyl-7-thiaprosta-2,8,13-trienoate (145 mg, 92%).

$^1$H-NMR (270 MHz, δppm, CDCl$_3$) 0.8–1.0 (m, 6H) 1.01 (t, J=7.4 Hz, 3H) 1.1–1.4 (m, 6H) 1.4–1.8 (m, 7H) 2.2–2.8 (m, 5H) 2.44 (t, J=7.4 Hz, 2H) 2.96 (dd, J=6.3 & 17.2 Hz, 1H) 3.20 (d, J=5.9 Hz, 1H) 3.71 (s, 3H) 4.1–4.3 (m, 2H) 5.57 (dd, J=8.1 & 15.3 Hz, 1H) 5.70 (dd, J=5.9 & 15.5 Hz, 1H) 5.85 (d, J=15.5 Hz, 1H) 6.92 (dt, J=15.8 & 7.1 Hz, 1H)

Example 57

Synthesis of methyl(11R,12S,13E)-9-butyryloxy-11-tert-butyldimethylsiloxy-15-hydroxy-16-(3-chlorophenyl)-17,18,19,20-tetranor-7-thiaprosta-8,13-dienoate (R$^1$=Pr, R$^2$=$^t$BuMe$_2$Si, R$^3$=H, R$^4$=3-Chlorobenzyl, W=$^t$BuMe$_2$SiO, X—Y=CH$_2$—CH$_2$, Z=CO$_2$Me, n=0, ≡=trans-CH=CH)

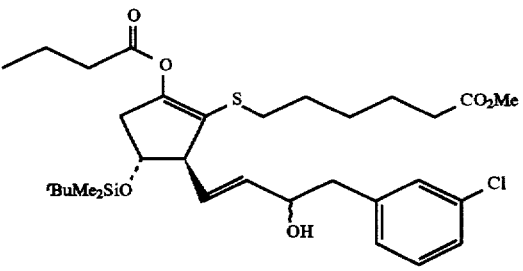

Using as materials and reagents chromium(II) chloride (100 mg), nickel chloride (0.1 mg), (3S,4R)-4-(tert-butyldimethylsiloxy)-1-butyryloxy-2-(5-methoxycarbonylpentylthio)-3-(trans-2-iodovinyl)-1-cyclopentene (76 mg), and 3-chlorophenylacetoaldehyde (50 mg), the same procedure was performed as in Example 39 to obtain methyl(11R,12S,13E)-9-butyryloxy-11-tertbutyldimethylsiloxyl-15-hydroxy-16-(3-chlorophenyl)-17,18,19,20-tetranor-7-thiaprosta-8,13-dienoate (14 mg, 14%).

Note that the thus obtained methyl(11R,12S,13E)-9-butyryloxy-11-tert-butyldimethylsiloxy-15-hydroxy-16-(3-chlorophenyl)-17,18,19,20-tetranor-7-thiaprosta-8,13-dienoate is a diastereomer mixture of mixed stereo isomers of different hydroxyl groups at the 15-position.

$^1$H-NMR (270 MHz, δppm, CDCl$_3$) 0.03 (s), 0.03 (s) ...... 6H 0.87 (s, 9H) 1.01 (t, J=7.4 Hz, 3H) 1.2–1.8 (m, 8H) 2.30 (t, J=7.4 Hz, 2H) 2.3–2.8 (m, 3H) 2.43 (t, J=7.4 Hz, 2H) 2.8–3.0 (m, 3H) 3.0–3.2 (m, 1H) 3.66 (s, 3H) 4.0–4.1 (m, 1H) 4.3–4.4 (m, 1H) 5.56 (dd, J=8.4 & 15.3 Hz, 1H) 5.6–5.8 (m, 1H) 7.0–7.4 (m, 4H)

Example 58

Synthesis of methyl(11R,12S,13E)-9-butyryloxy-11,15-dihydroxy-16-(3-chlorophenyl)-17,18,19,20-tetranor-7-thiaprosta-8,13-dienoate (R$^1$=Pr, R$^2$=H, R$^3$=H, R$^4$=3-Chlorobenzyl, W=OH, X—Y=CH$_2$—CH$_2$, Z=CO$_2$Me, n=0, ═=trans-CH═CH)

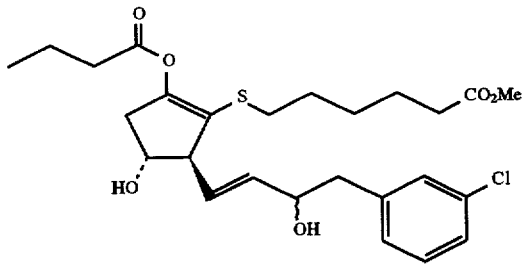

Using as the material and reagent a hydrogen fluoride-pyridine solution (0.1 ml) and methyl(11R,12S,13E)-9-butyryloxy-11-tert-butyldimethylsiloxyl-15-hydroxy-16-(3-chlorophenyl)-17,18,19,20-tetranor-7-thiaprosta-8,13-dienoate (14 mg), the same procedure as in Example 2 was performed to separately obtain two stereoisomers of methyl (11R,12S,13E)-9-butyryloxy-11,15-dihydroxy-16-(3-chlorophenyl)-17,18,19,20-tetranor-7-thiaprosta-8,13-dienoate different at the 15-position. (Low polarity compound: 4 mg, 35%; high polarity compound: 4 mg, 35%)

[Low polarity compound]

$^1$H-NMR (270 MHz, δppm, CDCl$_3$) 1.01 (t, J=7.4 Hz, 3H) 1.2–1.8 (m, 8H) 2.31 (t, J=7.3 Hz, 2H) 2.3–2.8 (m, 3H) 2.43 (t, J=7.3 Hz, 2H) 2.8–3.0 (m, 3H) 3.20 (d, J=6.6 Hz, 1H) 3.66 s, 3H) 4.0–4.1 (m, 1H) 4.36 (dt, J=6.3 & 6.3 Hz, 1H) 5.51 (dd, J=8.3 & 15.5 Hz, 1H) 5.74 (dd, J=6.6 & 15.8 Hz, 1H) 7.0–7.3 (m, 4H)

[High polarity compound]

$^1$H-NMR (270 MHz, δppm, CDCl$_3$) 1.01 (t, J=7.4 Hz, 3H) 1.2–1.8 (m, 8H) 2.31 (t, J=7.4 Hz, 2H) 2.4–2.7 (m, 3H) 2.44 (t, J=7.4 Hz, 2H) 2.83 (d, J=6.9 Hz, 2H) 2.93 (ddd, J=1.3 & 6.3 & 16.5 Hz, 1H) 3.20 (d, J=7.9 Hz, 1H) 3.66 (s, 3H) 4.0–4.1 (m, 1H) 4.37 (dt, J=6.3 & 5.9 Hz, 1H) 5.56 (dd, J=7.9 & 15.2 Hz, 1H) 5.74 (dd, J=6.3 & 15.5 Hz, 1H) 7.0–7.2 (m, 1H) 7.2–7.3 (m, 3H)

Example 59

Synthesis of methyl(11R,12S,13E)-9-butyryloxy-11-tert-butyldimethylsiloxy-15-hydroxy-16-(4-chlorophenyl)-17,18,19,20-tetranor-7-thiaprosta-8,13-dienoate (R$^1$=Pr, R$^2$=$^t$BuMe$_2$Si, R$^3$=H, R$^4$=4-Chlorobenzyl, W=$^t$BuMe$_2$SiO, X—Y=CH$_2$—CH$_2$, Z=CO$_2$Me, n=0, ═=trans-CH═CH)

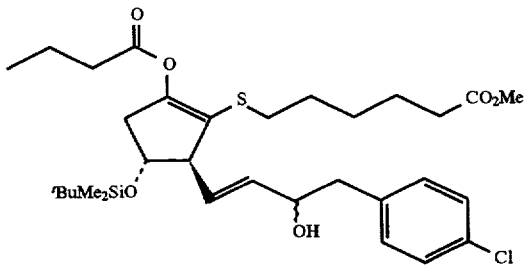

Using as the materials and reagents chromium(II) chloride (307 mg), nickel chloride (0.1 mg), (3S,4R)-4-(tert-butyldimethylsiloxy)-1-butyryloxy-2-(5-methoxycarbonylpentylthio)-3-(trans-2-iodovinyl)-1-cyclopentene (235 mg), and 4-chlorophenylacetoaldehyde (155 mg), the same procedure was performed as in Example to obtain methyl(11R,12S,13E)-9-butyryloxy-11-tert-butyldimethylsiloxy-15-hydroxy-16-(4-chlorophenyl)-17,18,19,20-tetranor-7-thiaprosta-8,13-dienoate (191 mg, 61%).

Note that the methyl(11R,12S,13E)-9-butyryloxy-11-tert-butyldimethylsiloxy-15-hydroxy-16-(4-chlorophenyl)-17,18,19,20-tetranor-7-thiaprosta-8,13-dienoate thus obtained is a diastereomer mixture of mixed stere isomers of different hydroxyl groups at the 15-position.

$^1$H-NMR (270 Hz, δppm, CDCl$_3$) 0.03 (s), 0.03 (s) ...... 6H 0.87 (s, 9H) 1.01 (t, J=7.4 Hz, 3H) 1.2–1.8 (m, 8H) 2.30 (t, J=7.4 Hz, 2H) 2.3–2.7 (m, 3H) 2.43 (t, J=7.3 Hz, 2H) 2.7–3.0 (m, 3H) 3.12 (br.d, J=8.3 Hz, 1H) 3.66 (s, 3H) 4.0–4.1 (m, 1H) 4.3–4.4 (m, 1H) 5.55 (dd, J=8.3 & 15.5 Hz, 1H) 5.6–5.8 (m, 1H) 7.1–7.3 (m, 4H)

Example 60

Synthesis of methyl(11R,12S,13E)-9-butyryloxy-11,15-dihydroxy-16-(4-chlorophenyl)-17,18,19,20-tetranor-7-thiaprosta-8,13-dienoate (R$^1$=Pr, R$^2$=H, R$^3$=H, R$^4$=4-Chlorobenzyl, W=OH, X—Y=CH$_2$—CH$_2$, Z=CO$_2$Me, n=0, ═=trans-CH═CH)

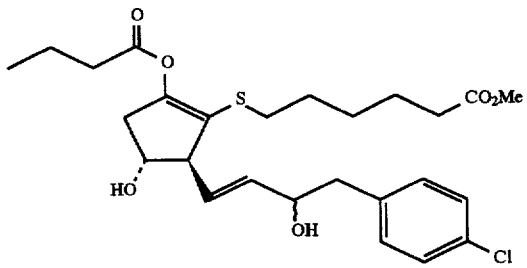

Using as the material and reagent a hydrogen fluoride-pyridine solution (0.2 ml) and methyl(11R,12S,13E)-9-butyryloxy-11-tert-butyldimethylsiloxyl-15-hydroxy-16-(4-chlorophenyl)-17,18,19,20-tetranor-7-thiaprosta-8,13- dienoate (191 mg), the same procedure as in Example 2 was performed to separately obtain two stereoisomers of methyl (11R,12S,13E)-9-butyryloxy-11,15-dihydroxy-16-(4-chlorophenyl)-17,18,19,20-tetranor-7-thiaprosta-8,13-dienoate different at the 15-position. (Low polarity compound: 64 mg, 41%; high polarity compound: 52 mg, 33%)

[Low polarity compound]

$^1$H-NMR (270 MHz, δppm, CDCl$_3$) 1.01 (t, J=7.4 Hz, 3H) 1.2–1.8 (m, 8H) 2.31 (t, J=7.3 Hz, 2H) 2.4–2.8 (m, 3H) 2.44 (t, J=7.4 Hz, 2H) 2.82 (d, J=6.6 Hz, 2H) 2.92 (dd, J=5.3 & 16.5 Hz, 1H) 3.19 (d, J=7.6 Hz, 1H) 3.66 (s, 3H) 4.0–4.1 (m, 1H) 4.34 (dt, J=6.2 & 6.6 Hz, 1H) 5.53 (dd, J=8.1 & 15.7 Hz, 1H) 5.74 (dd, J=5.9 & 15.5 Hz, 1H) 7.15 (d, J=8.3 Hz, 2H) 7.26 (d, J=8.3 Hz, 2H)

[High polarity compound]

$^1$H-NMR (270 MHz, δppm, CDCl$_3$) 1.01 (t, J=7.4 Hz, 3H) 1.2–1.8 (m, 8H) 2.31 (t, J=7.3 Hz, 2H) 2.4–2.7 (m, 3H) 2.44 (t, J=7.4 Hz, 2H) 2.8–2.9 (m, 2H) 2.92 (dd, J=6.3 & 16.8 Hz, 1H) 3.20 (br.d, J=7.9 Hz, 1H) 3.66 (s, 3H) 4.0–4.2 (m, 1H) 4.34 (dt, J=6.3 & 6.6 Hz, 1H) 5.56 (dd, J=7.9 & 15.5 Hz, 1H) 5.73 (dd, J=5.8 & 15.7 Hz, 1H) 7.16 (d, J=8.3 Hz, 2H) 7.26 (d, J=8.3 Hz, 2H)

Example 61

Synthesis of methyl(11R,12S,13E)-9-butyryloxy-11-tert-butyldimethylsiloxy-15-hydroxy-16-(4-nitrophenyl)-17,18,19,20-tetranor-7-thiaprosta-8,13-dienoate (R$^1$=Pr, R$^2$=$^t$BuMe$_2$Si, R$^3$=H, R$^4$=4-Nitrobenzyl, W=$^t$BuMe$_2$SiO, X—Y=CH$_2$—CH$_2$, Z=CO$_2$Me, n=0, ═=trans-CH═CH)

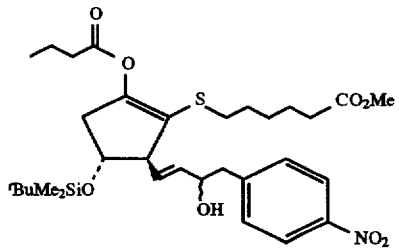

Using as the materials and reagents chromium(II) chloride (135 mg), nickel chloride (0.1 mg), (3S,4R)-4-(tert-butyldimethylsiloxy)-1-butyryloxy-2-(5-methoxycarbonylpentylthio)-3-(trans-2-iodovinyl)-1-cyclopentene (103 mg), and 4-nitrophenylacetoaldehyde (73 mg), the same procedure was performed as in Example 39 to obtain methyl(11R,12S,13E)-9-butyryloxy-11-tert-butyldimethylsiloxy-15-hydroxy-16-(4-nitrophenyl)-17,18,19,20-tetranor-7-thiaprosta-8,13-dienoate (17 mg, 12%).

Note that the thus obtained methyl(11R,12S,13E)-9-butyryloxy-11-tert-butyldimethylsiloxy-15-hydroxy-16-(4-nitrophenyl)-17,18,19,20-tetranor-7-thiaprosta-8,13-dienoate is a diastereomer mixture of mixed stereo isomers of different hydroxyl groups at the 15-position.

$^1$H-NMR (270 MHz, δppm, CDCl$_3$) 0.02 (s), 0.03 (s) .. .... 6H 0.87 (s, 9H) 1.01 (t, J=6.3 Hz, 3H) 1.2–1.8 (m, 8H) 2.30 (t, J=7.3 Hz, 2H) 2.3–2.7 (m, 3H) 2.43 (t, J=6.9 Hz, 2H) 2.8–3.2 (m, 4H) 3.66 (s, 3H) 4.0–4.2 (m, 1H) 4.3–4.5 (m, 1H) 5.3–5.8 (m, 2H) 7.40 (d, J=8.9 Hz, 2H) 8.1–8.3 (m, 2H)

Example 62

Synthesis of methyl(11R,12S,13E)-9-butyryloxy-11,15-dihydroxy-16-(4-nitrophenyl)-17,18,19,20-tetranor-7-thiaprosta-8,13-dienoate (R$^1$=Pr, R$^2$=H, R$^3$=H, R$^4$=4-Nitrobenzyl, W=OH, X—Y=CH$_2$—CH$_2$, Z=CO$_2$Me, n=0, ═=trans-CH═CH)

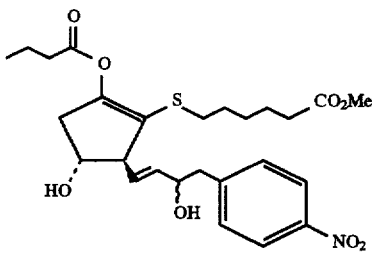

Using as the material and reagent a hydrogen fluoride-pyridine solution (0.1 ml) and methyl(11R,12S,13E)-9-butyryloxy-11-tert-butyldimethylsiloxyl-15-hydroxy-16-(4-nitrophenyl)-17,18,19,20-tetranor-7-thiaprosta-8,13-dienoate (17 mg), the same procedure as in Example 2 was performed to separately obtain two stereoisomers of methyl (11R,12S,13E)-9-butyryloxy-1,15-dihydroxy-16-(4-nitrophenyl)-17,18,19,20-tetranor-7-thiaprosta-8,13-dienoate different at the 15-position. (Low polarity compound: 6 mg, 44%; high polarity compound: 5 mg, 38%)

[Low polarity compound]

$^1$H-NMR (270 MHz, δppm, CDCl$_3$) 1.01 (t, J=7.4 Hz, 3H) 1.2–1.8 (m, 8H) 2.31 (t, J=7.3 Hz, 2H) 2.4–2.8 (m, 3H) 2.44 (t, J=7.4 Hz, 2H) 2.8–3.0 (m, 1H) 2.96 (dr J=6.3 Hz, 2H) 3.20 (br.d, J=6.9 Hz, 1H) 3.66 (s, 3H) 4.0–4.1 (m, 1H) 4.41 (dt, J=6.2 & 6.6 Hz, 1H) 5.56 (dd, J=7.9 & 16.2 Hz, 1H) 5.76 (dd, J=6.4 & 15.4 Hz, 1H) 7.40 (d, J=8.9 Hz, 2H) 8.15 (d, J=8.6 Hz, 2H)

[High polarity compound]

$^1$H-NMR (270 MHz, δppm, CDCl$_3$) 1.01 (t, J=7.4 Hz, 3H) 1.2–1.8 (m, 8H) 2.31 (t, J=7.4 Hz, 2H) 2.4–2.8 (m, 3H) 2.44 (t, J=7.4 Hz, 2H) 2.8–3.0 (m, 1H) 2.96 (d, J=6.6 Hz, 2H) 3.20 (br.d, J=7.3 Hz, 1H) 3.66 (s, 3H) 4.0–4.2 (m, 1H) 4.42 (dt, J=6.3 & 6.6 Hz, 1H) 5.58 (dd, J=7.9 & 15.1 Hz, 1H) 5.75 (dd, J=6.3 & 15.5 Hz, 1H) 7.40 (d, J=8.6 Hz, 2H) 8.15 (d, J=8.6 Hz, 2H)

Example 63

Synthesis of methyl(11R,12S,13E)-9-butyryloxy-11-tert-butyldimethylsiloxy-15-hydroxy-15-phenyl-16,17,18,19,20-pentanor-7-thiaprosta-8,13-dienoate (R$^1$=Pr, R$^2$=H, R$^3$=H, R$^4$=Ph, W=$^t$BuMe$_2$SiO, X—Y=CH$_2$—CH$_2$, Z=CO$_2$Me, n=0, ═=trans-CH═CH)

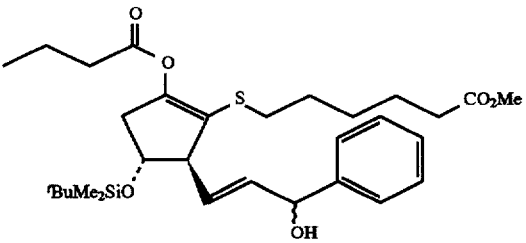

Using as the materials and reagents (3S,4R)-4-(tert-butyldimethylsiloxy)-1-butyryloxy-2-(5- methoxycarbonylpentylthio)-3-(trans-2-iodovinyl)-1-cyclopentene (323 mg), chromium(II) chloride (325 mg), nickel chloride (0.1 mg), and benzaldehyde (115 mg), the same procedure was performed as in Example 39 to obtain methyl(11R,12S,13E)-9-butyryloxy-11-tert-butyldimethylsiloxy-15-hydroxy-15-phenyl-16,17,18,19,20-pentanor-7-thiaprosta-8,13-dienoate (188 mg, 60%).

Note that the thus obtained methyl(11R,12S,13E)-9-butyryloxy-11-tert-butyldimethylsiloxy-15-hydroxy-15-phenyl-16,17,18,19,20-pentanor-7-thiaprosta-8,13-dienoate is a diastereomer mixture of mixed stereo isomers of different hydroxyl groups at the 15-position.

$^1$H-NMR (270 MHz, δppm, $CDCl_3$) −0.07 (s, 3/2H) −0.03 (s, 3/2H) 0.02 (s, 3/2H) 0.03 (s, 3/2H) 0.81 (s, 9/2H) 0.86 (s, 9/2H) 1.00 (t, J=6.6 Hz, 3H) 1.2–1.8 (m, 8H) 1.9–2.08 (m, 1/2H) 2.2–2.7 (m, 7H) 2.8–2.92 (m, 1H) 3.15–3.25 (m, 1H) 3.66 (s, 3H) 4.1–4.24 (m, 1H) 5.17–5.28 (m, 1H) 5.62–5.74 (m, 1H) 5.82–5.95 (m, 1H) 7.25–7.45 (m, 5H)

Example 64

Synthesis of methyl(11R,12S,13E)-9-butyryloxy-11,15-dihydroxy-15-phenyl-16,17,18,19,20-pentanor-7-thiaprosta-8,13-dienoate ($R^1$=Pr, $R^2$=H, $R^3$=H, $R^4$= Ph, W=OH, X—Y=$CH_2$—$CH_2$, Z=$CO_2$Me, n=0, ⇌=trans-CH═CH)

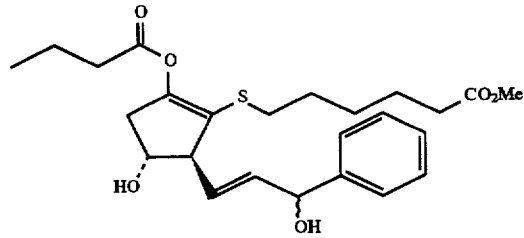

Using as the material and reagent a hydrogen fluoride-pyridine solution (0.4 ml) and methyl(11R,12S,13E)-9-butyryloxy-11-tert-butyldimethylsiloxyl-15-hydroxy-15-phenyl-16,17,18,19,20pentanor-7-thiaprosta-8,13-dienoate (185 mg), the same procedure as in Example 2 was performed to obtain methyl(11R,12S,13E)-9-butyryloxy-11,15dihydroxy-15phenyl-16,17,18,19,20-pentanor-7-thiaprosta-8,13-dienoate (129 mg, 90%).

Note that the thus obtained methyl(11R, 12S,13E)-9-butyrloxy-11,15-dihydroxy-15-phenyl-16,17,18,19,20-pentanor-7-thiaprosta-8,13-dienoate is a diastereomer mixture of mixed stereo isomers of different hydroxyl groups at the 15-position.

$^1$H-NMR (270 MHz, δppm, $CDCl_3$) 1.00 (t, J=7.3 Hz, 3H) 1.2–1.8 (m, 8H) 2.1–2.75 (m, 7H) 2.9–3.03 (m, 1H) 3.22–3.29 (m, 1H) 3.66 (s, 3H) 4.15–4.24 (br, 1H) 5.19–5.27 (m, 1H) 5.65–5.78 (m, 1H) 5.85–5.98 (m, 1H) 7.25–7.42 (m, 5H)

Example 65

Synthesis of methyl(11R,12S,13E)-9-butyryloxy-11-tert-butyldimethylsiloxy-15-hydroxy-18-phenyl-19,20-dinor-7-thiaprosta-8,13-dienoate ($R^1$=Pr, $R^2$=H, $R^3$H, $R^4$=Phenylpropyl, W=$^tBuMe_2SiO$, X—Y=$CH_2$—$CH_2$, Z=$CO_2$ME, n=0, ⇌=trans-CH═CH)

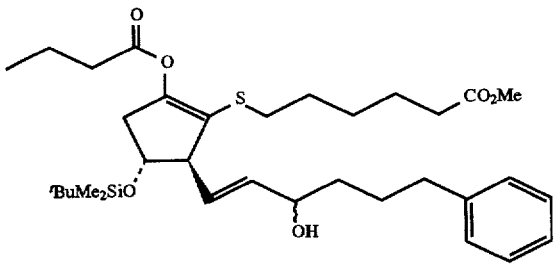

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (433 mg), chromium(II) chloride (440 mg), nickel chloride (0.1 mg), and 4-phenyl-butyraldehyde (220 mg), the same procedure was performed as in Example 39 to obtain methyl(11R,12S,13E)-9-butyryloxy-11-tert-butyldimethylsiloxy-15-hydroxy-18-phenyl-19,20-dinor-7-thiaprosta-8,13-dienoate (325 mg, 72%).

Note that the methyl(11R,12S,13E)-9-butyryloxy-11-tert-butyldimethylsiloxy-15-hydroxy-18-phenyl-19,20-dinor-7-thiaprosta-8,13-dienoate thus obtained is a diastereomer mixture of mixed stereo isomers of different hydroxyl groups at the 15-position.

$^1$H-NMR (270 MHz, δppm, $CDCl_3$) −0.02 (s, 3H) 0.01 (s, 3H) 0.83 (s), 0.84 (s) . . . . . 9H) 0.97 (t, J=7.5 Hz, 3H) 1.25–1.8 (m, 10H) 2.25 (dt, J=7.5 & 1.6 Hz, 2H) 2.39 (t, J=7.4 Hz, 2H) 2.4–2.65 (m, 5H) 2.83 (ddd, J=16.2 & 6.9 & 1.3 Hz, 1H) 3.11 (dd, J=8.2 & 3.6 Hz, 1H) 3.63 (s, 3H) 4.0–4.18 (m, 2H) 5.50 (ddd, J=15.9 & 8.6 & 3.0 Hz, 1H) 5.64 (dd, J=15.9 & 5.9 Hz, 1H) 7.08–7.3 (m, 5H)

Example 66

Synthesis of methyl(11R,12S,13E)-9-butyryloxy-11,15-dihydroxy-18-phenyl-19,20-dinor-7-thiaprosta-8,13-dienoate ($R^1$=Pr, $R^2$=H, $R^3$=H, $R^4$= Phenylpropyl, W=OH, X—Y=$CH_2$—$CH_2$, Z=$CO_2$Me, n=0, ⇌=trans-CH═CH)

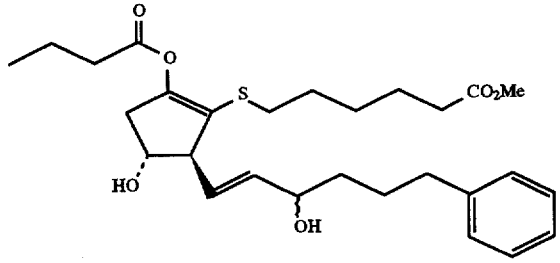

Using as the material and reagent a hydrogen fluoride-pyridine solution (0.5 ml) and methyl(11R,12S,13E)-9-butyryloxy-11-tert-butyldimethylsiloxyl-15-hydroxy-18-phenyl-19,20-dinor-7-thiaprosta-8,13-dienoate (305 mg), the same procedure as in Example 2 was performed to separately obtain two stereoisomers of methyl(11R,12S, 13E)-9-butyryloxy-11,15-dihydroxy-18-phenyl-19,20-dinor-7-thiaprosta-8,13-dienoate different at the 15-position. (Low polarity compound: 94 mg, 38%; high polarity compound: 91 mg, 37%)

[Low polarity compound]

$^1$H-NMR (270 MHz, δppm, CDCl$_3$) 1.01 (t, J=7.5 Hz, 3H) 1.3–1.8 (m, 10H) 2.30 (t, J=7.3 Hz, 2H) 2.43 (t, J=7.3 Hz, 2H) 2.45–2.7 (m, 5H) 2.95 (ddd, J=16.5 & 6.6 & 1.3 Hz, 1H) 3.20 (d-like, J=5.3 Hz, 1H) 3.66 (s, 3H) 4.1–4.2 (m, 2H) 5.54 (dd, J=15.5 & 7.9 Hz, 1H) 5.70 (dd, J=15.5 & 6.3 Hz, 1H) 7.14–7.3 (m, 5H)

[High polarity compound]

$^1$H-NMR (270 MHz, δppm, CDCl$_3$) 1.01 (t, J=7.5 Hz, 3H) 1.3–1.8 (m, 10H) 2.29 (t, J=7.3 Hz, 2H) 2.43 (t, J=7.3 Hz, 2H) 2.40–2.7 (m, 5H) 2.94 (ddd, J=16.5 & 6.6 & 1.3 Hz, 1H) 3.20 (dd, J=6.6 & 2.6 Hz, 1H) 3.66 (s, 3H) 4.1–4.2 (m, 2H) 5.55 (dd, J=15.8 & 7.9 Hz, 1H) 5.68 (dd, J=15.8 & 6.3 Hz, 1H) 7.1–7.3 (m, 5H)

Example 67

Synthesis of methyl(11R,12S,13E)-9-butyryloxy-11-tert-butyldimethylsiloxy-15-hydroxy-16-(4-methylphenyl)-17,18,19,20-tetranor-7-thiaprosta-8,13-dienoate (R$^1$=Pr, R$^2$=H, R$^3$=H, R$^4$=4-Me-Benzyl, W=$^t$BuMe$_2$SiO, X—Y=CH$_2$—CH$_2$, Z=CO$_2$Me, n=0, ⚌=trans-CH═CH)

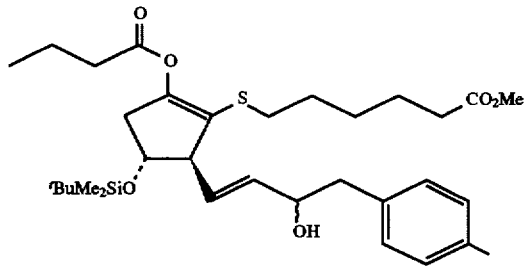

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (433 mg), chromium(II) chloride (440 mg), nickel chloride (0.1 mg), and (4-methylphenyl) acetoaldehyde (195 mg), the same procedure was performed as in Example 39 to obtain methyl(11R,12S,13E)-9-butyryloxy-11-tert-butyldimethylsiloxy—hydroxy-16-(4-methylphenyl)-17,18,19,20-tetranor-7-thiaprosta-8,13-dienoate (320 mg, 72%).

Note that the thus obtained methyl(11R,12S,13E)-9-butyryloxy-11-tert-butyldimethylsiloxy-15-hydroxy-16-(4-methylphenyl)-17,18,19,20-tetranor-7-thiaprosta-8,13-dienoate is a diastereomer mixture of mixed stereo isomers of different hydroxyl groups at the 15-position.

$^1$H-NMR (270 MHz, δppm, CDCl$_3$) 0.03 (s, 6H) 0.87 (s, 9H) 1.00 (t, J=7.4 Hz, 3H) 1.2–1.8 (m, 8H) 2.29 (t, J=7.6 Hz, 2H) 2.31 (s, 3H) 2.42 (t, J=7.3 Hz, 2H) 2.3–2.9 (m, 6H) 3.15 (br-d, J=8 Hz, 1H) 3.65 (s, 3H) 4.05 (m, 1H) 4.35 (m, 1H) 5.45–5.8 (m, 2H) 7.11 (s, 4H)

Example 68

Synthesis of methyl(11R,12S,13E)-9-butyryloxy-11,15-dihydroxy-16-(4-methylphenyl)-17,18,19,20-tetranor-7-thiaprosta-8,13-dienoate (R$^1$=Pr, R$^2$=H, R$^3$=H, R$^4$=4-Me-Benzyl, W=OH, X—Y=CH$_2$—CH$_2$, Z=CO$_2$Me, n=0, ⚌=trans-CH═CH)

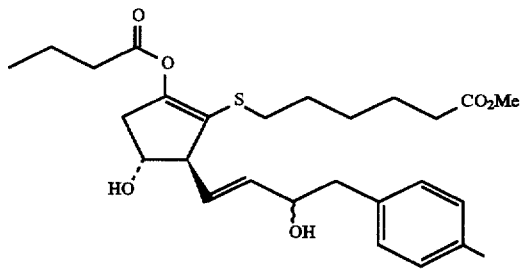

Using as the material and reagent a hydrogen fluoride-pyridine solution (0.5 ml) and methyl(11R,12S,13E)-9-butyryloxy-11-tert-butyldimethylsiloxyl-15-hydroxy-16-(4-methylphenyl)-17,18,19,20-tetranor-7-thiaprosta-8,13-dienoate (300 mg), the same procedure as in Example 2 was performed to separately obtain two stereo isomers of methyl (11R,12S,13E)-9-butyryloxy-11,15-dihydroxy-16-(4-methylphenyl)-17,18,19,20-tetranor-7-thiaprosta-8,13-dienoate different at the 15-position.

(Low polarity compound: 73 mg, 30%; high polarity compound: 83 mg, 34%)

[Low polarity compound]

$^1$H-NMR (270 MHz, δppm, CDCl$_3$) 1.01 (t, J=7.3 Hz, 3H) 1.2–1.8 (m, 8H) 1.87 (br, 1H) 2.16 (br, 1H) 2.30 (t, J=7.3 Hz, 2H) 2.32 (s, 3H) 2.43 (t, J=7.3 Hz, 2H) 2.35–2.70 (m, 3H) 2.80 (d, J=6.6 Hz, 2H) 2.90 (dd, J=16.5 & 6.3 Hz, 1H) 3.18 (br-d, J=7.9 Hz, 1H) 3.66 (s, 3H) 4.03 (m, 1H) 4.35 (m, 1H) 5.50 (ddd, J=15.5 & 8.2 & 1.0 Hz, 1H) 5.72 (dd, J=15.5 & 5.9 Hz, 1H) 7.10 (s, 4H)

[High polarity compound]

$^1$H-NMR (270 MHz, δppm, CDCl$_3$) 1.01 (t, J=7.3 Hz, 3H) 1.2–1.9 (m, 9H) 2.30 (t, J=7.5 Hz, 2H) 2.32 (s, 3H) 2.44 (t, J=7.3 Hz, 2H) 2.35–3.0 (m, 5H) 3.20 (br-d, J=8 Hz, 1H) 3.66 (s, 3H) 4.10 (m, 1H) 4.34 (m, 1H) 5.57 (dd, J=15.5 & 8.2 Hz, 1H) 5.75 (dd, J=15.5 & 5.9 Hz, 1H) 7.10 (s, 4H)

Example 69

Synthesis of methyl(11R,12S,13E)-9-butyryloxy-11-tert-butyldimethylsiloxy-15-hydroxy-16-(3-thienyl)-17,18,19,20-tetranor-7-thiaprosta-8,13-dienoate (R$^1$=Pr, R$^2$=H, R$^3$=H, R$^4$=3-Thienyl, W=$^t$BuMe$_2$SiO, X—Y=CH$_2$—CH$_2$, Z=CO$_2$Me, n=0, ⚌=trans-CH═CH)

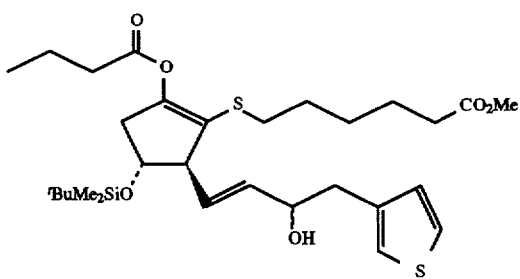

Using as the materials and reagents (3S,4R)-4-(tert-butyldimethylsiloxy)-1-butyryloxy-2-(5- methoxycarbonylpentylthio)-3-(trans-2-iodovinyl)-1-cyclopentene (418 mg), chromium(II) chloride (4.20 g), nickel chloride (0.1 mg), and 3-thienylacetoaldehyde (176 mg), the same procedure was performed as in Example 39 to obtain methyl(11R,12S,13E)-9-butyryloxy-11-tert-butyldimethylsiloxy-15-hydroxy-16-(3-thienyl)-17,18,19,20-tetranor-7-thiaprosta-8,13-dienoate (267 mg.

Note that the methyl(11R,12S,13E)-9-butyryloxy-11-tert-butyldimethylsiloxy-15-hydroxy-16-(3-thienyl)-17,18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.03 (s, 6H) 0.87 (s, 9H) 1.00 (t, J=7.4 Hz, 3H) 1.2–1.8 (m, 8H) 2.29 (t, J=7.6 Hz, 2H) 2.42 (t, J=7.4 Hz, 2H) 2.4–2.65 (m, 3H) 2.75–2.9 (m, 3H) 3.10 (br-d, J=8 Hz, 1H) 3.66 (s, 3H) 4.0–4.15 (m, 1H) 4.3–4.4 (m, 1H) 5.5–5.75 (m, 2H) 7.00 (dd, J=4.9 & 1.0 Hz, 1H) 7.06 (d, J=2.0 Hz, 1H) 7.22 (m, 1H)

Example 70

Synthesis of methyl(11R,12S,13E)-9-butyryloxy-11,15-dihydroxy-16-(3-thienyl)-17,18,19,20-tetranor-7-thiaprosta-8,13-dienoate (R$^1$=Pr, R$^2$=H, R$^3$=H, R$^4$=4-Me-Benzyl, W=OH, X—Y=CH$_2$—CH$_2$, Z=CO$_2$Me, n=0, =trans-CH=CH)

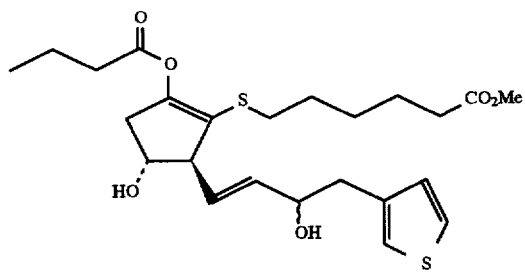

Using as the material and reagent a hydrogen fluoride-pyridine solution (0.5 ml) and methyl(11R,12Sr13E)-9-butyryloxy-11-tert-butyldimethylsiloxyl-15-hydroxy-16-(3-thienyl)-17,18,19,20-tetranor-7-thiaprosta-8,13-dienoate (260 mg), the same procedure as in Example 2 was performed to separately obtain two stereo isomers of methyl (11R,12S,13E)-9-butyryloxy-11,15-dihydroxy-16-(3-thienyl)-17,18,19,20-tetranor-7-thiaprosta-8,13-dienoate different at the 15-position. (Low polarity compound: 47 mg, 22%; high polarity compound: 64 mg, 30%)

[Low polarity compound]

$^1$H-NMR (270 MHz, δppm, CDCl$_3$) 1.01 (t, J=7.4 Hz, 3H) 1.2–1.8 (m, 8H) 1.99 (d, J=3.9 Hz, 1H) 2.10 (d, J=5.9 Hz, 1H) 2.31 (t, J=7.4 Hz, 2H) 2.43 (t, J=7.3 Hz, 2H) 2.4–2.7 (m, 3H) 2.86–2.96 (m, 1H) 2.89 (d, J=6.6 Hz, 1H) 3.20 (br-d, J=8.2 Hz, 1H ) 3.66 (s, 3H) 4.0–4.1 (m, 1H) 4.3–4.45 (m, 1H) 5.54 (dd, J=15.5 & 8.3 Hz, 1H) 5.75 (dd, J=15.5 & 6.3 Hz, 1H) 6.98 (dd, J=4.7 & 1.2 Hz, 1H) 7.05–7.06 (m, 1H) 7.25–7.29 (m, 1H)

[High polarity compound]

$^1$H-NMR (270 MHz, δppm, CDCl$_3$) 1.01 (t, J=7.4 Hz, 3H) 1.2–1.8 (m, 8H) 1.95 (br, 1H) 2.31 (t, J=7.3 Hz, 2H) 2.44 (t, J=7.3 Hz, 2H) 2.3–2.75 (m, 4H) 2.8–3.0 (m, 3H) 3.19 (dd, J=7.9 & 2.6 Hz, 1H) 3.66 (s, 3H) 4.05–4.15 (m, 1H) 4.3–4.42 (m, 1H) 5.59 (dd, J=15.5 & 8.3 Hz, 1H) 5.74 (dd, J=15.5 & 6.2 Hz, 1H) 6.99 (dd, J=5.0 & 1.0 Hz, 1H) 7.06 (d, J=2.0 Hz, 1H) 7.26–7.28 (m, 1H)

Example 71

Synthesis of methyl(11R,12S,13E)-9-butyryloxy-11-tert-butyldimethylsiloxy-15-hydroxy-16-(3-methylphenyl)-17,18,19,20-tetranor-7-thiaprosta-8,13-dienoate (R$^1$=Pr, R$^2$=H, R$^3$=H, R$^4$=3-Me-Benzyl, W=$^t$BuMe$_2$SiO, X—Y=CH$_2$—CH$_2$, Z=CO$_2$Me, n=0, =trans-CH=CH)

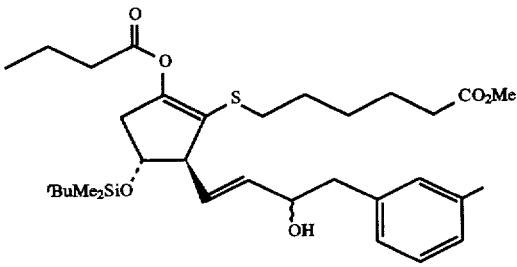

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (418 mg), chromium(II) chloride (440 mg), nickel chloride (0.1 mg), and (3-methylphenyl) acetoaldehyde (188 mg), the same procedure was performed as in Example 39 to obtain methyl(11R,12S,13E)-9-butyryloxy-11-tert-butyldimethylsiloxy-15-hydroxy-16-(3-methylphenyl)-17,18,19,20-tetranor-7-thiaprosta-8,13-dienoate (234 mg, 55%)

Note that the methyl(11R,12S,13E)-9-butyryloxy-11-tert-butyldimethylsiloxy-15-hydroxy-16-(3-methylphenyl)-17,18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.03 (s, 6H) 0.87 (s, 9H) 1.00 (t, J=7.4 Hz, 3H) 1.3–1.8 (m, 8H) 2.29 (t, J=7.6 Hz, 2H) 2.33 (s, 3H) 2.42 (t, J=7.3 Hz, 2H) 2.4–2.9 (m, 6H) 3.15 (br-d, J=10 Hz, 1H) 3.65 (s, 3H) 4.05 (m, 1H) 4.35 (m, 1H) 5.5–5.65 (m, 1H) 5.68–5.80 (m, 1H) 6.95–7.05 (m, 3H) 7.19 (t, J=7.6 Hz, 1H)

Example 72

Synthesis of methyl(11R,12Sr13E)-9-butyryloxy-11,15-dihydroxy-16-(3-methylphenyl)-17,18,19,20-tetranor-7-thiaprosta-8,13-dienoate (R$^1$=Pr, R$^2$=H, R$^3$=H, R$^4$=3-Me-Benzyl, W=OH, X—Y=CH$_2$—CH$_2$, Z=CO$_2$Me, n=0, =trans-CH=CH)

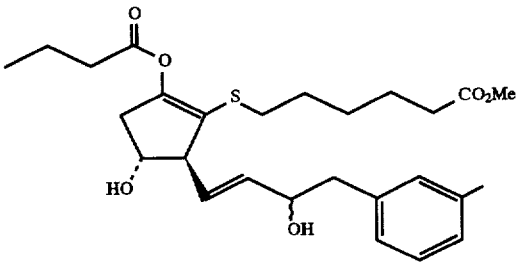

Using as the material and reagent a hydrogen fluoride-pyridine solution (0.5 ml) and methyl(11R,12S,13E)-9-butyryloxy-11-tert-butyldimethylsiloxyl-15-hydroxy-16-(3-methylphenyl)-17,18,19,20-tetranor-7-thiaprosta-8,13- dienoate (225 mg) the same procedure as in Example 2 was performed to separately obtain two stereo isomers of methyl (11R,12S,13E)-9-butyryloxy-11,15-dihydroxy-16-(3-methylphenyl)-17,18,19,20-tetranor-7-thiaprosta-8,13-dienoate different at the 15-position. (Low polarity compound: 65 mg, 36%; high polarity compound: 73 mg, 40%)

[Low polarity compound]

$^1$H-NMR (270 MHz, δppm, CDCl$_3$) 1.01 (t, J=7.5 Hz, 3H) 1.3–1.8 (m, 8H) 1.87 (br, 1H) 2.06 (br, 1H) 2.30 (t, J=7.3 Hz, 2H) 2.33 (s, 3H) 2.43 (t, J=7.3 Hz, 2H) 2.35–2.73 (m, 3H) 2.81 (d, J=6.9 Hz, 2H) 2.90 (ddd, J=16.5 & 6.6 & 1.2 Hz, 1H) 3.19 (dd, J=8.3 & 2.0 Hz, 1H) 3.66 (s, 3H) 3.95–4.05 (br, 1H) 4.3–4.43 (m, 1H) 5.52 (ddd, J=16.5 & 8.2 & 1.0 Hz, 1H) 5.75 (dd, J=16.5 & 6.2 Hz, 1H) 6.95–7.08 (m, 3H) 7.19 (t, J=7.5 Hz, 1H)

[High polarity compound]

$^1$H-NMR (270 MHz, δppm, CDCl$_3$) 1.01 (t, J=7.4 Hz, 3H) 1.3–1.8 (m, 8H) 1.9 (br, 1H) 2.30 (t, J=7.4 Hz, 2H) 2.33 (s, 3H) 2.44 (t, J=7.4 Hz, 2H) 2.35–2.95 (m, 5H) 3.19 (dd, J=8.1 & 2.5 Hz, 1H) 3.66 (s, 3H) 4.02–4.12 (br, 1H) 4.3–4.44 (m, 1H) 5.57 (ddd, J=16.2 & 8.3 & 1.0 Hz, 1H) 5.75 (dd, J=16.2 & 6.0 Hz, 1H) 6.95–7.07 (m, 3H) 7.19 (t, J=7.5 Hz, 1H)

Example 73

Synthesis of methyl(11R,12S,13E)-9-butyryloxy-11-tert-butyldimethylsiloxy-15-hydroxy-16-(2-methylphenyl)-17,18,19,20-tetranor-7-thiaprosta-8, 13-dienoate (R$^2$=Pr, R$^2$=H, R$^3$=H, R$^4$=2-Me-Benzyl, W=$^t$BuMe$_2$SiO, X—Y=CH$_2$—CH$_2$, Z=CO$_2$Me, n=0, ═=trans-CH═CH)

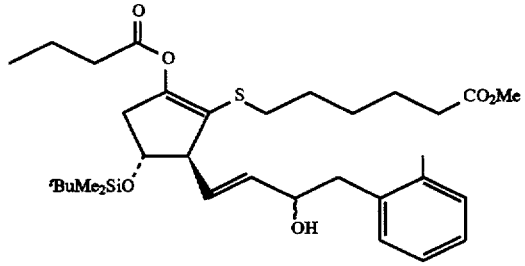

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (418 mg), chlromium(II) chloride (427 mg), nickel chloride (0.1 mg), and (2-methylphenyl) acetoaldehyde (188 mg), the same procedure was performed as in Example 39 to obtain methyl(11R,12S,13E)-9-butyryloxy-11-tert-butyldimethylsiloxy-15-hydroxy-16-(2-methylphenyl)-17,18,19,20-tetranor-7-thiaprosta-8,13-dienoate (330 mg, 96%).

Note that the methyl(11R,12S,13E)-9-butyryloxy-11-tert-butyldimethylsiloxy-15-hydroxy-16-(2-methylphenyl)-17, 18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.04 (s, 6H) 0.88 (s, 9H) 1.01 (t, J=7.4 Hz, 3H) 13–1.8 (m, 8H) 2.30 (t, J=7.6 Hz, 2H) 2.34 (s, 3H) 2.43 (t, J=7.3 Hz, 2H) 2.3–2.9 (m, 6H) 3.14 (br-d, J=8 Hz, 1H) 3.66 (s, 3H) 4.0–4.1 (m, 1H) 4.25–4.4 (m, 1H) 5.45–5.6 (m, 1H) 5.67–5.80 (m, 1H) 7.0–7.2 (m, 4H)

Example 74

Synthesis of methyl(11R,12S,13E)-9-butyryloxy-11, 15-dihydroxy-16-(2-methylphenyl)-17,18,19,20-tetranor-7-thiaprosta-8,13-dienoate (R$^1$=Pr, R$^2$=H, R$^3$=H, R$^4$=2-Me-Benzyl, W=OH, X—Y=CH$_2$—CH$_2$, Z=CO$_2$Me, n=0, ═=trans-CH═CH)

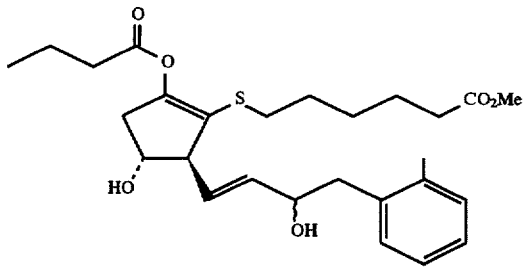

Using as the material and reagent a hydrogen fluoride-pyridine solution (0.6 ml) and methyl(11R,12S,13E)-9-butyryloxy-11-tert-butyldimethylsiloxyl-15-hydroxy-16-(2-methylphenyl)-17,18,19,20-tetranor-7-thiaprosta-8,13-dienoate (330 mg), the same procedure as in Example 2 was performed to separately obtained two stereo isomers of methyl(11R,12S,13E)-9-butyryloxy-11,15-dihydroxy-16-(2-methylphenyl)-17,18,19,20-tetranor-7-thiaprosta-8,13-dienoate different at the 15-position. (Low polarity compound: 69 mg, 21%; high polarity compound: 80 mg, 24%)

[Low polarity compound]

$^1$H-NMR (270 MHz, δppm, CDCl$_3$) 1.01 (t, J=7.5 Hz, 3H) 1.3–1.8 (m, 8H) 1.90 (br-d, J=3.7 Hz, 1H) 2 07 (br, 1H) 2.31 (s, 3H) 2.43 (t, J=7.3 Hz, 2H) 2.4–2.7 (m, 3H) 2.78–2.97 (m, 3H) 3.17 (dd, J=8.2 & 2.0 Hz, 1H) 3.66 (s, 3H) 3.9–4.0 (br, 1H) 4.3–4.42 (m, 1H) 5.47 (ddd, J=16.5 & 8.2 & 1.0 Hz, 1H) 5.76 (dd, J=16.5 & 6.7 Hz, 1H) 7.10–7.19 (m, 4H)

[High polarity compound]

$^1$H-NMR (270 MHz, δppm, CDCl$_3$) 1.01 (t, J=7.4 Hz, 3H) 1.3–1.8 (m, 8H) 1.95 (br, 1H) 2.30 (t, J=7.6 Hz, 2H) 2.34 (s, 3H) 2.44 (t, J=7.4 Hz, 2H) 2.4–2.7 (m, 3H) 2.85 (d, J=6.5 Hz, 2H) 2.8–2.95 (m, 2H) 3.19 (dd, J=8.1 & 2.4 Hz, 1H) 3.66 (s, 3H) 4.08 (br, 1H) 4.36 (q-like, J=6.6 Hz, 1H) 5.58 (dd, J=15.5 & 8.0 Hz, 1H) 5.77 (dd, J=15.5 & 6.3 Hz, 1H) 7.10–7.19 (m, 4H)

Example 75

Synthesis of (3S,4R)-4-(tert-butyldimethylsiloxy)-1-butyryloxy-2-(5-methoxycarbonylhexyl)-3-(trans-2-tributylstanylvinyl)-1-cyclopentene

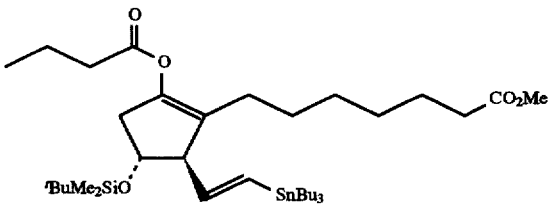

Using as the materials and reagents trans-1,2-bis (tributylstanyl)ethylene (1.92 g), methyllithium (1.25 mol/l, 4.93 ml), 250 mg of copper(I) cyanide, (4R)-tert-butyldimethylsiloxy-2-(5-methoxycarbonylhexyl)-2-cyclopenten-1-one (709 mg), and acetic anhydride (1.15 ml), the same procedure was performed as in Example 35 to obtain (3S,4R)-4-(tert-butyldimethylsiloxy)-1-butyryloxy-2-(5-methoxycarbonylhexyl)-3-(trans-2-tributylstanylvinyl)-1-cyclopentene (1.26 g).

¹H-NMR (270 MHz, δppm, CDCl₃) 0.05 (s, 6H) 0.84 (s, 18H) 0.87 (t-like, J=7 Hz, 3H) 1.2–2.5 (m, 34H) 2.8–2.9 (m, 1H) 3.0–3.1 (m, 1H) 3.69 (s, 3H) 4.1–4.2 (m, 1H) 5.75 (dd, J=18.8 & 8.6 Hz, 1H) 6.09 (d, J=18.8 Hz, 1H)

Example 76

Synthesis of (3S,4R)-4-(tert-butyldimethylsiloxy)-1-butyryloxy-2-(5-methoxycarbonylhexyl)-3-(trans-2-iodovinyl)-1-cyclopentene

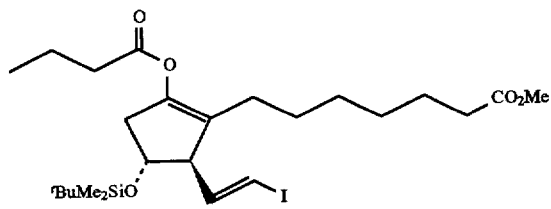

Using as the materials and reagents (3S,4R)-4-(tert-butyldimethylsiloxy)-1-butyryloxy-2-(5-methoxycarbonylhexyl)-3-(trans-2-tributylstanylvinyl)-1-cyclopentene (1.10 g) and iodine (384 mg), the same procedure was performed as in Example 36 to obtain (3S,4R)-4-(tert-butyldimethylsiloxy)-1-butyryloxy-2-(5-methoxycarbonylhexyl)-3-(trans-2-iodovinyl)-1-cyclopentene (274 mg).

¹H-NMR (270 MHz, δppm, CDCl₃) 0.04 (s, 6H) 0.87 (s, 9H) 1.00 (t, J=7.3 Hz, 3H) 1.15–1.8 (m, 10H) 1.9–2.1 (m, 1H) 2.30 (t, J=7.4 Hz, 2H) 2.38 (t, J=7.4 Hz, 2H) 2.35–2.5 (m, 1H) 2.76 (dd, J=15.5 & 6.6 Hz, 1H) 3.04 (dd, J=9.4 & 4.4 Hz, 1H) 3.67 (s, 3H) 1.4–4.2 (m, 1H) 6.18 (d, J=14.2 Hz, 1H) 6.36 (dd, J=14.2 & 9.4 Hz, 1H)

Example 77

Synthesis of methyl(11Rt12S,13E)-9-butyryloxy-11-tert-butyldimethylsiloxy-15-hydroxy-16-phenyl-17,18,19,20-tetranor-prosta-8,13-dienoate

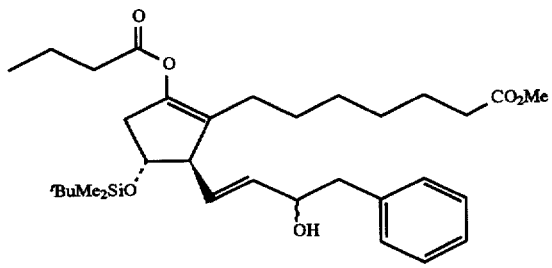

Using as the materials and reagents (3S,4R)-4-(tert-butyldimethylsiloxy)-1-butyryloxy-2-(5-methoxycarbonylhexyl)-3-(trans-2-iodovinyl)-1-cyclopentene (193 mg), chromium(II) chloride (203 mg), nickel chloride (0.1 mg), and phenylacetoaldehyde (80 mg), the same procedure was performed as in Example 39 to obtain methyl(11R,12S,13E)-9-butyryloxy-11-tert-butyldimethylsiloxy-15-hydroxy-16-phenyl-17,18,19,20-tetranor-prosta-8,13-dienoic acid (135 mg, 71%).

Note that the thus obtained methyl(11R,12S,13E)-9-butyryloxy-11-tert-butyldimethylsiloxy-15-hydroxy-16-phenyl-17,18,19,20-tetranor-prosta-8,13-dienoate is a diastereomer mixture of mixed stereo isomers of different hydroxyl different at the 15-position.

¹H-NMR (270 MHz, δppm, CDCl₃) 0.02 (s, 6H) 0.87 (s, 9H) 0.98 (t, J=7.2 Hz, 3H) 1.1–1.8 (m, 10H) 1.9–2.05 (m, 1H) 2.28 (t, J=7.4 Hz, 2H) 2.37 (t, J=7.3 Hz, 2H) 2.35–2.45 (m, 1H) 2.7–2.9 (m, 3H) 2.95–3.05 (m, 1H) 3.65 (s, 3H) 4.0–4.1 (m, 1H) 4.3–4.4 (m, 1H) 5.4–5.75 (m, 2H) 7.15–7.4 (m, 5H)

Example 78

Synthesis of methyl(11R,12S,13E)-9-butyryloxy-11,15-dihydroxy-16-phenyl-17,18,19,20-tetranor-prosta-8,13-dienoate

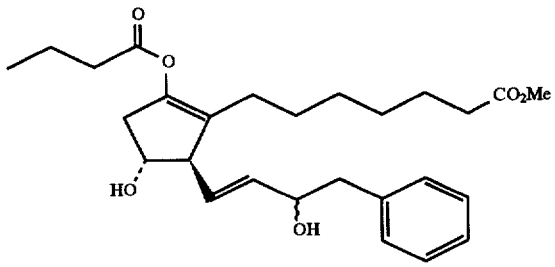

Using as the materials and reagents a hydrogen fluoride-pyridine solution (0.25 ml) and methyl(11R,12S,13E)-9-butyryloxy-11-tert-butyldimethylsiloxyl-15-hydroxy-16-phenyl-17,18,19,20-tetranor-prosta-8,13-dienoate (130 mg), the same procedure as in Example 2 was performed to separately obtain two stereo isomers of methyl(11R,12S,13E)-9-butyryloxy-11,15-dihydroxy-16-phenyl-17,18,19,20-tetranor-prosta-8,13-dienoate different at the 15-position. (Low polarity compound:43 mg, 41%; high polarity compound:41 mg, 39%)

[Low polarity compound]

¹H-NMR (270 MHz, δppm, CDCl₃) 0.99 (t, J=7.4 Hz, 3H) 1.15–1.4 (m, 4H) 1.5–1.88 (m, 8H) 1.90–2.10 (m, 1H) 2.29 (t, J=7.4 Hz, 2H) 2.39 (t, J=7.3 Hz, 2H) 2.35–2.45 (m, 1H) 2.75–2.9 (m, 1H) 2.85 (d, J=7.3 Hz, 2H) 2.03 (dd, J=8.7 & 3.1 Hz, 1H) 3.66 (s, 3H) 3 95 (br, 1H) 4.3–4.4 (m, 1H) 5.41 (dd, J=15.5 Hz, 8.9 Hz, 1H) 5.67 (dd, J=15.5 & 6.3 Hz, 1H) 7.15–7.38 (m, 5H)

[High polarity compound]

¹H-NMR (270 MHz, δppm, CDCl₃) 0.99 (t, J=7.4 Hz, 3H) 1.15–1.4 (m, 5H) 1.5–1.78 (m, 5H) 1.82 (br, 1H) 1.9–2.05 (m, 2H) 2.13 (br, 1H) 2.29 (t, J=7.6 Hz, 2H) 2.39 (t, J=7.3 Hz, 2H) 2.35–2.45(m, 1H) 2.75–2.9 (m, 1H) 2.83 (d, J=6.6 Hz, 2H) 2.03 (dd, J=8.9 & 2.7 Hz, 1H) 3.66 (s, 3H) 4.02 (br, 1H) 4.3–4.4 (m, 1H) 5.45 (dd, J=15.5 & 8.9 Hz, 1H) 5.65 (dd, J=15.5 & 6.4 Hz, 1H) 7.18–7.35 (m, 5H)

Example 79

Synthesis of methyl(11R,12S,13E)-9-butyryloxy-11-tert-butyldimethylsiloxy-15-hydroxy-16-phenoxy-17,18,19,20-tetranor-7-thiaprosta-8,13-dienoate (R$^1$=Pr, R$^2$=H, R$^3$=H, R$^4$=Phenoxymethyl, W=$^t$BuMe$_2$SiO, X—Y=CH$_2$—CH$_2$, Z=CO$_2$Me, n=0, $\rightleftharpoons$=trans-CH=CH)

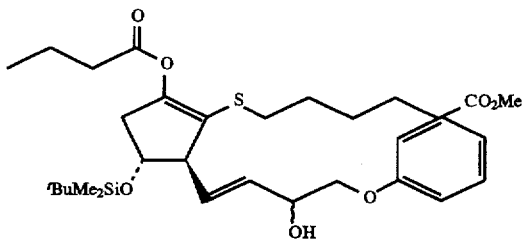

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (298 mg), chromium(II) chloride (307 mg), nickel chloride (0.3 mg), and phenoxyacetoaldehyde (136 mg), the same procedure was performed as in Example 39 to obtain methyl(11R,12S,13E)-9-butyryloxy-11-tert-butyldimethylsiloxyl-15-hydroxy-16-phenoxy-17,18,19,20-tetranor-7-thiaprosta-8,13-dienoate (183 mg, 60%).

Note that the methyl(11R,12S,13E)-9-butyryloxy-11-tert-butyldimethylsiloxyl-15-hydroxy-16-phenoxy-17,18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.04 (s, 3H) 0.05 (s, 1.5H) 0.06 (s, 1.5H) 0.88 (s, 4.5H) 0.89 (s, 4.5H) 1.00 (t, J=7.4 Hz, 3H) 1.2–1.8 (m, 8H) 2.9 (t, J=6.5 Hz, 2H) 2.43 (t, J=7.3 Hz, 2H) 2.4–2.7 (m, 1H) 2.80–2.95 (m, 1H) 3.2 (br, 1H) 3.66 (s, 3H) 3.89 (dd, J=9.4 & 7.5 Hz, 1H) 4.01 (dd, J=9.4 & 3.4 Hz, 1H) 4.15–4.25 (m, 1H) 4.5–4.6 (m, 1H) 5.79 (d-like, J=4.5 Hz, 2H) 6.85–7.00 (m, 3H) 7.25–7.33 (m, 2H)

Example 80

Synthesis of methyl(11R,12S,13E)-9-butyryloxy-11,15-dihydroxy-16-phenoxy-17,18,19,20-tetranor-7-thiaprosta-8,13-dienoate (R$^1$=Pr, R$^2$=H, R$^3$=H R$^4$=Phenoxymethyl, W=OH, X—Y=CH$_2$—CH$_2$, Z=CO$_2$Me, n=0, $\rightleftharpoons$=trans-CH=CH)

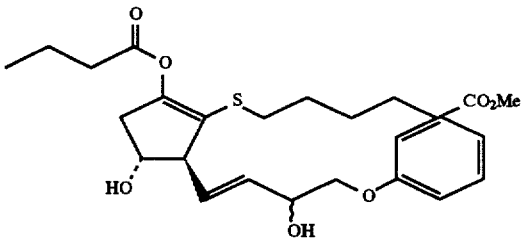

Using as the materials and reagents a hydrogen fluoride-pyridine solution (0.4 ml) and methyl(11R,12S,13E)-9-butyryloxy-11-tert-butyldimethylsiloxyl-15-hydroxy-16-phenoxy-17,18,19,20-tetranor-7-thiaprosta-8,13-dienoate (172 mg), the same procedure was followed as in Example 2 to separately obtain two stereo isomers of methyl(11R, 12S,13E)-9-butyryloxy-11,15-dihydroxy-16-phenoxy-17,18,19,20-tetranor-7-thiaprosta-8,13-dienoic acid different at the 15-position. (Low polarity compound: 49 mg, 37%; high polarity compound: 56 mg, 40%)

[Low polarity compound]

$^1$H-NMR (270 MHz, δppm, CDCl$_3$) 1.01 (t, J=7.4 Hz, 3H) 1.2–1.8 (m, 8H) 2.29 (t, J=7.4 Hz, 2H) 2.44 (t, J=7.3 Hz, 2H) 2.5–2.75 (m, 3H) 2.97 (ddd, J=16.5 & 6.6 & 1.3 Hz, 1H) 3.26 (m, 1H) 3.66 (s, 3H) 3.89 (dd, J=9.6 & 7.3 Hz, 1H) 4.01 (dd, J=9.6 & 3.6 Hz, 1H) 4.13–4.23 (m, 1H) 5.81 (d-like, J=4.0 Hz, 2H) 6.88–7.00 (m, 3H) 7.22–7.35 (m, 2H)

[High polarity compound]

$^1$H-NMR (270 MHz, δppm, CDCl$_3$) 1.00 (t, J=7.6 Hz, 3H) 1.3–1.8 (m, 8H) 2.28 (t, J=7.3 Hz, 2H) 2.43 (t, J=7.3 Hz, 2H) 2.45–2.72 (m, 3H) 2.7 (br-s, 1H) 2.94 (ddd, J=16.5 & 6.9 & 1.3 Hz, 1H) 3.25 (m, 1H) 3.66 (s, 3H) 3.90 (dd, J=9.6 & 7.2 Hz, 1H) 4.00 (dd, J=9.6 & 3.6 Hz, 1H) 4.15–4.25 (m, 1H) 4.5–4.6 (m, 1H) 5.78–5.81 (m, 2H) 6.88–7.00 (m, 3H) 7.22–7.35 (m, 2H)

Example 81

Synthesis of methyl(11R,12S,13E)-9-butyryloxy-11-tert-butyldimethylsiloxy-15-hydroxy-19-phenyl-20-nor-7-thiaprosta-8,13-dienoate (R$^1$=Pr, R$^2$=H, R$^3$=H, R$^4$=4-Phenylbutyl, W=$^t$BuMe$_2$SiO, X—Y=CH$_2$—CH$_2$, Z=CO$_2$Me, n=0, $\rightleftharpoons$=trans-CH=CH)

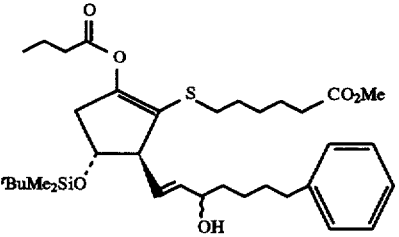

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (298 mg), chromium(II) chloride (307 mg), nickel chloride (0.3 mg), and 5-phenylvaleraldehyde (162 mg), the same procedure was performed as in Example 39 to obtain methyl(11R,12S,13E)-9-butyryloxy-11-tert-butyldimethylsiloxy-15-hydroxy-19-phenyl-20-nor-7-thiaprosta-8,13-dienoate (263 mg, 83%).

Note that the methyl(11R,12S,13E)-9-butyryloxy-11-tert-butyldimethylsiloxy-15-hydroxy-19-phenyl-20-nor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.03 (s, 3H) 0.04 (s, 3H) 0.87 (s, 9H) 1.00 (t, J=7.3 Hz, 3H) 1.2–1.8 (m, 14H) 2.29 (t, J=7.3 Hz, 2H) 2.42 (t, J=7.5 Hz, 2H) 2.4–2.65 (m, 5H) 2.86 (dd, J=16.0 & 7.1 Hz, 1H) 3.1–3.15 (m, 1H) 3.66 (s, 3H) 4.02–4.15 (m, 2H) 5.52 (ddd, J=15.5 & 8.6 & 2.6 Hz, 1H) 5.67 (dd, J=15.5 & 6.1 Hz, 1H) 7.1–7.3 (m, 5H) 7.25–7.33 (m, 2H)

Example 82

Synthesis of methyl(11R,12S,13E)-9-butyryloxy-11,15-dihydroxy-19-phenyl-20-nor-7-thiaprosta-8,13-dienoate ($R^1$=Pr, $R^2$=H, $R^3$=H, $R^4$=4-phenylbutyl, W=OH, X—Y=$CH_2$—$CH_2$, Z=$CO_2$Me, n=0, ═=trans-CH═CH)

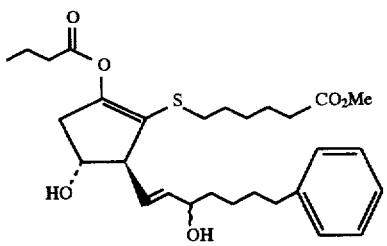

Using as the materials and reagents a hydrogen fluoride-pyridine solution (0.5 ml) and methyl(11R,12S,13E)-9-butyryloxy-11-tert-butyldimethlsiloxyl-15-hydroxy-19-phenyl-20-nor-7-thiaprosta-8,13-dienoate (243 mg), the same procedure as in example 2 was perfomed to separately obtain two stereo isomers of methyl(11R,12S,13E)-9-butyryloxy-11,15-dihydrox-19-phenyl-20-nor-7-thiaprosta-8,13-dienoate different at the 15-position. (Low polarity compound: 70 mg, 36%; high polarity compound: 73 mg, 37%)

[Low polarity compound]

$^1$H-NMR (270 MHz, δppm, CDCl$_3$) 1.01 (t, J=7.3 Hz, 3H) 1.2–1.85 (m, 14H) 2.30 (t, J=7.4 Hz, 2H) 2.43 (t, J=7.3 Hz, 2H) 2.45–2.75 (m, 5H) 2.94 (ddd, J=16.0 & 6.2 & 1.3 Hz, 1H) 3.21 (d-like, J=7.5 Hz, 1H) 3.66 (s, 3H) 4.1–4.2 (m, 2H) 5.54 (dd, J=15.5 & 7.8 Hz, 1H) 5.70 (dd, J=15.5 & 6.6 Hz, 1H) 7.1–7.35 (m, 5H)

[High polarity compound]

$^1$H-NMR (270 MHz, δppm, CDCl$_3$) 1.01 (t, J=7.4 Hz, 3H) 1.2–1.8 (m, 14H) 1.85 (br, 1H 2.30 (t, J=7.2 Hz, 2H) 2.43 (t, J=7.4 Hz, 2H) 2.4–2.7 (m, 5H) 2.92 (ddd, J=16.5 & 6.6 & 1.3 Hz, 1H) 3.20 (d-like, J=7.5 Hz, 1H) 3.66 (s, 3H) 4.1–4.2 (m, 2H) 5.55 (dd, J=15.5 & 7.9 Hz, 1H) 5.68 (dd, J=15.5 & 6.4 Hz, 1H) 7.1–7.35 (m, 5H)

Example 83

Synthesis of methyl(11R,12S,13E)-9-butyryloxy-11-tert-butyldimethylsiloxy-15-hydroxy-17-methyl-19,20-dinor-7-thiaprosta-8,13-dienoate ($R^1$=Pr, $R^2$=H, $R^3$=H, $R^4$=$^i$Pr, W=$^t$BuMe$_2$SiO, X—Y=$CH_2$—$CH_2$, Z=$CO_2$Me, n=0, ═=trans-CH═CH)

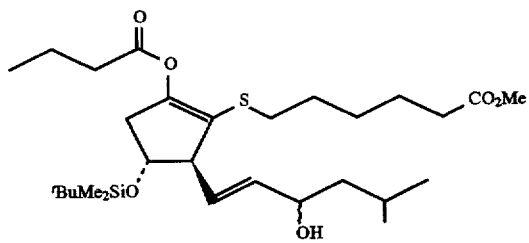

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (239 mg), chromium(II) chloride (246 mg), nickel chloride (0.3 mg), and isovaleraldehyde (69 mg), the same procedure was performed as in Example 39 to obtain methyl(11R,12S,13E)-9-butyryloxy-11-tert-butyldimethylsiloxy-15-hydroxy-17-methyl-19,20-dinor-7-thiaprosta-8,13-dienoate (127 mg, 57%).

Note that the methyl(11R,12S,13E)-9-butyryloxy-11-tert-butyldimethylsiloxy-15-hydroxy-17-methyl-19,20-dinor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.04 (s, 6H) 0.88 (s, 9H) 0.7–1.0 (m, 9H) 11–1.8 (m, 11H) 2.30 (t, J=7.3 Hz, 2H) 2.42 (t, J=7.2 Hz, 2H) 2.3–2.7 (m, 3H) 2.84 (dd, J=16.0 & 7.1 Hz, 1H) 3.05–3.15 (m, 1H) 3.65 (s, 3H) 4.0–4.2 (m, 2H) 5.57 (ddd, J=16.0 & 8.6 & 2.6 Hz, 1H) 5.67 (dd, J=16.0 & 6.5 Hz, 1H)

Example 84

Synthesis of methyl(11R,12S,13E)-9-butyryloxy-11,15-dihydroxy-17-methyl-19,20-dinor-7-thiaprosta-8,13-dienoate ($R^1$=Pr, $R^2$=H, $R^3$=H, $R^4$=$^i$Pr, W=OH, X—Y=$CH_2$—$CH_2$, Z=$CO_2$Me, n=0, ═=trans-CH═CH)

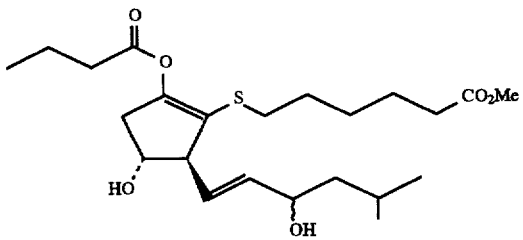

Using as the material and reagent a hydrogen fluoride-pyridine solution (0.4 ml) and methyl(11R,12S,13E)-9-butyryloxy-11-tert-butyldimethylsiloxyl-15-hydroxy-17-methyl-19,20-dinor-7-thiaprosta-8,13-dienoate (123 mg), the same procedure as in Example 2 was performed to separately obtain two stereo isomers of methyl(11R,12S,13E)-9-butyryloxy-11,15-dihydroxy-17-methyl-19,20-dinor-7-thiaprosta-8,13-dienoate different at the 15-position. (Low polarity compound: 34 mg, 35%; high polarity compound: 37 mg, 38%)

[Low polarity compound]

$^1$H-NMR (270 MHz, δppm, CDCl$_3$) 0.92 (dd, J=6.6 & 2.3 Hz, 6H) 1.01 (t, J=7.4 Hz, 3H) 1.2–1.8 (m, 11H) 2.31 (t, J=7.4 Hz, 2H) 2.44 (t, J=7.2 Hz, 2H) 2.5–2.75 (m, 3H) 2.97 (ddd, J=16.5 & 6.5 & 1.3 Hz, 1H) 3.21 (d-like, J=7 Hz, 1H) 3.67 (s, 3H) 4.1–4.25 (m, 2H) 5.58 (dd, J=15.6 & 7.9 Hz, 1H) 5.72 (dd, J=15.6 & 6.1 Hz, 1H

[High polarity compound]

$^1$H-NMR (270 MHz, δppm, CDCl$_3$) 0.92 (dd, J=6.6 & 2.3 Hz, 6H) 1.01 (t, J=7.3 Hz, 3H) 1.2–1.8 (m, 11H) 2.31 (t, J=7.4 Hz, 2H) 2.43 (t, J=7.2 Hz, 2H) 2.5–2.75 (m, 3H) 2.94 (ddd, J=16.6 & 6.9 & 1.3 Hz, 1H) 3.21 d-like, J=7 Hz, 1H) 3.67 (s, 3H) 4.1–4.25 (m, 2H) 5.57 (dd, J=15.6 & 7.7 Hz, 1H 5.68 (dd, J=15.6 & 6.3 Hz, 1H

Example 85

Synthesis of methyl(11R,12S,13E)-9-butyryloxy-11-tert-butyldimethylsiloxy-15-hydroxy-16-cyclohexyl-17,18,19,20-tetranor-7-thiaprosta-8,13-dienoate ($R^1$=Pr, $R^2$=H, $R^3$=H, $R^4$=cyclohexylmethyl, W= $^t$BuMe$_2$SiO, X—Y=CH$_2$—CH$_2$, Z=CO$_2$Me, n=0, ═══trans-CH═CH)

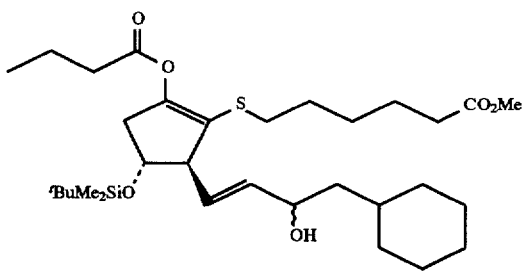

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (200 mg), chromium(II) chloride (246 mg), nickel chloride (0.3 mg), and cyclohexylacetoaldehyde (126 mg), the same procedure was performed as in Example 39 to obtain methyl(11R,12S,13E)-9-butyryloxy-11-tert-butyldimethylsiloxy-15-hydroxy-16-cyclohexyl-17,18,19,20-tetranor-7-thiaprosta-8,13-dienoate (145 mg, 71%).

Note that the methyl(11R,12S,13E)-9-butyryloxy-11-tert-butyldimethylsiloxy-15-hydroxy-16-cyclohexyl-17,18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.04 (s, 6H) 0.87 (s, 9H) 0.8–1.0 (m, 2H) 1.00 (t, J=7.4 Hz, 3H) 1.1–1.8 (m, 19H) 2.30 (t, J=7.4 Hz, 2H) 2.42 (t, J=7.5 Hz, 2H) 2.4–2.7 (m, 3H) 2.8–2.95 (m, 1H) 3.1–3.2 (m, 1H) 3.66 (s, 3H) 4.2–4.25 (m, 2H) 5.53 (dd, J=15.5 & 8.6 Hz, 1H) 5.66 (ddd, J=15.5 & 6.3 & 2.0 Hz, 1H)

Example 86

Synthesis of methyl(11R,12S,13E)-9-butyryloxy-11,15-dihydroxy-16-cyclohexyl-17,18,19,20-tetranor-7-thiaprosta-8,13-dienoate ($R^1$=Pr, $R^2$=H, $R^3$=H, $R^4$= cyclohexylmethyl, W=OH, X—Y=CH$_2$—CH$_2$, Z= CO$_2$Me, n=0, ═══trans-CH═CH)

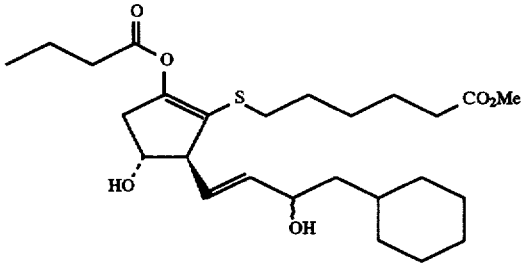

Using as the material and reagent a hydrogen fluoride-pyridine solution (0.4 ml) and methyl(11R,12S,13E)-9-butyryloxy-11-tert-butyldimethylsiloxyl-15-hydroxy-16-cyclohexyl-17,18,19,20-tetranor-7-thiaprosta-8,13-dienoate (140 mg), the same procedure as in Example 2 was performed to separately obtain two stereo isomers of methyl (11R,12S,13E)-9-butyryloxy-11,15-dihydroxy-16-cyclohexyl-17,18,19,20-tetranor-7-thiaprosta-8,13-dienoate different at the 15-position. (Low polarity compound: 44 mg, 40%; high polarity compound: 48 mg, 43%)

[Low polarity compound]

$^1$H-NMR (270 MHz, δppm, CDCl$_3$) 0.8–1.0 (m, 2H) 1.01 (t, J=7.5 Hz, 3H) 1.1–1.85 (m, 19H) 2.31 (t, J=7.5 Hz, 2H) 2.44 (t, J=7.3 Hz, 2H) 2.45–2.75 (m, 3H) 2.97 (ddd, J=16.5 & 6.6 & 1.3 Hz, 1H) 3.22 (d-like, J=7.9 Hz, 1H) 3.67 (s, 3H) 4.1–4.3 (m, 2H) 5.57 (dd, J=15.5 & 8.0 Hz, 1H) 5.72 (dd, J=15.5 & 6.3 Hz, 1H)

[High polarity compound]

$^1$H-NMR (270 MHz, δppm, CDCl$_3$) 0.8–1.0 (m, 2H) 1.01 (t, J=7.5 Hz, 3H) 1.0–1.8 (m, 19H) 2.31 (t, J=7.6 Hz, 2H) 2.43 (t, J=7.3 Hz, 2H) 2.4–2.75 (m, 3H) 2.94 (ddd, J=16.5 & 6.9 & 1.3 Hz, 1H) 3.21 (dd, J=8.0 & 1.5 Hz, 1H) 3.67 (s, 3H) 4.15–4.3 (m, 2H) 5.55 (dd, J=15.5 & 7.6 Hz, 1H) 5.68 (dd, J=15.5 & 6.4 Hz, 1H)

Example 87

Synthesis of methyl(13E,15S,17R)-9-butyryloxy-15-(tert-butyldimethylsiloxy)-17,20-dimethyl-7-thiaprosta-8,13-dienoate ($R^1$=Pr, $R^2$=$^t$BuMe$_2$Si, $R^3$= H, $R^4$=2-Me-hexyl, W=H, X—Y=CH$_2$—CH$_2$, Z= CO$_2$Me, n=0, ═══trans-CH═CH)

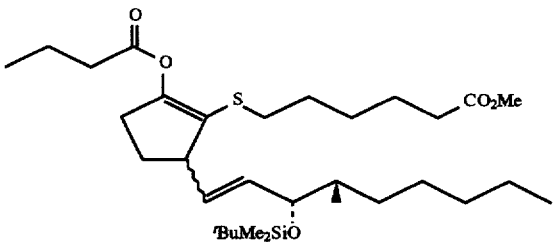

Using as the materials and reagents (1E,3S,5R)-1-iodo-3-(tert-butyldimethylsiloxy)-5-methyl-1-nonene (785 mg), tert-butyllithium (1.54 mol/l, 2.57 ml), 287 mg of 1-hexynylcopper, hexamethylphosphorous triamide (720 µl), 2-(5-methoxycarbonylpentylthio)-2-cyclopenten-1-one (400 mg), and butyric anhydride (729 µl), the same procedure was performed as in Example 1 to obtain methyl(13E, 15S,17R)-9-butyryloxy-15-(tert-butyldimethylsiloxy)-17,20-dimethyl-7-thiaprosta-8,13-dienoate (367 mg).

Note that the methyl(13E,15S,17R)-9-butyryloxy-15-(tert-butyldimethylsiloxy)-17,20-dimethyl-7-thiaprosta-8,13-dienoate thus obtained is a diastereomer mixture of mixed stereo isomers different at the 12-position.

$^1$H-NMR (270 MHz, δppm, CDCl$_3$) 0.04 (s, 6H) 0.84 (s, 9H) 0.8–0.9 (m, 6H) 0.96 (t, J=7.4 Hz, 3H) 1.1–1.8 (m, 19H) 2.1–2.7 (m, 4H) 2.23 (t, J=7.6 Hz, 2H) 2.38 (t, J=7.4 Hz, 2H) 3.63 (s, 3H) 4.1 (br, 1H) 5.4–5.5 (m, 2H)

Example 88

Synthesis of methyl(13E,15S,17R)-9-butyryloxy-15-hydroxy-17,20-dimethyl-7-thiaprosta-8,13-dienoate (R¹=Pr, R²=H, R³=H, R⁴=2-Me-hexyl, W=H, X—Y=CH₂—CH₂, Z=CO₂Me, n=0, ≔trans-CH═CH)

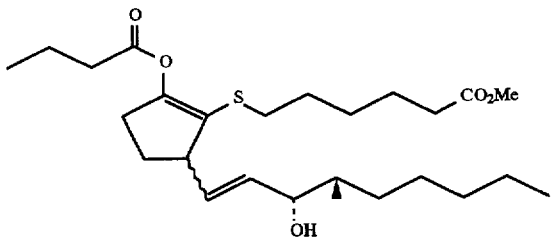

Using as the material and reagent a hydrogen fluoride-pyridine solution (0.4 ml) and methyl(13E,15S,17R)-9-butyryloxy-15-(tert-butyldimethylsiloxyl)-17,20-dimethyl-7-thiaprosta-8,13-dienoate (180 mg), the same procedure as in Example 2 was performed to separately obtain two stereo isomers of methyl(13E,15S,17R)-9-butyryloxy-15-hydroxy-17,20-dimethyl-7-thiaprosta-8,13-dienoate different at the 12-position. (Low polarity compound: 80 mg, 50%; high polarity compound: 29 mg, 20%)

[Low polarity compound]
¹H-NMR (270 MHz, δppm, CDCl₃) 0.8–0.95 (m, 6H) 1.00 (t, J=7.4 Hz, 3H) 1.1–1.8 (m, 19H) 2.15–2.3 (m, 1H) 2.30 (t, J=7.2 Hz, 2H) 2.43 (t, J=7.4 Hz, 2H) 2.45–2.75 (m, 4H) 3.3 (br, 1H) 3.67 (s, 3H) 4.2 (br, 1H) 5.5–6.9 (m, 2H)

[High polarity compound]
¹H-NMR (270 MHz, δppm, CDCl₃) 0.8–0.95 (m, 6H) 1.00 (t, J=7.3 Hz, 3H) 1.1–1.8 (m, 19H) 2.15–2.3 (m, 1H) 2.30 (t, J=7.3 Hz, 2H) 2.43 (t, J=7.3 Hz, 2H) 2.45–2.75 (m, 4H) 3.3 (br, 1H) 3.67 (s, 3H) 4.2 (br, 1H) 5.5–6.9 (m, 2H)

Example 89

Synthesis of methyl(11R,12S,13E,15S)-11,15-bis(tert-butyldimethylsiloxy)-9-(2,2-dimethyl-6-(4-chlorophenoxy)-hexanoyloxy)-7-thiaprosta-8,13-dienoate (R¹=C(CH₃)₂(CH₂)₄OPh-p-Cl, R²='BuMe₂Si, R³=H, R⁴=Pentyl, W='BuMe₂SiO, X—Y=CH₂—CH₂, Z=CO₂Me, n=0, ≔trans-CH═CH)

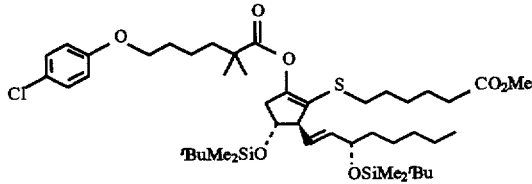

Using as the materials and reagents (1E,3S)-1-iodo-3-(tert-butyldimethylsiloxy)-1-octene (442 mg), tert-butyllithium (1.50 mol/l, 1.60 ml), 174 mg of 1-hexynylcopper, hexamethylphosphorous trimide (436 μl), (4R)-tert-butyldimethylsiloxy-2-(5-methoxcarbonylprtylthio)-2-cyclopenten-1-one (373 mg, 1.0 mmol), and 2,2-dimethyl-6-(4-chorophenoxy)-hexanoxyl choride (781 μl), the same procedure was performed as in Example 1 to obtain methyl(11R,12S,13E,15S)-11,15-bis(tert-butyldimethylsiloxy)-9-(2,2-dimethyl-6-(4-chlorophenoxy)-hexanoyloxy)-7-thiaprosta-8,13-dienoate (520 mg, 60%).

¹H-NMR (270 MHz, δppm, CDCl₃) −0.05 (s, 6H) −0.01 (s, 6H) 0.83 (s, 9H) 0.84 (s, 9H) 1.21 (s, 6H) 1.1–1.8 (m, 19H) 1.32 (t, J=6.0 Hz, 2H) 2.27–2.47 (m, 2H) 2.5–2.65 (m, 2H) 2.82 (ddd, J=16.1 & 6.9 & 1.3 Hz, 1H) 3.08 (dd, J=8.6 Hz, 1H) 3.61 (s, 3H) 3.87 (t, J=16.3 Hz, 2H) 4.0–4.15 (m, 2H) 5.38 (dd, J=15.5 & 8.6 Hz, 1H) 5.57 (dd, J=15.5 & 6.0 Hz, 1H) 6.75 (d, J=8.9 Hz, 2H) 7.16 (d, J=8.9 Hz, 2H)

Example 90

Synthesis of methyl(11R,12S,13E,15S)-9-(2,2-dimethyl-6-(4-chlorophenoxy)-hexanoyloxy)-11,15-dihydroxy-7-thiaprosta-8,13-dienoate (R¹=C (CH₃)₂(CH₂)₄OPh-p-Cl R²=H, R³=H, R⁴=Pentyl W=OH, X—Y=CH₂CH₂, Z=CO₂Me, n=0, ≔trans-CH═CH)

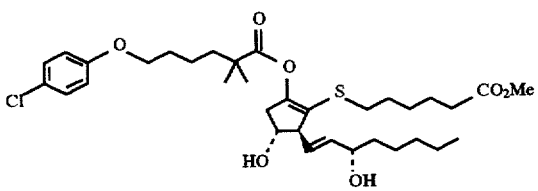

As the materials and reagent, adding a hydrogen fluoride-pyridine solution (0.5 ml) and using methyl(11R,12S,13E,15S)-11,15-bis(tert-butyldimethylsiloxyl)-9-(2,2-dimethyl-6-(4-chlorophenoxy)-hexanoyloxy)-7-thiaprosta-8,13-dienoate (538 mg), the same procedure was performed as in Example 2 to obtain methyl(11R,12S,13E,15S)-9-(2,2-dimethyl-6-(4-chlorophenoxy)-hexanoyloxy)-11,15-dihydroxy-7-thiaprosta-8,13-dienoate (240 mg, 75%).

¹H-NMR (270 MHz, δppm, CDCl₃) 0.88 (t, J=6.5 Hz, 3H) 1.26 (s, 6H) 1.2–1.8 (m, 20H) 2.29 (t, J=7.4 Hz, 2H) 2.35–2.7 (m, 3H) 2.90 (dd, J=5.3 & 16.5 Hz, 1H) 3.22 (br-d, J=7.9 Hz, 1H) 3.66 (s, 3H) 3.92 (t, J=6.4 Hz, 2H) 4.05–4.2 (m, 2H) 5.55 (dd, J=7.9 & 15.5 Hz, 1H) 5.70 (dd, J=6.3 & 15.5 Hz, 1H) 6.80 (d, J=8.9 Hz, 2H) 7.21 (d, J=8.9 Hz, 2H)

Example 91

Synthesis of methyl(11R,12S,13E)-9-butyryloxy-11-tert-butyldimethylsiloxy-15-hydroxy-16-(3-methoxyphenyl)-17,18,19,20-tetranor-7-thiaprosta-8,13-dienoate (R¹=Pr, R²=H, R³=H, R⁴=3-MeO-Benzyl, W='BuMe₂SiO, X—Y=CH₂—CH₂, Z=CO₂Me, n=0, ≔trans-CH═CH)

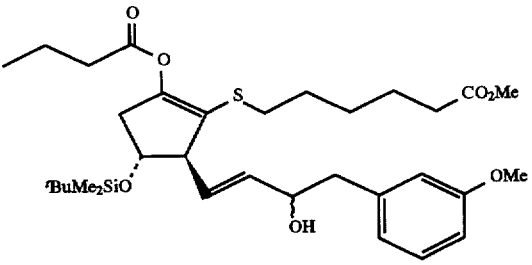

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (415 mg), chromium(II) chloride (435 mg), nickel chloride (0.1 mg), and (3-methoxyphenyl)acetoaldehyde (253 mg), the same procedure was performed as in Example 39 to obtain methyl(11R,12S,13E)-9-butyryloxy-11-tert-butyldimethylsiloxy-15-hydroxy-16-(3-methoxyphenyl)-17,18,19,20-tetranor-7-thiaprosta-8,13-dienoate (269 mg, 62%)

Note that the methyl(11R,12S,13E)-9-butyryloxy-11-tert-butyldimethylsiloxy-15-hydroxy-16-(3-methoxyphenyl)-17,18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.04 (s, 6H) 0.87 (s, 9H) 1.01 (t, J=7.6 Hz, 3H) 1.3–1.8 (m, 8H) 2.30 (t, J=7.3 Hz, 2H) 2.43 (t, J=7.3 Hz, 2H) 2.4–2.9 (m, 6H) 3.14 (br-d, J=7.3 Hz, 1H) 3.66 (s, 3H) 3.80 (s, 3H) 4.06–4.11 (m, 1H) 4.31–4.44 (m, 1H) 5.51–5.65 (m, 1H) 5.67–5.82 (m, 1H) 6.75–6.85 (m, 3H) 7.18–7.25 (m, 1H)

Example 92

Synthesis of methyl(11R,12S,13E)-9-butyryloxy-11,15-dihydroxy-16-(3-methoxyphenyl)-17,18,19,20-tetranor-7-thiaprosta-8,13-dienoate (R$^1$=Pr, R$^2$=H, R$^3$=H, R$^4$=3-MeO-Benzyl, W=OH, X—Y=CH$_2$—CH$_2$, Z=CO$_2$Me, n=0, ==trans-CH==CH)

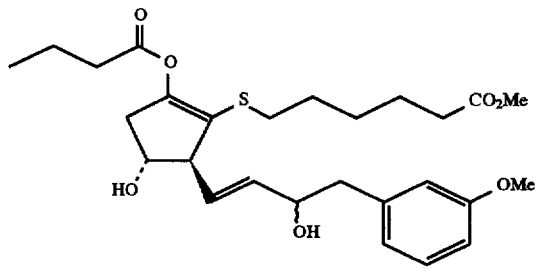

Using as the material and reagent a hydrogen fluoride-pyridine solution (0.5 ml) and methyl(11R,12S,13E)-9-butyryloxy-11-tert-butyldimethylsiloxyl-15-hydroxy-16-(3-methoxyphenyl)-17,18,19,20-tetranor-7-thiaprosta-8,13-dienoate (262 mg), the same procedure as in Example 2 was performed to separately obtain two stereo isomers of methyl (11R,12S,13E)-9-butyryloxy-11,15-dihydroxy-16-(3-methoxyphenyl)-17,18,19,20-tetranor-7-thiaprosta-8,13-dienoate different at the 15-position. (Low polarity compound: 74 mg, 35%; high polarity compound: 92 mg, 43%)

[Low polarity compound]

$^1$H-NMR (270 MHz, δppm, CDCl$_3$) 1.00 (t, J=7.6 Hz, 3H) 1.3–1.8 (m, 8H) 1.88 (br, 1H) 2.17 (br, 1H) 2.31 (t, J=7.3 Hz, 2H) 2.43 (t, J=7.3 Hz, 2H) 2.40–2.72 (m, 3H) 2.82 (d, J=6.6 Hz, 2H) 2.90 (ddd, J=16.5 & 6.6 & 1.3 Hz, 1H) 3.19 (dd, J=8.6 & 2.3 Hz, 1H) 3.74 (s, 3H) 3.80 (s, 3H) 3.95–4.05 (br, 1H) 4.30–4.42 (m, 1H) 5.50 (ddd, J=15.5 & 8.6 & 1.0 Hz, 1H) 5.75 (dd, J=15.5 & 6.3 Hz, 1H) 6.74–6.83 (m, 3H) 7.15–7.25 (m, 1H)

[High polarity compound]

$^1$H-NMR (270 MHz, δppm, CDCl$_3$) 1.01 (t, J=7.6 Hz, 3H) 1.3–1.8 (m, 8H) 1.88 (br, 1H) 2.30 (t, J=7.3 Hz, 2H) 2.36 (br, 1H) 2.44 (t, J=7.3 Hz, 2H) 2.35–2.97 (m, 6H) 3.20 (dd, J=8.3 & 2.4 Hz, 1H) 3.66 (s, 3H) 3.80 (s, 3H) 4.04–4.12 (br, 1H) 4.31–4.43 (m, 1H) 5.58 (dd, J=15.5 & 8.2 Hz, 1H) 5.75 (dd, J=15.5 & 5.9 Hz, 1H) 6.73–6.85 (m, 3H) 7.15–7.25 (m, 1H)

Example 93

Synthesis of methyl(11R,12S,13E)-9-butyryloxy-11-tert-butyldimethylsiloxy-15-hydroxy-16-(3-methoxycarbonylphenyl)-17,18,19,20-tetranor-7-thiaprosta-8,13-dienoate (R$^1$=Pr, R$^2$=H, R$^3$=H, R$^3$=3-MeO$_2$C-Benzyl, W=$^t$BuMe$_2$SiO, X—Y=CH$_2$—CH$_2$, Z=CO$_2$Me, n=0, ==trans-CH==CH)

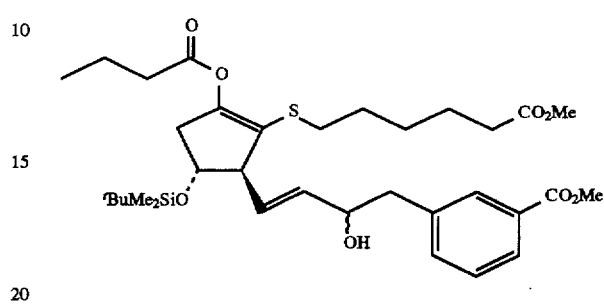

Using as the materials and reagents (3S,4R)-4-(tert-butyldimethylsiloxy)-1-butyryloxy-2-(5-methoxycarbonylpentylthio)-3-(trans-2-iodovinyl)-1-cyclopentene (360 mg), chromium(II) chloride (433 mg), nickel chloride (0.1 mg), and methyl 3-(formylmethyl)benzoate (251 mg), the same procedure was performed as in example 39 to obtain methyl(11R,12S,13E)-9-butyryloxy-11-tert-butyldimethylsiloxy-15-hydroxy-16-(3-methoxycarbonylphenyl)-17,18,19,20-tetranor-7-thiaprosta-8,13-dienoate (141 mg, 36%).

Note that the methyl(11R,12S,13E)-9-butyryloxy-11-tert-butyldimethylsiloxy-15-hydroxy-16-(3-methoxycarbonylphenyl)-17,18,19,20-tetranor-7-thiaprosta-8,13-dienoate thus obtained is a diastereomer mixture of mixed stereo isomers of different hydroxyl groups at the 15-position.

$^1$H-NMR (270 MHz, δppm, CDCl$_3$) 0.02 (s, 3) 0.03 (s, 3) 0.87 (s, 9H) 1.01 (t, J=7.6 Hz, 3H) 1.3–1.8 (m, 8H) 2.30 (t, J=7.3 Hz, 2H) 2.43 (t, J=7.3 Hz, 2H) 2.37–2.70 (m, 3H) 2.80–2.92 (m, 3H) 3.13 (br-d, J=7.9 Hz, 1H) 3.9 (s, 3H) 3.80 (s, 3H) 4.02–4.10 (m, 1H) 4.34–4.45 (m, 1H) 5.57 (dd, J=15.5 & 8.3 Hz, 1H) 5.5.68–5.80 (m, 1H) 7.33–6.48 (m, 2H) 7.89–7.93 (m, 2H)

Example 94

Synthesis of methyl(11R,12S,13E)-9-butyryloxy-11,15-dihydroxy-16-(3-methoxycarbonylphenyl)-17,18,19,20-tetranor-7-thiaprosta-8,13-dienoate (R$^1$=Pr, R$^2$=H, R$^3$=H, R$^4$=3-MeO$_2$C-Benzyl, W=OH, X—Y=CH$_2$—CH$_2$, Z=CO$_2$Me, n=0, ==trans-CH==CH)

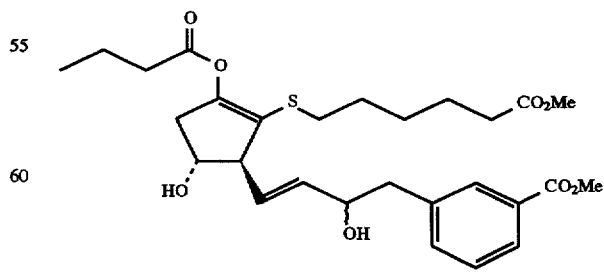

Using as the material and reagent a hydrogen fluoride-pyridine solution (0.3 ml) and methyl(11R,12S,13E)-9- butyryloxy-11-tert-butyldimethylsiloxyl-15-hydroxy-16-(3-methoxycarbonylphenyl)-17,18,19,20-tetranor-7-thiaprosta-8,13-dienoate (137 mg), the same procedure as in Example 2 was performed to separately obtain two stereo isomers of methyl(11R,12S,13E)-9-butyryloxy-11,15-dihydroxy-16-(3-methoxycarbonylphenyl)-17,18,19,20-tetranor-7-thiaprosta-8,13-dienoate different at the 15-position. (Low polarity compound: 31 mg, 28%; high polarity compound: 52 mg, 46%)

[Low polarity compound]

$^1$H-NMR (270 MHz, δppm, CDCl$_3$) 1.00 (t, J=7.6 Hz, 3H) 1.3–1.8 (m, 8H) 1.92 (br-d, J=4.0 Hz, 1H) 2.31 (t, J=7.3 Hz, 2H) 2.42 (t, J=7.3 Hz, 2H) 2.44 (br, 1H) 2.45–2.72 (m, 3H) 2.80–3.00 (m, 3H) 3.21 (dd, J=8.6 & 3.3 Hz, 1H) 3.66 (s, 3H) 3.92 (s, 3H) 3.95–4.05 (m, 1H) 4.30–4.41 (m, 1H) 5.45 (dd, J=15.5 & 8.6 Hz, 1H) 5.75 (dd, J=15.5 & 6.9 Hz, 1H) 7.32–7.47 (m, 2H) 7.86–7.92 (m, 2H)

[High polarity compound]

$^1$H-NMR (270 MHz, δppm, CDCl$_3$) 1.01 (t, J=7.3 Hz, 3H) 1.3–1.8 (m, 8H) 1.87 (br, 1H) 2.30 (t, J=7.3 Hz, 2H) 2.40–2.70 (m, 3H) 2.43 (t, J=7.3 Hz, 2H) 2.48 (br, 1H) 2.81–2.98 (m, 3H) 3.20 (dd, J=8.3 & 2.0 Hz, 1H) 3.66 (s, 3H) 3.91 (s, 3H) 4.02–4.10 (br, 1H) 4.35–4.47 (m, 1H) 5.55 (ddd, J=15.5 & 8.3 & 1.0 Hz, 1H) 5.76 (dd, J=15.5 & 5.9 Hz, 1H) 7.32–7.47 (m, 2H) 7.85–7.93 (m, 2H)

Example 95

Synthesis of (11R,12S,13E,15S)-9-butyryloxy-11,15-bis(tert-butyldimethylsiloxy)-7-thiaprosta-8,13-dienamide (R$^1$=Pr, R$^2$=$^t$BuMe$_2$Si, R$^3$=H, R$^4$=pentyl, W=$^t$BuMe$_2$SiO, X—Y=CH$_2$—CH$_2$, Z=CONH$_2$, n=0, ═=trans-CH═CH)

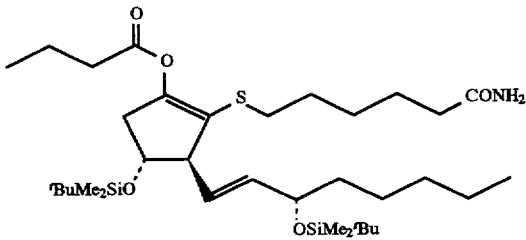

A methylene chloride (3 ml) solution of (11R,12S,13E,15S)-9-butyryloxy-11,15-bis(tert-butyldimethylsiloxy)-7-thiaprosta-8,13-dienoic acid (201 mg) was cooled to −40° C., then isobutyl chloroformate (47 µl) and triethylamine (63 µl) were added to the solution which was then stirred as is at −40° C. for 30 minutes. Further 1 ml of 30% ammonium hydroxide solution was added and the mixture was stirred overnight while raising the temperature to room temperature. The reaction solution was diluted by ethyl acetate then was neutralized by dilute hydrochloric acid. The desired substance was extracted from the mixture by ethyl acetate and extract was successively washed by saturated sodium hydrogen carbonate and saturated sodium chloride solution. This solution was concentrated under reduced pressure, then was purified by silica gel column chromatography (45% ethyl acetate/hexane) to obtain (11R,12S,13E,15S)-9-butyryloxy-11,15-bis(tert-butyldimethylsiloxy)-7-thiaprosta-8,13-dienamide (169 mg, 84%).

$^1$H-NMR (270 MHz, δppm, CDCl$_3$) 0.04 (s), 0.05 (s) . . . . . . 12H 0.8–0.9 (m, 3H) 0.88 (s, 9H) 0.89 (s, 9H) 1.00 (t, J=7.4 Hz, 3H) 1.2–1.8 (m, 16H) 2.20 (t, J=7.4 Hz, 2H) 2.4–2.7 (m, 3H) 2.42 (t, J=7.4 Hz, 2H) 2.89 (dd, J=6.9 & 16.2 Hz, 1H) 3.13 (d, J=5.8 Hz, 1H) 4.0–4.2 (m, 2H) 5.43 (dd, J=8.7 & 15.3 Hz, 1H) 5.5–5.7 (m, 2H) 5.62 (dd, J=5.8 & 15.3 Hz, 1H)

Example 96

Synthesis of (11R,12S,13E,15S)-9-butyryloxy-11,15-dihydroxy-7-thiaprosta-8,13-dienamide (R$^1$=Pr, R$^2$=H, R$^3$=H, R$^4$=Pentyl, W=OH, X—Y=CH$_2$—CH$_2$, Z=CONH$_2$, n=0, ═=trans-CH═CH)

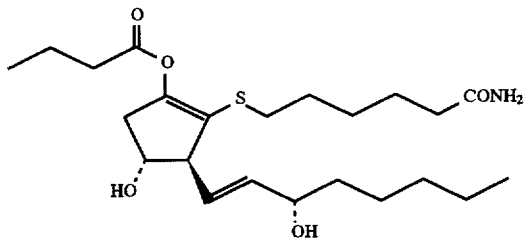

Using as the material and reagent a hydrogen fluoride-pyridine solution (0.2 ml) and (11R,12S,13E,15S)-9-butyryloxy-11,15-bis(tert-butyldimethylsiloxy)-7-thiaprosta-8,13-dienamide (169 mg), the same procedure was followed as in Example 2 to obtain (11R,12S,13E,15S)-9-butyryloxy-11,15-dihydroxy-7-thiaprosta-8,13-dienamide (101 mg, 91%).

$^1$H-NMR (270 MHz, δppm, CDCl$_3$) 0.88 (t, J=6.6 Hz, 3H) 1.01 (t, J=7.4 Hz, 3H) 1.2–1.8 (m, 16H) 2.22 (t, J=7.3 Hz, 2H) 2.4–2.8 (m, 3H) 2.44 (t, J=7.4 Hz, 2H) 2.90 (ddd, J=1.2 & 6.1 & 10.9 Hz, 1H) 3.23 (dd, J=2.8 & 8.1 Hz, 1H) 4.09 (dt, J=6.6 & 6.6 Hz, 1H) 4.1–4.2 (m, 1H) 5.54 (dd, J=7.9 & 15.5 Hz, 1H) 5.68 (dd, J=6.6 & 15.5 Hz, 1H) 5.80 (br.s, 1H) 5.92 (br.s, 1H)

Example 97

Synthesis of N,N-diethyl(11R,12S,13E,15S)-9-butyryloxy-11,15-bis(tert-butyldimethylsiloxy)-7-thiaprosta-8,13-dienamide (R$^1$=Pr, R$^2$=$^t$BuMe$_2$Si, R$^3$=H, R$^4$=Pentyl, W=$^t$BuMe$_2$SiO, X—Y=CH$_2$—CH$_2$, Z=CONEt$_2$, n=0, ═=trans-CH═CH)

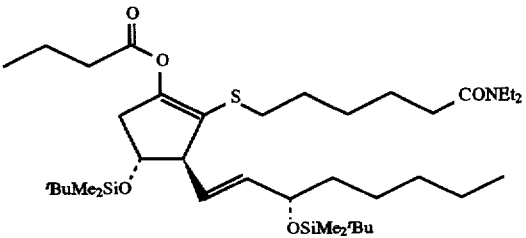

Using as the materials and reagents (11R,12S,13E,15S)-9-butyryloxy-11,15-bis(tert-butyldimethylsiloxy)-7-thiaprosta-8,13-dienoic acid (201 mg), isobutyl chloroformate (47 µl), triethylamine (63 µl), and diethylamine (37 µl), the same procedure was performed as in Example 95 to obtain N,N-diethyl(11R,12S,13E,15S)-9-butyryloxy-11,15-bis(tert-butyldimethylsiloxyl)-7-thiaprosta-8,13-dienamide (189 mg, 87%).

$^1$H-NMR (270 MHz, δppm, CDCl$_3$) 0.04 (s), 0.05 (s) . . . 12H 0.8–0.9 (m, 3H) 0.87 (s, 9H) 0.89 (s, 9H) 1.00 (t, J=7.4 Hz, 3H) 1.10 (t, J=7.1Hz, 3H) 1.17 (t, J=7.3 Hz, 3H) 1.2–1.8

(m, 16H) 2.28 (t, J=7.6 Hz, 2H) 2.4–2.7 (m, 3H) 2.42 (t, J=7.3 Hz, 2H) 2.91 (ddd, J=1.6 & 6.9 & 16.2 Hz, 1H) 3.13 (dd, J=2.6 & 8.6 Hz, 1H) 3.29 (q, J=7.3 Hz, 2H) 3.32 (q, J=6.9 Hz, 2H) 4.0–4.2 (m, 2H) 5.43 (ddd, J=0.7 & 8.6 & 15.2 Hz, 1H) 5.62 (dd, J=5.9 & 15.5 Hz, 1H)

Example 98

Synthesis of N,N-diethyl(11R,12S,13E,15S)-9-butyryloxy-11,15-dihydroxy-7-thiaprosta-8,13-dienamide ($R^1$=Pr, $R^2$=H, $R^3$=H, $R^4$=Pentyl, W=OH, X—Y=$CH_2$—$CH_2$, Z=$COEt_2$, n=0, =trans-CH=CH)

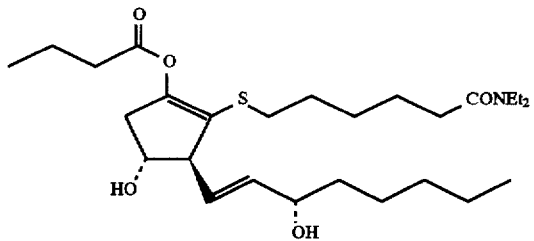

Using as the material and reagent a hydrogen fluoride-pyridine solution (0.2 ml) and N,N-diethyl(11R,12S,13E,15S)-9-butyryloxy-11,15-bis(tert-butyldimethylsiloxy)-7-thiaprosta-8,13-dienamide (169 mg), the same procedure as in Example 2 was performed to obtain N,N-diethyl(11R,12S,13E,15S)-9-butyryloxy-11,15-dihydroxy-7-thiaprosta-8,13-dienamide (101 mg, 78%).

$^1$H-NMR (270 MHz, δppm, $CDCl_3$) 0.88 (t, J=6.8 Hz, 3H) 1.00 (t, J=7.3 Hz, 3H) 1.11 (t, J=7.1 Hz, 3H) 1.17 (t, J=7.1 Hz, 3H) 1.2–1.8 (m, 16H) 2.28 (t, J=7.6 Hz, 2H) 2.4–2.7 (m, 3H) 2.43 (t, J=7.3 Hz, 2H) 2.91 (ddd, J=1.0 & 6.8 & 16.3 Hz, 1H) 3.2–3.4 (m, 5H) 4.08 (dt, J=6.6 & 6.6 Hz, 1H) 4.0–4.2 (m, 1H) 5.56 (dd, J=8.1 & 15.3 Hz, 1H) 5.68 (dd, J=6.4 & 15.3 Hz, 1H)

Example 99

Measurement of Activity for Inhibiting Cell Migration Induced by MCP-1

The cell migration induced by the monocyte chemoattractant protein MCP-1/MCAF was measured for the purpose of investigating the activity of the tested compounds shown in Table 1 in inhibiting cell migration by the following manner in accordance with the method of Falk et al. (J. Immunol. Methods, 33, 239–247 (1980)) using human promonocytic leukemia cell line, THP-1 (ATCC TIB203). That is, THP-1 cells diluted to 2×10$^6$/ml by 10% fetal calf serum: FCS-containing RPMI-1640 medium (made by Flow Laboratories) were added to the upper chamber (200 μl) of the 96-well microchemotaxis chamber (made by Neuroprobe Inc.) while recombinant human MCP-1 (made by Peprotech Co.) diluted by the same medium to a final concentration of 20 ng/ml was added to the bottom chamber (35 μl). A polycarbonate filter (pore size of 5 μm, PVP-free, made by Neuroprobe Co) was affixed between the two. Incubation was performed at 37° C. in the presence of 5% $CO_2$ for two hours. The filter was taken out, then the cells migrating to the bottom surface of the filter were fixed and stained by a Diff Quick solution (made by International Reagents Co.), then were measured by a plate reader (made by Molecular Device Co.) at a measurement wavelength of 550 nm. The mean value of three wells was determined and used as the indicator of the number of the migrating cells. At this time, the text compounds were added at various concentrations along with the THP-1 cells to the top chambers and the activity in inhibiting cell migration was determined. The percent of inhibition of cell migration was found by dividing the {(number of migrating cells caused by the MCP-1 added to the bottom chamber in the case of the test compound being added to the top chamber)—(number of migrating cells in the case of no test compound being added to the top chamber and no MCP-1 being added to the bottom chamber)} by the {(number of migrating cells caused by the MCP-1 added to the bottom chamber in the case of no test compound being added to the top chamber)—(number of migrating cells in the case of no test compound being added to the top chamber and no MCP-1 being added to the bottom chamber)}. The results when the concentration of the compound exhibiting 50% inhibition was made an inhibition of $IC_{50}$ are shown in Tables 1 to 9.

Further the results of investigation of the activity of the test compounds in inhibiting cell migration when using human blood monocytes instead of THP-1 cells but otherwise using exactly the same method are shown in Table 10.

TABLE 1

| Cell Migration Inhibiting Activity | |
|---|---|
| Test Compound | $IC_{50}$ (M) |
|  | 1.8 × 10$^{-12}$ |

TABLE 1-continued

Cell Migration Inhibiting Activity

| Test Compound | $IC_{50}$ (M) |
|---|---|
| [structure: acetate ester prostaglandin analog with S-linked $CO_2Me$ chain, methylated side chain] | $2.3 \times 10^{-12}$ |
| [structure: isobutyrate ester prostaglandin analog with S-linked $CO_2Me$ chain, methylated side chain] | $3.2 \times 10^{-13}$ |
| [structure: pivalate ester prostaglandin analog with S-linked $CO_2Me$ chain, methylated side chain] | $2.5 \times 10^{-12}$ |
| [structure: benzoate ester prostaglandin analog with S-linked $CO_2Me$ chain] | $3.9 \times 10^{-12}$ |
| [structure: Cbz-phenylalanine ester prostaglandin analog with S-linked $CO_2Me$ chain] | $2.2 \times 10^{-10}$ |
| [structure: butyrate ester prostaglandin analog with S-linked $CO_2Me$ chain] | $6.4 \times 10^{-13}$ |

TABLE 2

Cell Migration Inhibiting Activity

| Test Compound | $IC_{50}$ (M) |
|---|---|
| (structure 1) | $5.1 \times 10^{-10}$ |
| (structure 2) | $1.7 \times 10^{-9}$ |
| (structure 3) | $2.5 \times 10^{-9}$ |
| (structure 4) | $1.0 \times 10^{-7}$ |
| (structure 5) | $6.1 \times 10^{-12}$ |
| (structure 6) | $8.1 \times 10^{-10}$ |

TABLE 2-continued
Cell Migration Inhibiting Activity
| Test Compound | $IC_{50}$ (M) |
|---|---|
| 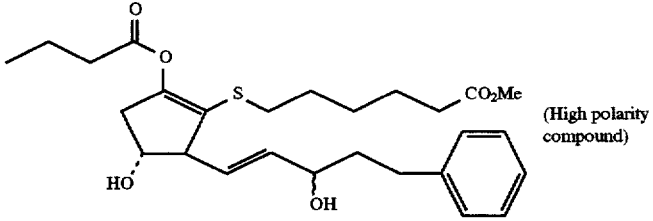 (High polarity compound) | $8.5 \times 10^{-9}$ |
TABLE 3
Cell Migration Inhibiting Activity
| Test Compound | $IC_{50}$ (M) |
|---|---|
| 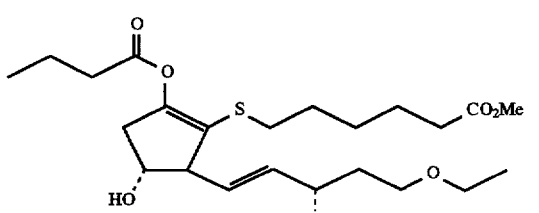 | $1.2 \times 10^{-7}$ |
| 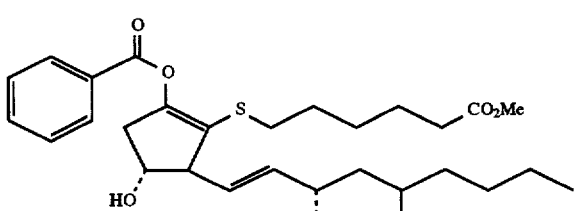 | $8.1 \times 10^{-7}$ |
| 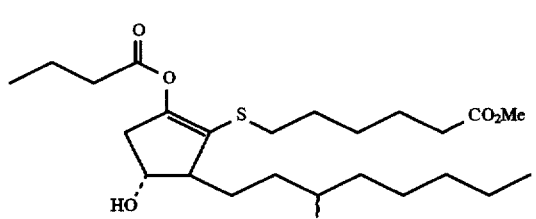 | $1.4 \times 10^{-10}$ |
| 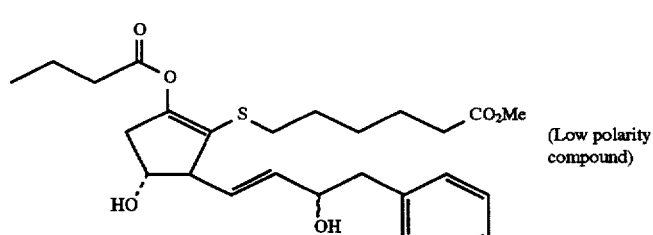 (Low polarity compound) | $8.3 \times 10^{-9}$ |

TABLE 3-continued

Cell Migration Inhibiting Activity

| Test Compound | | $IC_{50}$ (M) |
|---|---|---|
| [Structure: cyclopentene with butyryloxy, S-(CH2)5-CO2Me, HO, OH, CH=CH-CH(OH)-CH2-Ph] | (High polarity compound) | $8.0 \times 10^{-13}$ |
| [Structure: cyclopentene with butyryloxy, S-(CH2)5-CO2Me, HO, OH, CH=CH-CH(OH)-C(CH3)2-C5H11] | (Low polarity compound) | $1.7 \times 10^{-8}$ |
| [Structure: cyclopentene with butyryloxy, S-(CH2)5-CO2Me, HO, OH, CH=CH-CH(OH)-C(CH3)2-C5H11] | (High polarity compound) | $1.2 \times 10^{-8}$ |

TABLE 4

Cell Migration Inhibiting Activity

| Test Compound | | $IC_{50}$ (M) |
|---|---|---|
| [Structure: cyclopentene with butyryloxy, S-(CH2)5-CO2Me, HO, OH, CH=CH-CH(OH)-C(CH3)2-Ph] | (Low polarity compound) | $1.0 \times 10^{-7}$ |
| [Structure: cyclopentene with butyryloxy, S-(CH2)5-CO2Me, HO, OH, CH=CH-CH(OH)-C(CH3)2-Ph] | (High polarity compound) | $1.3 \times 10^{-8}$ |

TABLE 4-continued

Cell Migration Inhibiting Activity

| Test Compound | IC$_{50}$ (M) |
|---|---|
| [structure] (Low polarity compound) | $3.0 \times 10^{-9}$ |
| [structure] (High polarity compound) | $8.3 \times 10^{-12}$ |
| [structure] (Low polarity compound) | $6.0 \times 10^{-9}$ |
| [structure] (High polarity compound) | $2.1 \times 10^{-11}$ |
| [structure] | $2.1 \times 10^{-9}$ |

TABLE 5
Cell Migration Inhibiting Activity
| Test Compound | IC$_{50}$ (M) |
|---|---|
| 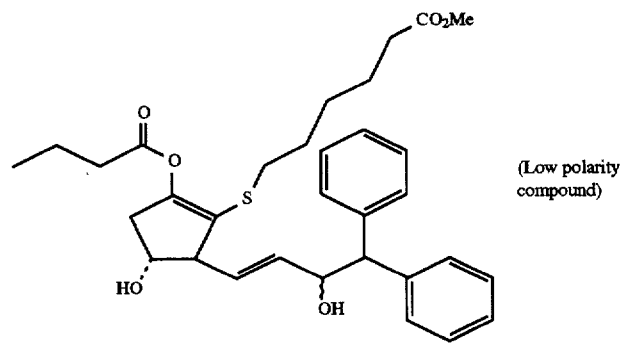 (Low polarity compound) | $1.3 \times 10^{-6}$ |
| 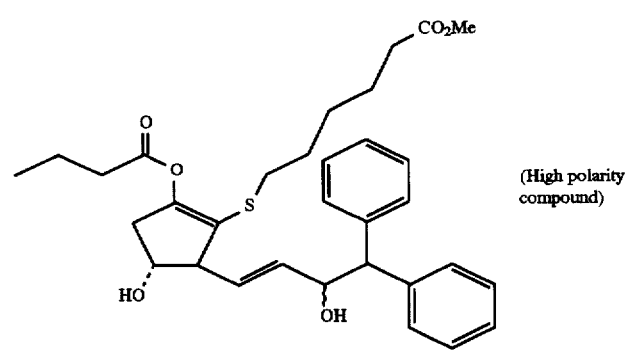 (High polarity compound) | $>5.0 \times 10^{-6}$ |
| 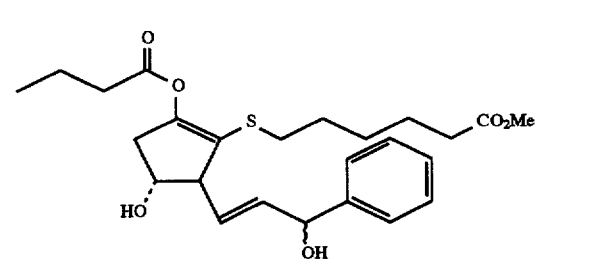 | $>1.0 \times 10^{-6}$ |
| 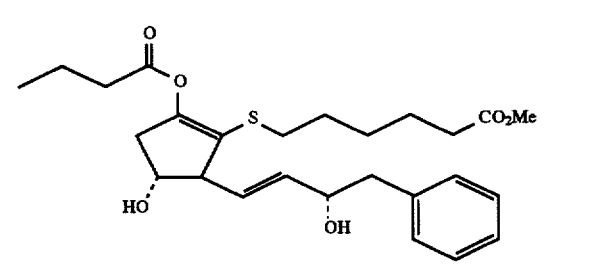 | $1.1 \times 10^{-9}$ |
| 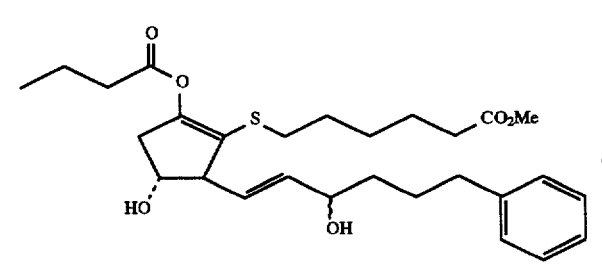 (Low polarity compound) | $3.0 \times 10^{-7}$ |

TABLE 5-continued

Cell Migration Inhibiting Activity

| Test Compound | | $IC_{50}$ (M) |
|---|---|---|
| [structure: cyclopentene with butyryloxy, S-(CH2)5-CO2Me, OH, and CH=CH-CH(OH)-(CH2)3-phenyl side chains] | (High polarity compound) | $4.3 \times 10^{-9}$ |

TABLE 6

Cell Migration Inhibiting Activity

| Test Compound | | $IC_{50}$ (M) |
|---|---|---|
| [structure: cyclopentene with butyryloxy, S-(CH2)5-CO2Me, OH, and CH=CH-CH(OH)-CH2-(4-methylphenyl) side chains] | (Low polarity compound) | $>1.0 \times 10^{-5}$ |
| [structure: cyclopentene with butyryloxy, S-(CH2)5-CO2Me, OH, and CH=CH-CH(OH)-CH2-(4-methylphenyl) side chains] | (High polarity compound) | $1.0 \times 10^{-7}$ |
| [structure: cyclopentene with butyryloxy, S-CH2CH2-CH=CH-CO2Me, OH, and CH=CH-CH(OH)-CH2-CH(CH3)-(CH2)3CH3 side chains] | | $6.0 \times 10^{-9}$ |
| [structure: cyclopentene with butyryloxy, S-(CH2)5-CO2Me, OH, and CH=CH-CH(OH)-CH2-(thiophen-3-yl) side chains] | (Low polarity compound) | $9.0 \times 10^{-8}$ |

TABLE 6-continued

Cell Migration Inhibiting Activity

| Test Compound | | $IC_{50}$ (M) |
|---|---|---|
| [Structure: cyclopentane with butyryloxy, S-(CH2)5-CO2Me, vinyl-CH(OH)-CH2-thiophene, and OH substituents] (High polarity compound) | | $8.0 \times 10^{-11}$ |

TABLE 7

Cell Migration Inhibiting Activity

| Test Compound | | $IC_{50}$ (M) |
|---|---|---|
| [Structure: cyclopentane with butyryloxy, S-(CH2)4-CO2Me, vinyl-CH(OH)-CH2-(3-methylphenyl), and OH substituents] (Low polarity compound) | | $6.0 \times 10^{-7}$ |
| [Structure: cyclopentane with butyryloxy, S-(CH2)4-CO2Me, vinyl-CH(OH)-CH2-(3-methylphenyl), and OH substituents] (High polarity compound) | | $1.2 \times 10^{-9}$ |
| [Structure: cyclopentane with butyryloxy, S-(CH2)4-CO2Me, vinyl-CH(OH)-CH2-(3-chlorophenyl), and OH substituents] (Low polarity compound) | | $8.0 \times 10^{-9}$ |
| [Structure: cyclopentane with butyryloxy, S-(CH2)4-CO2Me, vinyl-CH(OH)-CH2-(3-chlorophenyl), and OH substituents] (High polarity compound) | | $4.0 \times 10^{-10}$ |

TABLE 7-continued
Cell Migration Inhibiting Activity
| Test Compound | | $IC_{50}$ (M) |
|---|---|---|
| 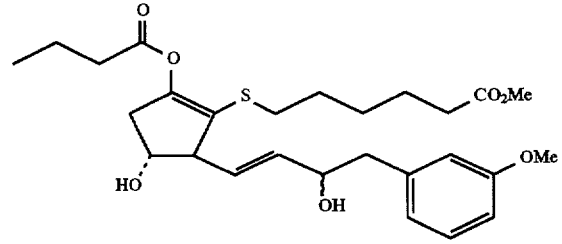 | (Low polarity compound) | $3.3 \times 10^{-8}$ |
| 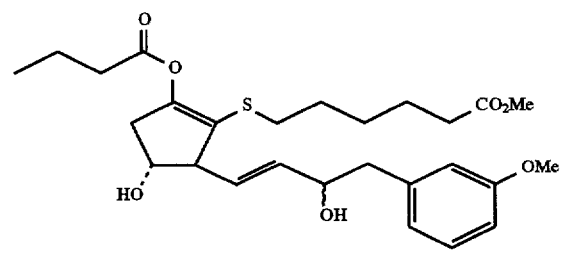 | (High polarity compound) | $2.3 \times 10^{-9}$ |
TABLE 8
Cell Migration Inhibiting Activity
| Test Compound | | $IC_{50}$ (M) |
|---|---|---|
| 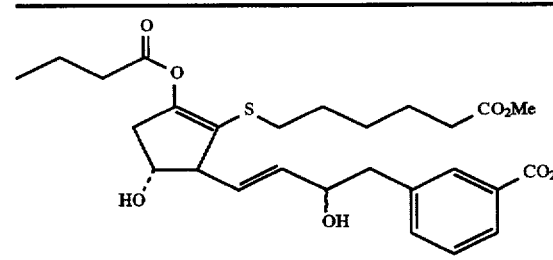 | (Low polarity compound) | $2.3 \times 10^{-7}$ |
| 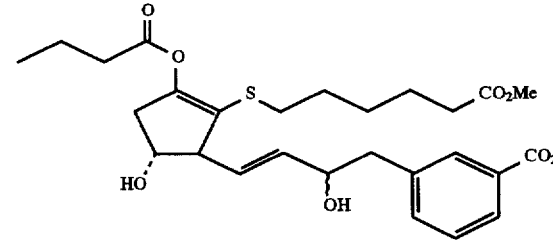 | (High polarity compound) | $2.3 \times 10^{-9}$ |
| 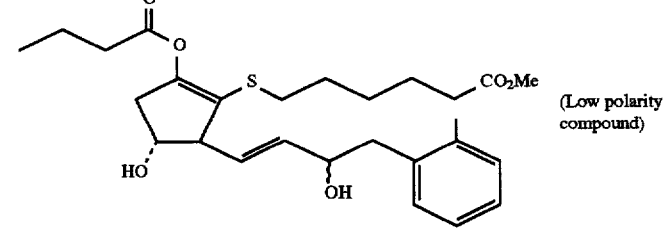 | (Low polarity compound) | $1.9 \times 10^{-7}$ |

TABLE 8-continued

Cell Migration Inhibiting Activity

| Test Compound | | $IC_{50}$ (M) |
|---|---|---|
| [Structure: cyclopentane with butyryloxy, S-(CH2)4-CO2Me, CH=CH-CH(OH)-CH2-(2-methylphenyl), HO] (High polarity compound) | | $4.4 \times 10^{-9}$ |
| [Structure: cyclopentane with butyryloxy, S-(CH2)4-CO2Me, CH=CH-CH(OH)-CH2-(4-nitrophenyl), HO] (Low polarity compound) | | $<1.0 \times 10^{-7}$ |
| [Structure: cyclopentane with butyryloxy, S-(CH2)5-CO2Me, CH=CH-CH(OH)-CH2-(4-nitrophenyl), HO] (High polarity compound) | | $3.6 \times 10^{-9}$ |

TABLE 9

Cell Migration Inhibiting Activity

| Test Compound | | $IC_{50}$ (M) |
|---|---|---|
| [Structure: cyclopentane with butyryloxy, S-(CH2)4-CO2Me, CH=CH-CH(OH)-CH2-(4-chlorophenyl), HO] (Low polarity compound) | | $<1.0 \times 10^{-7}$ |
| [Structure: cyclopentane with butyryloxy, S-(CH2)5-CO2Me, CH=CH-CH(OH)-CH2-(4-chlorophenyl), HO] (High polarity compound) | | $<1.0 \times 10^{-9}$ |

TABLE 9-continued

Cell Migration Inhibiting Activity

| Test Compound | | $IC_{50}$ (M) |
|---|---|---|
| [Structure: cyclopentane with butyryloxy, CO2Me chain, OH, and benzyl-CH(OH) groups] | (Low polarity compound) | $4.0 \times 10^{-6}$ |
| [Structure: cyclopentane with butyryloxy, CO2Me chain, OH, and benzyl-CH(OH) groups] | (High polarity compound) | $5.0 \times 10^{-9}$ |

TABLE 10

Cell Migration Inhibiting Activity

| Test Compound | $IC_{50}$ (M) |
|---|---|
| [Structure: cyclopentane with butyryloxy, S-linked CO2Me chain, OH, and benzyl-CH(OH) with methyl-pentyl group] | $1.0 \times 10^{-9}$ |

Reference Example

Preparation of Human Blood Monocytes

To 50 ml of human peripheral blood was added an equal amount of saline. This was superposed on Ficoll-paque (Farmacia) returned to room temperature in advance. The amount of the Ficoll-paque was made 17 ml with respect to the 25 ml of the peripheral blood dilution per tube. The solution was centrifuged at room temperature and 400 G for 30 minutes, then the intermediate layer was sucked up slowly by a pipette and a 2-fold volume of saline was added. The solution was centrifuged at 200G for 10 minutes to obtain cell pellets. Saline in an amount of 10 ml was added to the resultant cell pellets to make a suspension which was then centrifuged at 200 G for 10 minutes and washed, then 10 ml of 10% FCS-containing RPMI-1640 medium was added to create a good suspension. 5 ml each was placed in 10 cm petri dishes, then incubation was performed at 37° C. for one hour. The nonadhering cells were removed, then 5 ml of 10% FCS-added RPMI-1640 medium was used to wash the result three times. Vigorous pipetting was then performed so as to remove the adhered cells, then the resultant cell suspension was centrifuged at 200 G for 5 minutes to obtain cell pellets. Use was made of 10% FCS-added RPMI-1640 medium to prepare $2 \times 10^6$ /ml. The result was used as the human blood monocytes for the evaluation of the activity in inhibiting cell migration.

Example 100

Action in Suppressing Thickening of Intima After Trauma to Rat Carotid Artery Endothelium by Balloon Catheter Test compound:

Methyl(11R,12S,13E,15S,17R)-9-butyryloxy-11,15-dehydroxy-17,20-dimethyl-7-thiaprosta-8,13-dienoate The test was performed in the following manner in accordance with the method of Clowes et al. (Lab. Invest., 49, 206, 1983). Male Wistar rats of a body weight of 300 to 350 g were used. The neck of each rat was opened under anesthesia by sodium pentobarbitol, then a balloon catheter (Fogarty, 2F) was inserted from the right external carotid artery until the starting portion of the common carotid artery. The balloon was expanded by saline to an extent causing a light resistance, then the catheter was pulled out in that state up to the carotid artery to give trauma to the intima. This procedure was repeated three times, then the catheter was withdrawn and the external carotid artery was ligated. After 14 days, the chest was opened under anesthesia by diethyl ether, refluxing and immobilization were performed from the aorti arch by a Karnoa solution (methanol:chloroform:acetic acid=6:3:1), then the right common carotid artery was excised and immobilized by neutral formalin solution. The immobilized carotid artery was dyed by Elastica van Gieson dye, then the areas of the media and thickened portion of the intima were measured by an image resolution device (LUZEX2D).

The test compound began to be administered subcutaneously at a rate of 3.2 µg/rat/hr using a miniosmotic pump buried in the back of the rat from three days before the surgery and was continued until 11 days after the surgery. The activity of the test compound in suppressing intima thickening was found from the following formula.

Intima thickening suppression rate (%)=(1-T/C)×100

(wherein, T shows shows the ratio between the area of the thickened portion of the intima and the area of the media portion of the rats of the test compound group, while C shows that of the control group (group administered solvent) [Intima/Media])

TABLE 11

Test Results

| Drug No. | Subjects | Intima (mm²) (average ± standard error) | Media (mm²) | Intima /Media | Suppression rate (%) |
|---|---|---|---|---|---|
| Control | 8 | 0.288 ± 0.033 | 0.200 ± 0.005 | 1.399 ± 0.148 | — |
| Test compound | 9 | 0.155* ± 0.044 | 0.197 ± 0.013 | 0.758* ± 0.194 | 45.8 |

*: p < 0.05 (comparison with control, student t-test)

As is clear from the test results, the test compound suppresses the thickening of the neointima of the carotid artery.

Example 101

Action in Suppressing Thickening of Intima After Trauma to Rat Carotid Artery Endothelium by Balloon Catheter Test compound:

Methyl(11R,12S,13E,15S)-9-butyryloxy-11,15-dihydroxy-15-cyclohexyl-16,17,18,19,20-pentanor-7-thiaprosta-8,13-dienoate The test was performed by the same method as in Example 100.

TABLE 12

Test Results

| Drug No. | Subjects | Intima (mm²) (average ± standard error) | Media (mm²) | Intima /Media | Suppression rate (%) |
|---|---|---|---|---|---|
| Control | 8 | 0.305 ± 0.039 | 0.234 ± 0.009 | 1.255 ± 0.141 | — |
| Test compound | 9 | 0.167* ± 0.029 | 0.211 ± 0.016 | 0.784* ± 0.092 | 37.5 |

*: p < 0.05 (comparison with control, student t-test)

As is clear from the test results, the test compound suppresses the thickening of the neointima of the carotid artery.

Example 102

Action in Suppressing Thickening of Intima After Trauma to Rabbit Carotid Artery Endothelium by Balloon Catheter Test compound:

Methyl(11R,12S,13E,15S,17R)-9-butyryloxy-11,15-dihydroxy-17,20-dimethyl-7-thiaprosta-8,13-dienoate The test was performed in the following manner in accordance with the method of Clowes et al. (Lab. Invest., 49, 206, 1983). Use was made of New Zealand white rabbits (male) of approximately 4 kg body weight. The neck portion of each rabbit was opened under anesthesia by sodium pentobarbitol, then a balloon catheter (Fogarty, 3F) was inserted from the right external carotid artery until the starting portion of the common carotid artery. The balloon was expanded by saline to an extent causing a light resistance, then the catheter was pulled out in that state up to the carotid artery to give trauma to the intima. This procedure was performed once, then the catheter was withdrawn and the external carotid artery was ligated. After 10 days, the chest was opened under anesthesia by pentobarbitol and the right common carotid artery was removed and immobilized by a neutral formalin solution. The immobilized carotid artery was dyed by Elastica van Gieson dye, then the areas of the media and intima were measured by an image resolution device (LUZEX2D).

The test compound began to be administered subcutaneously at a rate of 32 µg/rabbit/hr using a miniosmotic pump buried in the back of the rabbit from three days before the surgery and was continued until 10 days after the surgery. The activity of the test compound in inhibiting intima thickening was found from the following formula.

Intima thickening suppression rate (%)=(1-T/C)×100 wherein, T shows shows the ratio between the area of the thickened portion of the intima and the area of the media portion of the rabbits of the test compound group, while C shows that of the control group (group administered solvent) [Intima/Media]

TABLE 13

Test Results

| Drug No. | Subjects | Intima (mm²) | Media (mm²) | Intima /Media | Suppression rate (%) |
|---|---|---|---|---|---|
| | | (average ± standard error) | | | |
| Control | 8 | 0.065 ± 0.008 | 0.291 ± 0.020 | 0.216 ± 0.021 | — |
| Test compound | 9 | 0.055 ± 0.011 | 0.367 ± 0.016 | 0.152 ± 0.030 | 29.9 |

Example 103

Measurement of Platelet Aggregation Inhibiting Activity (1) Measurement of rat platelet aggregation inhibiting activity Wistar rats (males, approximately 400 g) were made to fast for one day, the entire blood was removed from the chest artery under anesthesia by ether, then a ⅒ volume of 3.8% aqueous solution of sodium citrate was added and immediately mixed in. The solution was centrifuged at 1000 rpm for 10 minutes, then the upper layer was used as the platelet rich plasma. The lower layer was centrifuged at 3000 rpm for 10 minutes and the upper layer of that was used as the platelet poor plasma. The platelet rich plasma was diluted by the platelet poor plasma to give a number of platelets of $3.5 \times 10^8/mm^3$. This was used for the measurement. Note that the measurement of the platelets was performed using an automatic blood cell counter MEK-4500 (Nihon Koden). The measurement of the platelet aggregation was performed by measuring the turbidity using an NBS HEMA TRACER 801 (M.C. Medical). 90 µl of the platelet solution was inserted in a cuvette, then 5 µl each of the test compounds was added to give the target final concentration. The result was heated for one minute at 37° C., then 5 µl of a 100 µM aqueous solution of adenosine 2-phosphate (M.C. Medical) was added to induce platelet aggregation. The aggregation inhibiting activity was found from the following formula.

Aggregation inhibiting rate (%)={1-(maximum change of turbidity at time of addition of drug)/(maximum change of turbidity at time of non-addition of drug)}×100

Further, the concentration of the compound giving 50% inhibition was used as the $IC_{50}$. The results are shown in Tables 14 and 15.

(2) Measurement of human platelet aggregation inhibiting activity 50 ml portions of venous blood supplied from healthy human volunteers were used to prepare the platelet rich plasma and the platelet poor plasma in the same way as above. The measurement of the platelet aggregation was performed in the same way as above. However, unlike with the measurement of the rat platelet aggregation inhibiting activity, the test compound was added to the platelet poor plasma in advance and warmed for 5 minutes at 37° C., then the platelet rich plasma was added to give a number of platelets of $3.5 \times 10^8/mm^3$. At the same time, 5 µl of 100 µM an aqueous solution of adenosine 2-phosphate (M.C. Medical) was added to induce platelet aggregation. The aggregation inhibiting activity was calculated in the same way as mentioned above. The results are shown in Table 16.

TABLE 14

Platelet Aggregation Inhibiting Activity (Rat)

| Test compound | $IC_{50}$ (nM) |
|---|---|
| | 129 |
| | 52 |
| | 500 |
| | 1285 |
| | 221 |
| | 629 |

TABLE 15
Platelet Aggregation Inhibiting Activity (Rat)
| Test compound | IC$_{50}$ (nM) |
|---|---|
| 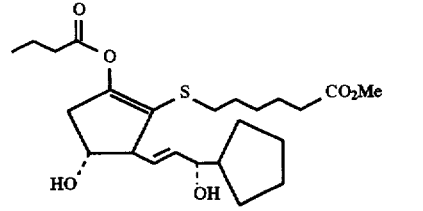 | 284 |
| 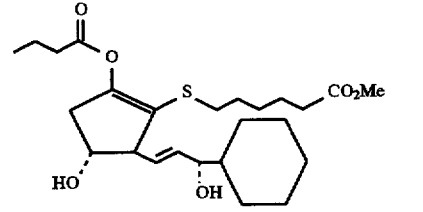 | 73 |
| 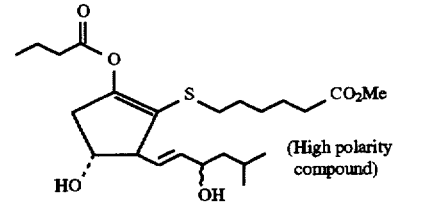 (High polarity compound) | 380 |
| 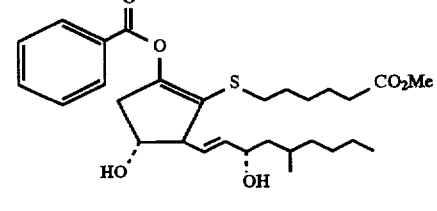 | 700 |
| 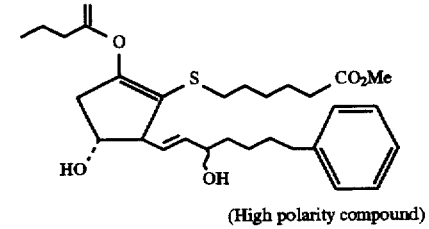 (High polarity compound) | 290 |
| 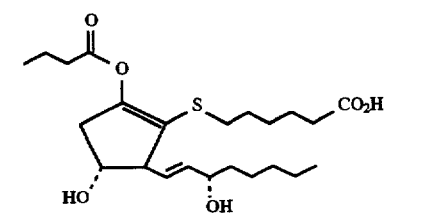 | 300 |
TABLE 16
Platelet Aggregation Inhibiting Activity (Human)
| Test compound | IC$_{50}$ (nM) |
|---|---|
| 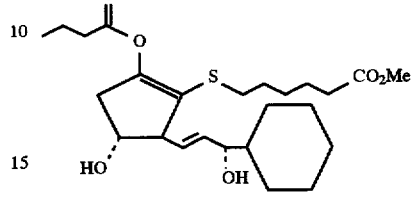 | 120 |
| 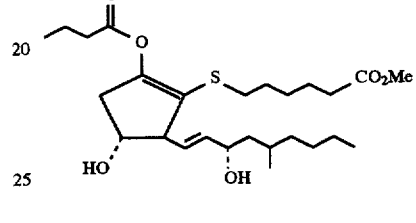 | 58 |
| 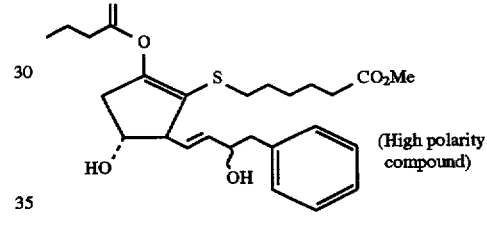 (High polarity compound) | 50 |
| 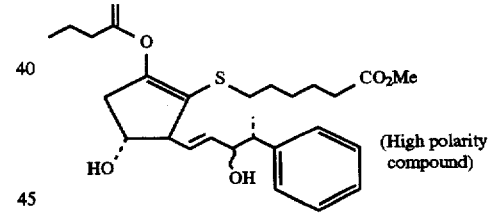 (High polarity compound) | 49 |
| 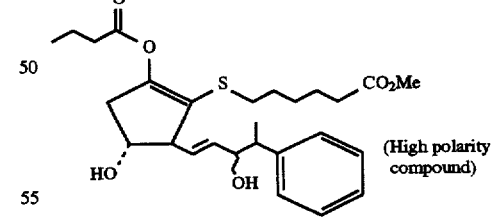 (High polarity compound) | 105 |
| 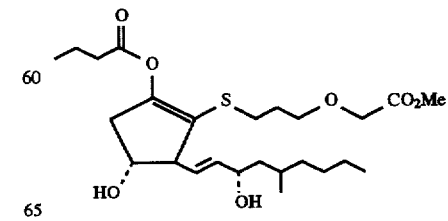 | 59 |

We claim:

1. A 7-thiaprostaglandin selected from the group consisting of compounds of the formula (I):

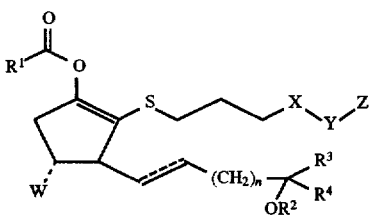

wherein, $R^1$ is a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, a substituted or unsubstituted phenyl($C_1$ to $C_2$)alkyl group, a substituted or unsubstituted phenoxy($C_1$ to $C_7$)alkyl group, or a group representing a substituted or unsubstituted amino acid residue including a carbonyl group of an enol ester, $R^2$ is a hydrogen atom, a tri($C_1$ to $C_7$ hydrocarbon)silyl group, or a group forming an acetal bond along with the oxygen atom of the hydroxyl group, $R^3$ is a hydrogen atom, a methyl group, or a vinyl group, $R^4$ is a $C_1$ to $C_8$ straight or branched alkyl group, a $C_2$ to $C_8$ straight or branched alkenyl group, a $C_2$ to $C_8$ straight or branched alkynyl group, a substituted or unsubstituted phenyl group, a substituted or unsubstituted $C_3$ to $C_{10}$ cycloalkyl group, or $R^4$ is further a straight or branched $C_1$ to $C_5$ alkyl group, a $C_2$ to $C_5$ alkenyl group, or a $C_2$ to $C_5$ alkynyl group substituted by a $C_1$ to $C_5$ alkoxyl group, a substituted or unsubstituted aromatic group, a substituted or unsubstituted phenoxy group, a substituted or unsubstituted $C_3$ to $C_{10}$ cycloalkyl group, or a substituted or unsubstituted hereto ring group, W is a hydrogen atom, a hydroxyl group, a tri($C_1$ to $C_7$ hydrocarbon)siloxy group, or a group forming an acetal bond, X—Y is an ethylene group, a vinylene group, or an ether bond where X is an oxygen atom and Y is a methylene group, Z is $CO_2R^5$ or $CONR^6R^7$, $R^5$ is a hydrogen atom, a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, a substituted or unsubstituted phenyl($C_1$ to $C_2$)alkyl group, or 1 equivalent of a cation, $R^6$ and $R^7$ may be the same or different and represent a hydrogen atom, a $C_1$ to $C_5$ straight or branched alkyl group, or a group forming a $C_4$ to $C_6$ hetero ring with the nitrogen atom of the amide, n is 0 or 1, and the symbol $=$ represents a double bond or single bond, or their enantiomers, or mixtures of any ratio of the same.

2. A 7-thiaprostaglandin as claimed in claim 1, wherein $R^1$ is a $C_1$ to $C_5$ straight or branched alkyl group, a substituted or unsubstituted phenyl group, or a group representing a substituted or unsubstituted amino acid residue including a carbonyl group of an enol ester, $R^2$ is a hydrogen atom, a trimethylsilyl group, a tert-butyldimethylsilyl group, or a 2-tetrahydropyranyl group, $R^3$ is a hydrogen atom or a methyl group, $R^4$ is a $C_1$ to $C_8$ straight or branched alkyl group, a substituted or unsubstituted phenyl group, a substituted or unsubstituted $C_3$ to $C_{10}$ cycloalkyl group, or a straight or branched $C_1$ to $C_5$ alkyl group substituted with a $C_1$ to $C_5$ alkoxyl group, a substituted or unsubstituted aromatic group, a substituted or unsubstituted phenoxy group, a substituted or unsubstituted $C_3$ to $C_{10}$ cycloalkyl group, or a substituted or unsubstituted hetero ring group, W is a hydrogen atom, a hydroxyl group, or a tert-butyldimethylsiloxy group, X—Y is an ethylene group, a vinylene group, or an ether bond where X is an oxygen atom and Y is a methylene group, Z is $CO_2R^5$ or $CONR^6R^7$, $R^5$ is a $C_1$ to $C_5$ straight or branched alkyl group, or an allyl group, $R^6$ and $R^7$ may be the same or different and represent a hydrogen atom or a $C_1$ to $C_5$ straight or branched alkyl group, n is 0 or 1, and the symbol $=$ is a double bond or a single bond.

3. A 7-thiaprostaglandin as claimed in claim 1, wherein $R^1$ is a $C_1$ to $C_5$ straight or branched alkyl group or a phenyl group, $R^2$ is a hydrogen atom, a trimethylsilyl group, a tert-butyldimethylsilyl group, or a 2-tetrahydropyranyl group, $R^3$ is a hydrogen atom or a methyl group, $R^4$ is a $C_1$ to $C_8$ straight or branched alkyl group, a substituted or unsubstituted phenyl group, a substituted or unsubstituted $C_3$ to $C_{10}$ cycloalkyl group, or a straight or branched $C_1$ to $C_5$ alkyl group substituted with a substituted or unsubstituted phenyl group, W is a hydroxyl group or a tert-butyldimethylsiloxy group, X—Y is an ethylene group, a vinylene group, or an ether bond where X is an oxygen atom and Y is a methylene group, Z is $CO_2R^5$, where $R^5$ is a methyl group, a butyl group, or an allyl group, n is 0, and the symbol $=$ is a double bond.

4. A 7-thiaprostaglandin as claimed in claim 1, wherein $R^1$ is a propyl group, $R^2$ and $R^3$ are hydrogen atoms, $R^4$ is a 2-methylhexyl group or a substituted or unsubstituted benzyl group, X—Y is an ethylene group or an ether bond where X is an oxygen atom and Y is a methylene group, Z is $CO_2R^5$, $R^5$ is a methyl group n is 0, and the symbol $=$ is a double bond.

5. A method for producing the 7-thiaprostaglandin as set forth in claim 1, comprising:

reacting organolithium compounds or organotin compounds having the formula (II):

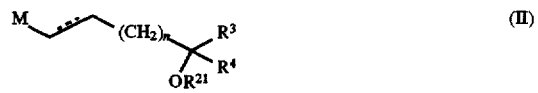

wherein, $R^{21}$ is a tri($C_1$ to $C_7$ hydrocarbon)silyl group or a group forming an acetal bond along with the oxygen atom of the hydroxyl group, M is a lithium atom or tri($C_1$ to $C_6$ hydrocarbon)stannyl group with an organocopper reagent generated from CuQ wherein, Q is a halogen atom, a cyano group, a phenylthio group, a 1-pentynyl group, or a 1-hexynyl group with a 2-organothio-2-cyclopentenone having the formula (III):

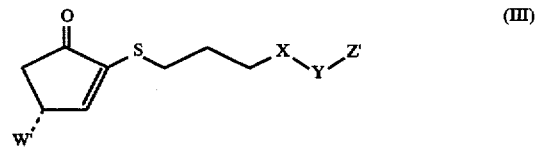

wherein, X—Y is the same as defined in claim 1, W' is a hydrogen atom, a tri($C_1$ to $C_7$ hydrocarbon)siloxy group, or a group forming an acetal bond, Z' is $CO_2R^{51}$, $R^{51}$ is a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, or a substituted or unsubstituted phenyl ($C_1$ to $C_2$)alkyl group or their enantiomers or mixtures of any ratio of the same to form an intermediate compound, then reacting said intermediate compound with a compound of $(R^1CO)_2O$ wherein, $R^1$ is the same as defined in claim 1 or $R^1COCl$ wherein, $R^1$ is the same as defined above or the following formula (IV):

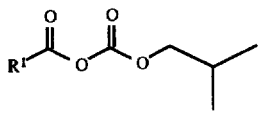

wherein, $R^1$ is the same as defined above to produce said 7-thiaprostaglandin.

6. A method for producing a prostaglandin comprising reacting a trans-1,2-bis(trialkylstannyl)ethylene or trans-1,2-bis(triphenylstannyl)ethylene having the formula (V):
wherein, P is a $C_1$ to $C_6$ straight or branched alkyl group or a phenyl group and an organocopper reagent generated from CuQ wherein, Q is a halogen atom, a cyano group, a phenylthio group, a 1-pentynyl group, or a 1-hexynyl group and a $C_1$ to $C_4$ straight or branched alkyllithium compound and a 2-organolithio-2-cyclopentenone having the formula (VI):

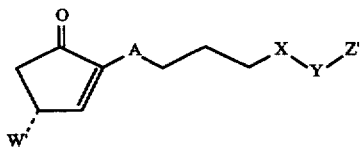

wherein, A is a bivalent sulfur atom or a methylene group, W' is a hydrogen atom, X—Y is a methylene group, a vinylene group, or an ether bond where X is an oxygen atom and Y is a methylene group, and Z' is $CO_2R^{51}$, $R^{51}$ is a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, or a substituted or unsubstituted phenyl ($C_1$ to $C_2$)alkyl group or their enantiomers or mixtures of any ratio of the same to form an intermediate compound, then reacting said intermediate compound with an acid anhydride or an acid halide represented by $(R^1CO)_2O$ wherein, $R^1$ is a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, a substituted or unsubstituted phenyl($C_1$ to $C_2$)alkyl group, a substituted or unsubstituted phenoxy($C_1$ to $C_7$)alkyl group, or a group representing a substituted or unsubstituted amino acid residue including a carbonyl group of an enol ester, or $R^1COCl$ wherein, $R^1$ is the same as defined above to synthesize a vinylstannyl compound having the formula (VII):

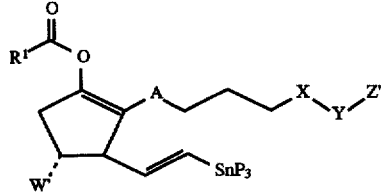

wherein, A, $R^1$, P, W', X—Y, and Z' are the same as defined above then reacting said vinylstannyl compound with a halogen molecule of $B_2$ wherein, B is an iodine atom or a bromine atom to derive a haloolefin compound having the formula (VIII):

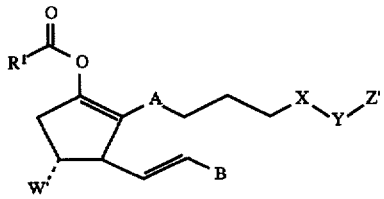

wherein, A, B, $R^1$, W', X—Y and Z' are the same as defined above then reacting said haloolefin compound with an aldehyde having the formula (IX):

wherein, $R^4$ is a $C_1$ to $C_8$ straight or branched alkyl group, a $C_2$ to $C_8$ straight or branched alkenyl group, a $C_2$ to $C_8$ straight or branched alkynlyl group, a substituted or unsubstituted phenyl group, a substituted or unsubstituted $C_3$ to $C_{10}$ cycloalkyl group, or $R^4$ is further a straight or branched $C_1$ to $C_5$ alkyl group, a $C_2$ to $C_5$ akenyl group or a $C_2$ to $C_5$ alkynyl group substituted by a $C_1$ to $C_5$ alkoxyl group, a substituted or unsubstituted aromatic group, a substituted or unsubstituted phenoxy group, a substituted or unsubstituted $C_3$ to $C_{10}$ cycloaklyl group or a substituted or unsubstituted hetero ring group, in the presence of $CrCl_2$, so as to produce a prostaglandin having the formula (X):

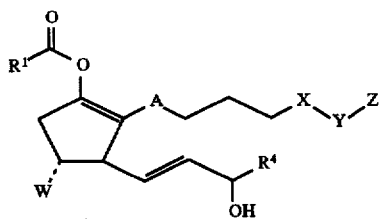

wherein, A, $R^1$, $R^4$, and X—Y, are the same as defined above, W is a hydroxyl group or a tert-butyldimethylsiloxy group, and Z is $CO_2R^5$, wherein $R^5$ is a methyl group.

7. A method for producing a prostaglandin as claimed in claim 6, wherein A is a bivalent sulfur atom.

8. A synthesis intermediate of a prostaglandin having the formula (XI):

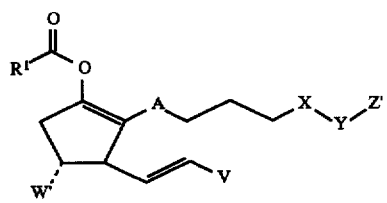

wherein, V is $SnP_3$ or B A is a bivalent sulfur atom or a methylene group, B is an iodine atom or a bromine atom, P is a $C_1$-$C_6$ straight or branched alkyl group or a phenyl group, $R^1$ is a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, a substituted or unsubstituted phenyl($C_1$ to $C_2$)alkyl group, a substituted or unsubstituted phenoxy($C_1$ to $C_7$)alkyl group, or a group representing a substituted or unsubstituted amino acid residue including a carbonyl group of an enol ester, W' is a hydrogen atom, X—Y is a methylene group, a vinylene group or an ether bond where X is an oxygen atom and Y is a methylene group; and Z' is $CO_2R^{51}$, where $R^{51}$ is a $C_1$ to $C_{10}$ straight or branched alkyl group, a $C_2$ to $C_{10}$ straight or branched alkenyl group, a substituted or unsubstituted phenyl group, a substituted or unsubstituted $C_3$ to $C_{10}$ cycloalkyl group, or a substituted or unsubstituted phenyl($C_1$ to $C_2$)alkyl group.

9. A synthesis intermediate of a prostaglandin as claimed in claim 8, wherein A is a bivalent sulfur atom.

10. The method according to claim 5, further comprising performing at least one reaction selected from the group consisting of the protection, hydrolysis and a salt-forming reaction.

11. The method according to claim 6, further comprising performing at least one reaction selected from the group consisting of the protection, hydrolysis and a salt-forming reaction.

* * * * *